(12) United States Patent
Lee et al.

(10) Patent No.: US 11,538,998 B2
(45) Date of Patent: Dec. 27, 2022

(54) ORGANIC COMPOUND, LIGHT EMITTING DIODE AND LIGHT EMITTING DEVICE HAVING THE COMPOUND

(71) Applicant: LG Display Co., Ltd., Seoul (KR)

(72) Inventors: Na Yeon Lee, Paju-si (KR); So Mang Kim, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 290 days.

(21) Appl. No.: 16/711,168

(22) Filed: Dec. 11, 2019

(65) Prior Publication Data

US 2020/0194678 A1 Jun. 18, 2020

(30) Foreign Application Priority Data

Dec. 12, 2018 (KR) .................... 10-2018-0159939

(51) Int. Cl.
  *H01L 51/50* (2006.01)
  *H01L 51/00* (2006.01)
  *C07D 209/88* (2006.01)
  *C07D 209/86* (2006.01)

(52) U.S. Cl.
  CPC ........ *H01L 51/0061* (2013.01); *C07D 209/86* (2013.01); *C07D 209/88* (2013.01); *H01L 51/0072* (2013.01); *H01L 51/502* (2013.01); *H01L 51/5004* (2013.01); *H01L 51/506* (2013.01); *H01L 51/5064* (2013.01); *H01L 2251/552* (2013.01)

(58) Field of Classification Search
  None
  See application file for complete search history.

(56) References Cited

U.S. PATENT DOCUMENTS

| 9,085,729 B2 | 7/2015 | Coggan et al. |
| 2002/0119384 A1* | 8/2002 | Koyama ............. H01L 51/5265 430/79 |
| 2017/0133614 A1* | 5/2017 | Gu ....................... H01L 51/0078 |

FOREIGN PATENT DOCUMENTS

| JP | 2003-026641 A | 1/2003 | |
| JP | 2004-107292 A | 4/2004 | |
| KR | 2014096227 | * 8/2005 | ............. H01L 51/50 |
| KR | 10-2010-0023909 A | 3/2010 | |

(Continued)

OTHER PUBLICATIONS

Zong et. al.,A new binaphthol based hole-transporting materials for perovskite solar cells, Tetrahedron 73 (2017) 3398e3405 (Year: 2017).*

(Continued)

*Primary Examiner* — Gregory D Clark
(74) *Attorney, Agent, or Firm* — Polsinelli PC

(57) ABSTRACT

The present disclosure relates to an organic compound having a binaphthyl core and a group connected to the biphenyl core and having excellent charge mobility property, and a light emitting diode and a light emitting device having the organic compound. The organic compound can be applied into the light emitting diode by using solution process and has very deep HOMO energy level. When the organic compound is applied into a chare transfer layer, a HOMO energy level bandgap between the charge transfer layer and an emitting material layer is reduced so that holes and electrons can be injected into the emitting material layer in a balanced manner.

25 Claims, 5 Drawing Sheets

(56) References Cited

FOREIGN PATENT DOCUMENTS

KR   10-2014-0116526 A   10/2014

OTHER PUBLICATIONS

Chinese Office Action dated Oct. 24, 2022 issued in corresponding Patent Application No. 201911265006.0 (English translation, 14 pages).
Fan et al, "Blue-light-emitting and hole-transporting molecular materials based on amorphous triphenylamine-functionalized twisted binaphithyl", Comptes Rendus Chimie, Dec. 31, 2014, vol. 17, pp. 1102-1108.
He et al., "Chiral binapththylbisbipyridine-based copper(I) coordination polymer gels as supramolecular catalyts", Chem. Comm., published on Mar. 29, 2010. vol. 46, pp. 3532-3534.
Rana et al., "Selective DNA Recognition and Cytotoxicity of Water-Soluble Helical Metallosupramolecular Polymers", Bioconjugate Chemistry, Dec. 31, 2016, vol. 27, pp. 2307-2314.

\* cited by examiner $\Delta G_H > \Delta G_L$
Injection amount of h⁺ < Injection amount of e⁻

$\Delta G'_H \simeq \Delta G_L$
Injection amount of ⓗ⁺ ≃ Injection amount of ⓔ⁻

ORGANIC COMPOUND, LIGHT EMITTING DIODE AND LIGHT EMITTING DEVICE HAVING THE COMPOUND

CROSS REFERENCE TO RELATED APPLICATION

This application claims the benefit under 35 U.S.C. § 119(a) of Korean Patent Application No. 10-2018-0159939, filed on Dec. 12, 2018, which is hereby incorporated by reference in its entirety.

BACKGROUND

Field of the Disclosure

The present disclosure relates to an organic compound, and more specifically, to an organic compound that realizes solution process and has an excellent charge mobility property, and a light emitting diode and a light emitting device having the same.

Description of the Background

As electronic and information technologies progress, a field of displays for processing and displaying a large quantity of information has been developed rapidly. Accordingly, various flat panel display devices such as a liquid crystal display (LCD) device, an organic light emitting diode (OLED) display device, etc. have been developed. Among these flat panel display devices, OLED has come into spotlight as a next-generation display device replacing LCD since it enables thin structure and shows lower consumption power.

In case of increasing current densities or raising driving voltages in the OLED for improving luminance in OLED display device, the luminous life span of the OLED become shorter owing to thermal degradation and deteriorations of organic materials in the OLED. Besides, the OLED has not achieved high color gamut required in ITU-R Recommendation BT.2020 (REC. 2020 or BT.2020) of International Telecommunication Union as regards 4K/UHD standards.

Recently, a display device using inorganic luminescent particles such as quantum dots (QDs) has been developed. QD is an inorganic luminescent particle that emits light as unstable stated excitons drop from conduction band to valence band. QD has large extinction coefficient, high quantum yield among inorganic particles and generates strong fluorescence. Besides, since QD has different luminescence wavelengths as its sizes, it is possible to obtain light within the whole visible light spectra so as to implement various colors by adjusting sizes of QD.

When QD is used as a luminous material in an emitting material layer (EML), it is possible to enhance color purity of individual pixel and implement white (W) light having high purity of red (R), green (G) and blue (B) so as to achieve Rec.2000 standard. Accordingly, Quantum Dot Light emitting Diode (QLED) which uses QD as luminous material has come into spotlight.

Surface defects, which is generated at interfaces between emissive layers or a surface of the emissive layers in the OLED and QLED, has been a limitation in realizing a desired level of luminous efficiency. In addition, since there is a charge un-balancing due to the relative mobility difference between the holes and electrons, the OLED and QLED shows reduced luminous efficiency.

The OLED or QLED may have multiple laminated films by using solution process. When the material in the lower layer is dissolved in the solvent used to disperse another material for forming the upper layer, there may occurs mixing of these materials at the interface between the upper and lower layers. Accordingly, when adjacent emissive layers of the OLED and QLED are formed through solution process, a compatible solvent capable of dispersing and dissolving all the luminous materials and/or charge transporting material, each of which constitutes the adjacent emissive layers, cannot be used. Therefore, the kinds of the solvents usable for each emissive layer in the OLED and QLED to which solution process is applied are limited. Therefore, there is a need to develop a material which can be dispersed and dissolved in the limited solvent and has an appropriate energy level.

SUMMARY

Accordingly, the present disclosure is directed to an organic compound, a light emitting diode and a light emitting device including the organic compound that substantially obviates one or more of the problems due to the limitations and disadvantages of the related art.

More specifically, the present disclosure provides an organic compound having excellent charge mobility rate and can inject charges into an emitting material layer in a balanced manner, and a light emitting diode and a light emitting device having the organic compound.

In addition, the present disclosure provides an organic compound realizing high luminous efficiency and low driving voltage, and a light emitting diode and a light emitting device having the organic compound.

Additional features and advantages of the disclosure will be set forth in the description which follows, and in part will be apparent from the description, or may be learned by practice of the disclosure. Other advantages of the disclosure will be realized and attained by the structure particularly pointed out in the written description and claims hereof as well as the appended drawings.

According to an aspect, the present disclosure provides an organic compound having the following structure of Chemical Formula 1:

Chemical Formula 1

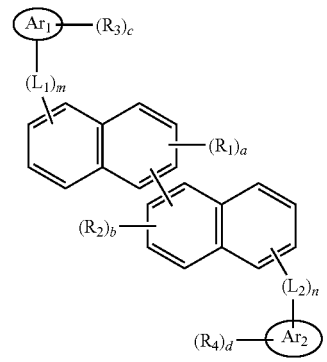

wherein each of $R_1$ and $R_2$ is independently protium, deuterium, tritium, linear or branched $C_1$~$C_{20}$ alkyl group or $C_1$~$C_{20}$ alkoxy group; each of a and b is independently an integer of 1 to 3; each of $Ar_1$ and $Ar_2$ is independently $C_4$~$C_{30}$ hetero aryl group or nitrogen (N), when each of $Ar_1$ and $Ar_2$ is independently $C_4$~$C_{30}$ hetero aryl group, each of $R_3$ and $R_4$ is independently linear or branched $C_1$~$C_{10}$ alkyl group, $C_5$~$C_{30}$ aryl amino group unsubstituted or substituted with linear or branched $C_1$~$C_{10}$ alkyl group, $C_4$~$C_{30}$ hetero aryl amino group unsubstituted or substituted with linear or branched $C_1$~$C_{10}$ alkyl group, $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof, or $C_4$~$C_{30}$ hetero aryl group unsubstituted or substituted with a group selected from the group consisting of linear or branched $C_1$-$C_{10}$ alkyl group, $C_5$~$C_{30}$ aryl group, $C_4$~$C_{30}$ hetero aryl group and combination thereof, and each of c and d is independently a number of substituents $R_3$ and $R_4$ and an integer of 1 to 3, when each of $Ar_1$ and $Ar_2$ is independently nitrogen (N), each of $R_3$ and $R_4$ is independently $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof, or $C_4$~$C_{30}$ hetero aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof, and each of c and d is a number of substituents and 2; each of $L_1$ and $L_2$ is independently unsubstituted or substituted $C_5$~$C_{30}$ arylene group or $C_4$~$C_{30}$ hetero arylene group; and each of m and n is independently integer of 0 or 1.

According to another aspect, the present disclosure provides a light emitting diode comprises first and second electrodes facing each other and an emissive layer between the first and second electrodes and including a hole transfer layer, wherein the hole transfer layer includes the organic compound.

According to still another aspect, the present disclosure provides a light emitting device comprising a substrate and the light emitting diode as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of the disclosure, illustrate implementations of the disclosure and together with the description serve to explain the principles of aspects of the disclosure.

In the drawings.

DETAILED DESCRIPTIONS

Figure 1:
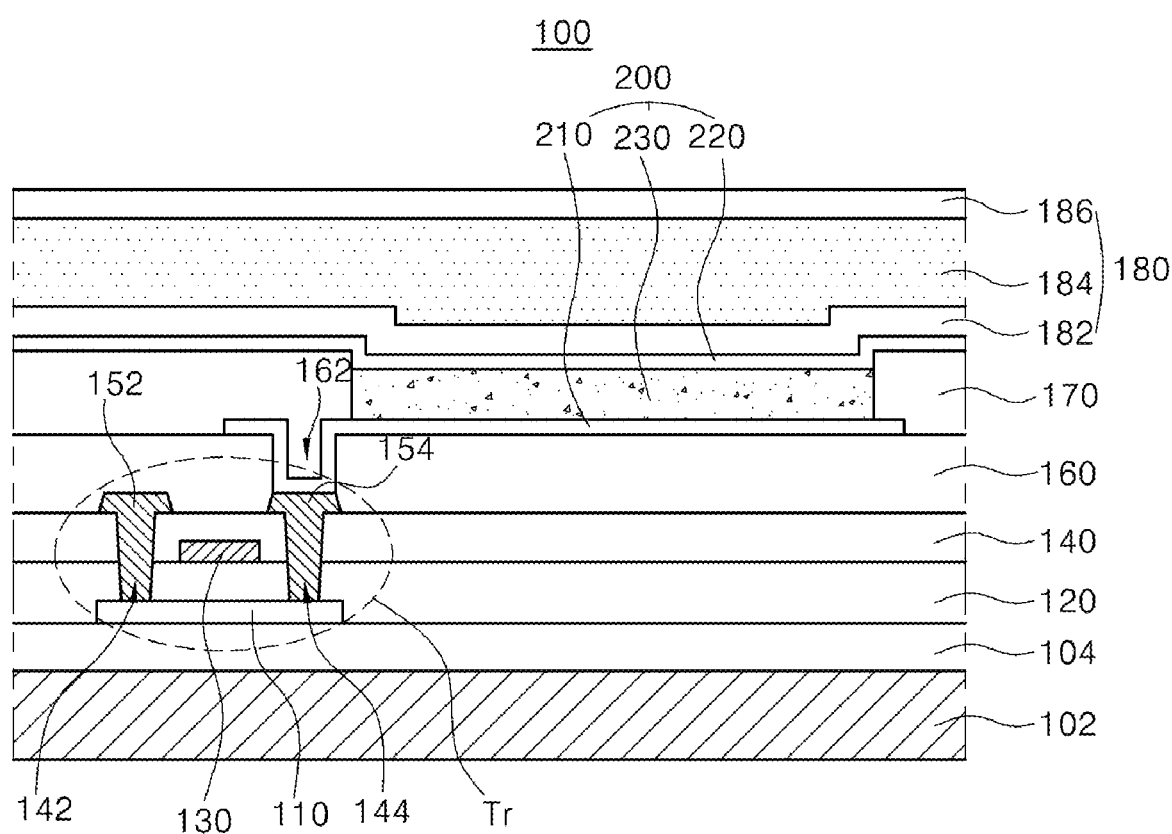
FIG. 1 is a schematic cross-sectional view illustrating a light emitting display device of the present disclosure.

Reference will be now be made in detail to aspects of the disclosure, examples of which are illustrated in the accompanying drawings.

Organic Compound

The materials used for charge transporting in the light emitting diode should have excellent charge mobility and can inject charges into an emitting material layer in a balance mode, i.e. should have proper energy levels. In addition, if those materials can form thin films through a solution process rather than a deposition processes, it is possible to reduce material wastes. An organic compound in accordance with an aspect of the present disclosure can satisfy those requirements and may have the following structure of Chemical Formula 1:

Chemical Formula 1

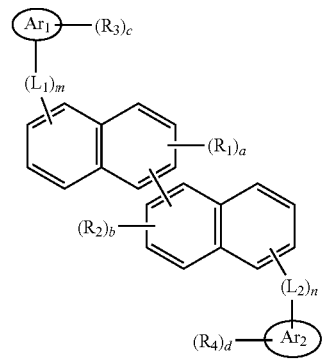

In Chemical Formula 1, each of $R_1$ and $R_2$ is independently protium, deuterium, tritium, linear or branched $C_1$~$C_{20}$ alkyl group or $C_1$~$C_{20}$ alkoxy group; each of a and b is independently an integer of 1 to 3. Each of $Ar_1$ and $Ar_2$ is independently $C_4$~$C_{30}$ hetero aryl group or nitrogen (N). When each of $Ar_1$ and $Ar_2$ is independently $C_4$~$C_{30}$ hetero aryl group, each of $R_3$ and $R_4$ is independently linear or branched $C_1$~$C_{10}$ alkyl group, $C_5$~$C_{30}$ aryl amino group unsubstituted or substituted with linear or branched $C_1$~$C_{10}$ alkyl group, $C_4$~$C_{30}$ hetero aryl amino group unsubstituted or substituted with linear or branched $C_1$~$C_{10}$ alkyl group, $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof, or $C_4$~$C_{30}$ hetero aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof, and each of c and d is independently a number of substituents $R_3$ and $R_4$ and an integer of 1 to 3. When each of $Ar_1$ and $Ar_2$ is independently is nitrogen (N), each of $R_3$ and $R_4$ is independently $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof, or $C_4$~$C_{30}$ hetero aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof, and each of c and d is a number of substituents and 2. Each of $L_1$ and $L_2$ is independently unsubstituted or substituted $C_5$~$C_{30}$ arylene group or $C_4$~$C_{30}$ hetero arylene group. And each of m and n is independently integer of 0 or 1.

As used herein, the term "unsubstituted" means that hydrogen atom is bonded, and in this case hydrogen atom includes protium, deuterium and tritium.

A substituent in "substituted" as used herein may include, but are not limited to, $C_1$~$C_{20}$ alkyl group unsubstituted or substituted with halogen, cyano group and/or nitro group; $C_1$~$C_{20}$ alkoxy group unsubstituted or substituted with halogen, cyano group and/or nitro group; halogen atom; cyano group; alkyl halide such as $CF_3$; and hydroxyl group, carboxyl group, carbonyl group, amino group, $C_1$~$C_{10}$ alkyl amino group, $C_5$~$C_{30}$ aryl amino group, $C_4$~$C_{30}$ hetero aryl amino group, nitro group, hydrazyl group, sulfonic group, $C_1$~$C_{20}$ alkyl silyl group, $C_1$~$C_{20}$ alkoxy silyl group, $C_3$~$C_{30}$ cycloalkyl group, $C_5$~$C_{30}$ aryl silyl group, $C_4$~$C_{30}$ hetero aryl silyl group, $C_5$~$C_{30}$ aryl group and $C_4$~$C_{30}$ hetero aryl group, each of which is unsubstituted or substituted with halogen, cyano group and/or nitro group, respectively.

As used herein, the term "hetero" described in "hetero aromatic ring", "hetero aromatic group", "hetero alicyclic ring", "hetero cyclic alkyl group", "hetero aryl group", "hetero aralkyl group", "hetero aryloxyl group", "hetero aryl amino group", "hetero arylene group", "hetero aralkylene group", "hetero aryloxylene group", and the likes means that at least one carbon atoms, for example 1 to 5 carbon atoms, forming such aromatic or alicyclic rings are substituted with at least one hetero atoms selected from the group consisting of N, O, S and combination thereof.

In one exemplary aspect, the $C_5$~$C_{30}$ aryl group, each of which constitutes respectively $R_3$ and $R_4$ or can be substituted respectively to $R_3$ and $R_4$, may include, but are not limited to, an unfused or fused aryl group such as phenyl, biphenyl, terphenyl, tetraphenyl, naphthyl, anthracenyl, indenyl, phenalenyl, phenanthrenyl, azulenyl, pyrenyl, fluorenyl, tetracenyl, indacenyl and spiro fluorenyl, each of which is independently unsubstituted or substituted with at least one of $C_1$~$C_{10}$ alkyl group, $C_5$~$C_{30}$ aryl group and $C_4$~$C_{30}$ hetero aryl group.

For example, when each of $R_3$ and $R_4$ is independently $C_5$~$C_{30}$ aryl group, each of $R_3$ and $R_4$ may independently include, but are not limited to, phenyl, naphthyl, anthracenyl, indenyl, phenalenyl, phenanthrenyl, azulenyl, pyrenyl, fluorenyl, tetracenyl, indacenyl or spiro fluorenyl, each of which is unsubstituted or substituted with alkyl group and/or aromatic or hetero aromatic group.

In an alternative aspect, when each of $Ar_1$ and $Ar_e$ is independently a nitrogen atom (N) or each of $R_3$ and $R_4$ is independently a aryl amino group, the $C_5$~$C_{30}$ aryl group substituted to the nitrogen atom of the amino group may by an aryl group consisting of 1-3 aromatic rings. If the number of the aromatic ring substituted to the nitrogen atom becomes larger, an energy bandgap of the organic compound may be excessively reduced due to the excessively long conjugated structures in the whole organic compound. For example, the $C_5$~$C_{30}$ aryl group, which may be substituted to the nitrogen atom of the amino group, may include, but are not limited to, phenyl, biphenyl, naphthyl, anthracenyl and/or fluorenyl, each of which is unsubstituted or substituted with alkyl group or aromatic or hetero aromatic group.

In another exemplary aspect, the $C_4$~$C_{30}$ hetero aryl group, each of which constitutes respectively $R_3$ and $R_4$ or can be substituted respectively to $R_3$ and $R_4$, may include, but are not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, indonocarbazolyl, indenocarbazolyl, benzofuronocarbazolyl, benzothienocarbazolyl, quinolinyl, iso-quinolinyl, phthlazinyl, qunixalinyl, cinnolyl, quinazolinyl, benzoquinolinyl, benzoiso-quinolinyl, benzoquianzolinyl, benzoquinoxalinyl, acridinyl, phenanthrolinyl, furanyl, pyranyl, oxazinyl, oxazolyl, oxadiazolyl, triazolyl, dioxinyl, benzofuranyl, dibenzofuranyl, thiopyranyl, thiazinyl, thiopnehyl, benzothiophenyl, dibenzothiophenyl and N-substituted fluorenyl, each of which is independently unsubstituted or substituted with at least one of $C_1$~$C_{10}$ alkyl group, $C_5$~$C_{30}$ aryl group and $C_4$~$C_{30}$ hetero aryl group.

As an example, when each of $R_3$ and $R_4$ is independently $C_4$~$C_{30}$ hetero aryl group, each of $R_3$ and $R_4$ independently may be, but are not limited to, a fused hetero aryl group such as indolyl, quinolinyl, iso-quinolinyl, phthalazinyl, quinoxalinyl, cinnolinyl, quinazolinyl, benzoquinolinyl, benzoiso-quinolinyl, benzoquinazolinyl, benzoquinoxalinyl, carbazolyl, benzocarbazolyl, dibenzocarbazolyl, inodolocarbazolyl, indenocarbazolyl, benzofurocarbazolyl, benzothienocarbazoly, acridiny, phenanthrolinyl, benzofuranyl, dibenzofuranyl, benzothiophenyl and dibenzothiophenyl, each of which is independently unsubstituted or substituted with at least one of $C_1$~$C_{10}$ alkyl group, $C_5$~$C_{30}$ aryl group and $C_4$~$C_{30}$ hetero aryl group.

In an alternative aspect, when each of $Ar_1$ and $Ar_e$ is independently a nitrogen atom (N) or each of $R_3$ and $R_4$ is independently a hetero aryl amino group, the $C_4$~$C_{30}$ hetero aryl group substituted to the nitrogen atom of the amino group may be an aryl group consisting of 1-3 hetero aromatic rings. For example, the $C_4$~$C_{30}$ hetero aryl group, which may be substituted to the nitrogen atom of the amino group, may include, but are not limited to, pyrrolyl, pyridinyl, pyrimidinyl, pyrazinyl, pyridazinyl, furanyl, thiophenyl, benzofuranyl, benzothiophenyl, dibenzofuranyl, dibenzothiophenyl, carbazolyl, carbolinyl, acridinyl, phenazinly, phenoxazinyl and/or phenothiazinyl, each of which is unsubstituted or substituted with alkyl group or aromatic ring or hetero aromatic group.

In one non-limited aspect, each of $L_1$ and $L_2$, a linker in Chemical Formula 1, mediates the binaphthyl core and each of $Ar_1$ and $Ar_e$, which is a group having excellent hole mobility property, and may be an aromatic or hetero aromatic linker. For example, when each of $L_1$ and $L_2$ is independently unsubstituted or substituted $C_5$~$C_{30}$ arylene group, each of $L_1$ and $L_2$ may include, but are not limited to, phenylene, biphenylene, terphenylene, tetraphenylene, indenylene, naphthylene, azulenylene, indacenylene, acenaphthylene, fluorenylene, spiro-fluorenylene, phenalenylene, phenanthrenylene, anthracenylene, fluoranthrenylene, triphenylenylne, pyrenylene, chrysenylene, naphthacenylene, picenylene, perylenylene, pentaphenylene and hexacenylene, each of which is unsubstituted or substituted.

In an alternative aspect, when each of $L_1$ and $L_2$ is independently unsubstituted or substituted $C_4$~$C_{30}$ hetero arylene group, each of $L_1$ and $L_2$ may include, but are not limited to, pyrrolylene, imidazolylene, pyrazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, benzoquinolinylene, benzoisoquinolinylene, benzoquinazolinylene, benzoquinoxalinylene, cinnolinylene, phenanthridinylene, acridinylene, phenanthrolinylene, phenazinylene, benzoxazolylene, benzimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, triazinylene, dibenzofuranylene, benzofurodibenzofuranylene, benzothienobenzofuranylene, benzothienodibenzofuranylene, dibenzothiophenylene, benzothienobenzothiophenylene, benzothienodibenzothiophenylene, carbazolyene, benzocarbazolylene, dibenzocarbazolylene, indolocarbazolylene, indenocarbazolylene, benzofurocarbazolylene, benzothienocarbazolylene, imidazopyrimidinylene and imidazopyridinylen, each of which is unsubstituted or substituted.

In an exemplary aspect, when the number of the aromatic or hetero aromatic ring becomes larger, an energy bandgap of the organic compound may be excessively reduced due to the excessively long conjugated structures in the whole organic compound. As an example, each of $L_1$ and $L_2$ may independently include 1-2 aromatic or hetero aromatic rings, alternatively one aromatic or hetero aromatic ring. With regard to charge injection and/or transportation properties, each of $L_1$ and $L_2$ may be a 5-membered to a 7-membered aromatic or hetero aromatic ring, alternatively a 6-membered aromatic or hetero aromatic ring. For example, each of $L_1$ and $L_2$ may independently include, but are not limited to, phenylene, biphenylene, naphthylene, pyrrolylene, imidazoylene, pyridylene, pyrazolylene, pyridinylene, pyrazinylene, pyrimidinylene, pyridazinylene, furanlyene and thiophenylene, each of which is unsubstituted or substituted.

In still another exemplary aspect, $R_1$ and $R_2$, $Ar_1$ and $Ar_e$, $R_3$ and $R_4$, $L_1$ and $L_2$, a to c and/or m and n may be identical to each other.

Since the organic compound having the structure of Chemical Formula 1 includes a fused aromatic core including a binaphthyl core, the compound may have a deep or low Highest Occupied Molecular Orbital (HOMO) energy level. When the organic compound having the structure of Chemical Formula 1 is introduced into a hole transfer layer, it is possible to reduce a HOMO energy level bandgap between the hole transfer layer and a emitting material layer, as described below. Moreover, the organic compound having the structure of Chemical Formula 1 has an excellent hole mobility property and can be laminated in a light emitting diode using a solution process.

Accordingly, holes and electrons can be injected into an emitting material layer in a balanced manner by applying the organic compound having the structure of Chemical Formula 1 to the light emitting diode. When the organic compound having the structure of Chemical Formula 1 is applied into the light emitting diode, holes and electrons, each of which is injected from an anode and cathode, can be transported into the emitting material layer without quenching so as to form effective exciton. Accordingly, luminescence can be realized at a region where luminous materials exist, not the interface between the emitting material layer and adjacent charge transfer layers. As a result, using the organic compound having the structure of Chemical Formula 1 enables the light emitting diode to enhance its luminous efficiency and to lower its driving voltage.

In one exemplary aspect, the organic compound having the structure of Chemical Formula 1 may include an organic compound having the following structure of Chemical Formula 2:

Chemical Formula 2

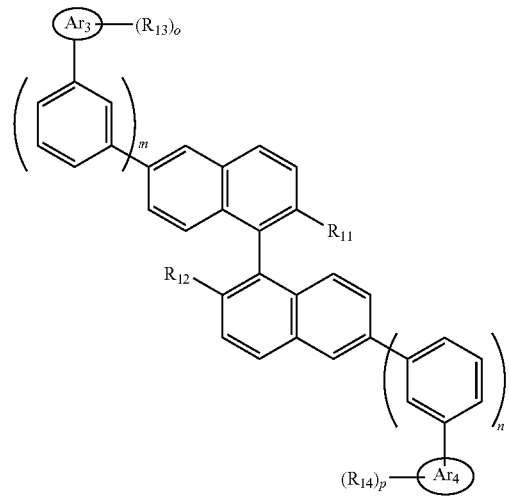

In Chemical Formula 2, each of $R_{11}$ and $R_{12}$ is independently protium, deuterium, tritium, linear or branched $C_1$~$C_{10}$ alkyl group or $C_1$~$C_{10}$ alkoxy group. Each of $Ar_3$ and $Ar_4$ is independently $C_{10}$~$C_{30}$ fused hetero aryl group. Each of $R_{13}$ and $R_{14}$ is independently linear or branched $C_1$~$C_{10}$ alkyl group, $C_5$~$C_{30}$ aryl amino group unsubstituted or substituted with linear or branched $C_1$~$C_{10}$ alkyl group, $C_4$~$C_{30}$ hetero aryl amino group unsubstituted or substituted with linear or branched $C_1$~$C_{10}$ alkyl group, $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof; or $C_4$~$C_{30}$ hetero aryl group unsubstituted or substituted with a group selected from the group consisting of linear or branched $C_1$-$C_{10}$ alkyl group, $C_5$~$C_{30}$ aryl group, $C_4$~$C_{30}$ hetero aryl group and combination thereof. Each of o and p is independently is a number of substituents $R_{13}$ and $R_{14}$ and an integer of 1 to 2. And each of m and n is identical as defined in Chemical Formula 1.

As an example, each of $Ar_3$ and $Ar_4$ in Chemical Formula 2 may independently be, but are not limited to, a fused $C_{10}$~$C_{30}$ hetero aryl group having at least one nitrogen atom. The fused hetero aryl group of $Ar_3$ and $Ar_4$ may include, but are not limited to, carbazolyl, acridinyl, carbolinyl, phenanthrenyl, phenanthrolinyl, phenazinly, phenoxazinyl and phenothiazinyl.

In still another exemplary aspect, R11 and R12, Ar3 and Ar4, R13 and R14, m and n and/or o and p in Chemical Formula 2 may be identical to each other:

In another exemplary aspect, each of $Ar_1$ and $Ar_2$ in Chemical Formula 1 may independently be a nitrogen atom substituted with aromatic and/or hetero aromatic groups. Such an organic compound may have the following structure of Chemical Formula 3:

Chemical Formula 3

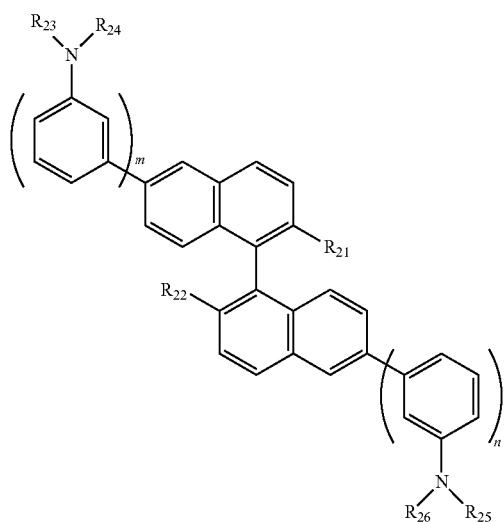

In Chemical Formula 3, each of $R_{21}$ and $R_{22}$ is independently protium, deuterium, tritium, linear or branched $C_1$~$C_{10}$ alkyl group or $C_1$~$C_{10}$ alkoxy group. Each of $R_{23}$ to $R_{26}$ is independently $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof; or $C_4$~$C_{30}$ hetero aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof. Each of m and n is identical as defined in Chemical Formula 1.

In one exemplary aspect, R21 and R22, R23 to R26 and/or m and n in Chemical Formula 3 may be identical to each other.

Particularly, the organic compound, which is excellent in hole mobility property, has very deep HOMO energy level and is capable of solution process, may include anyone having the following structure of Chemical Formula 4.

Chemical Formula 4

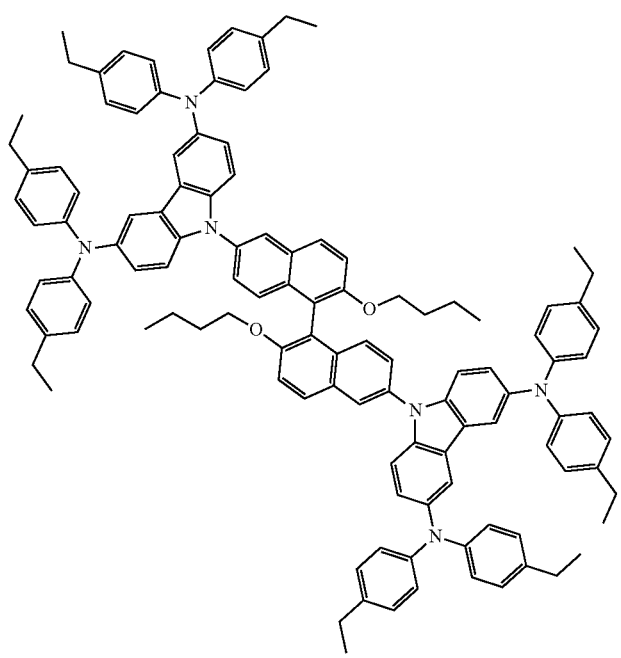

[H01]

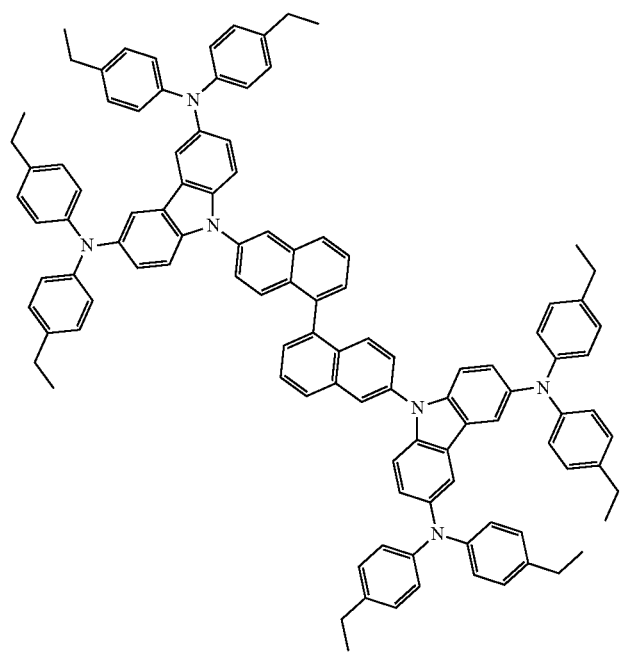
[H02]
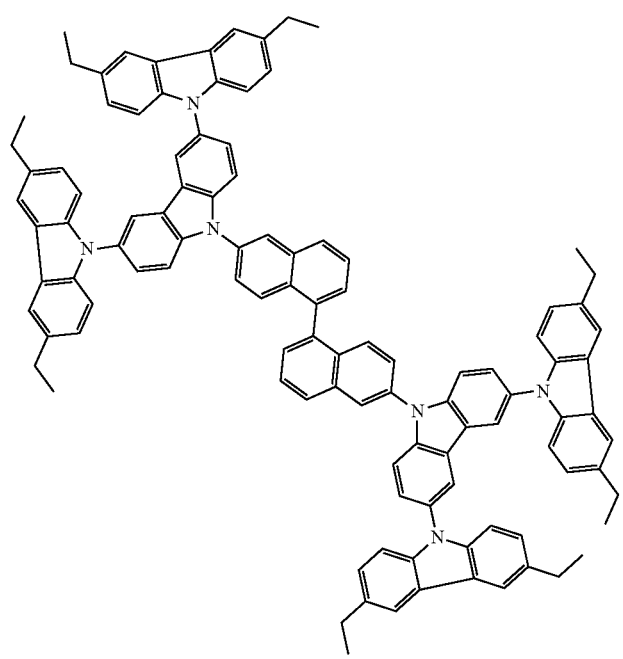
[H03]

-continued
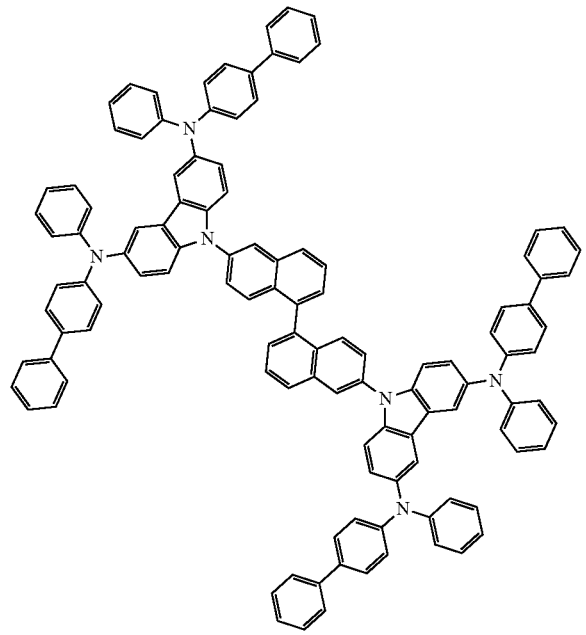
[H04]
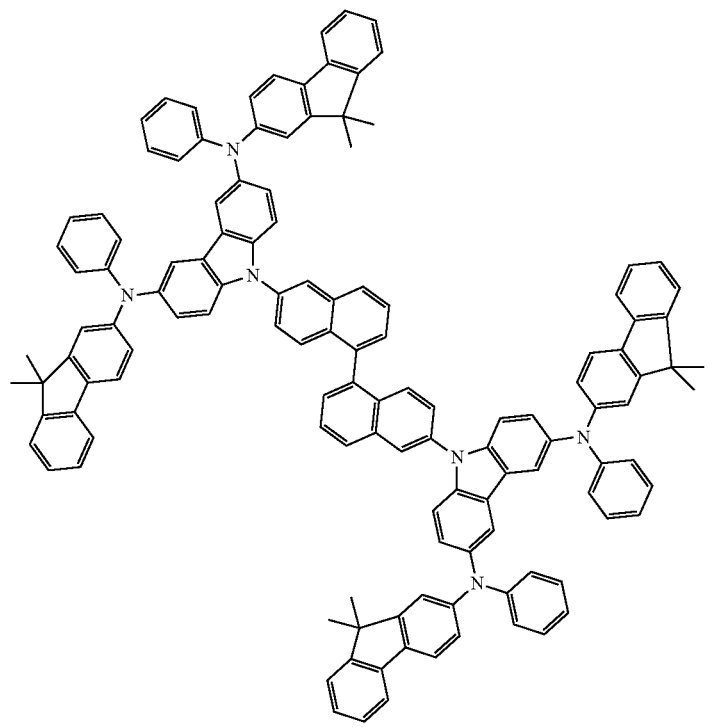
[H05]

[H06]
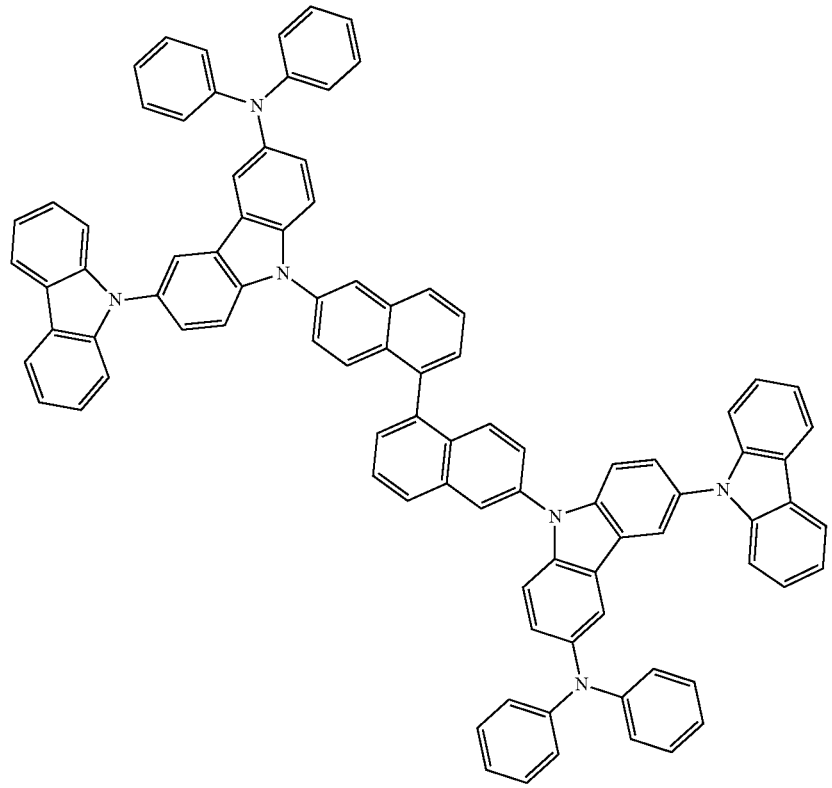
[H07]
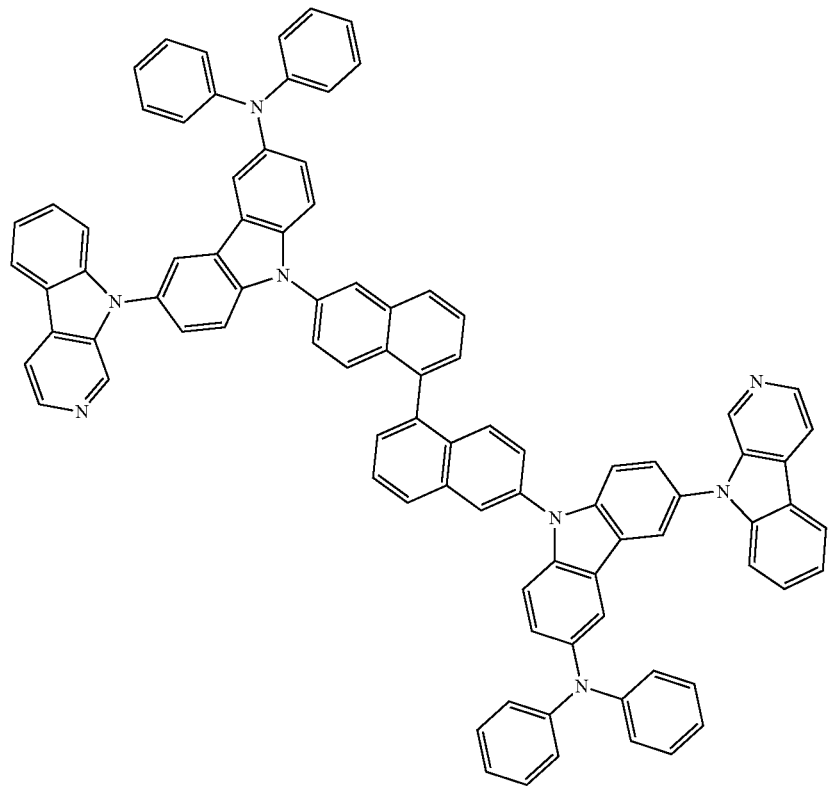

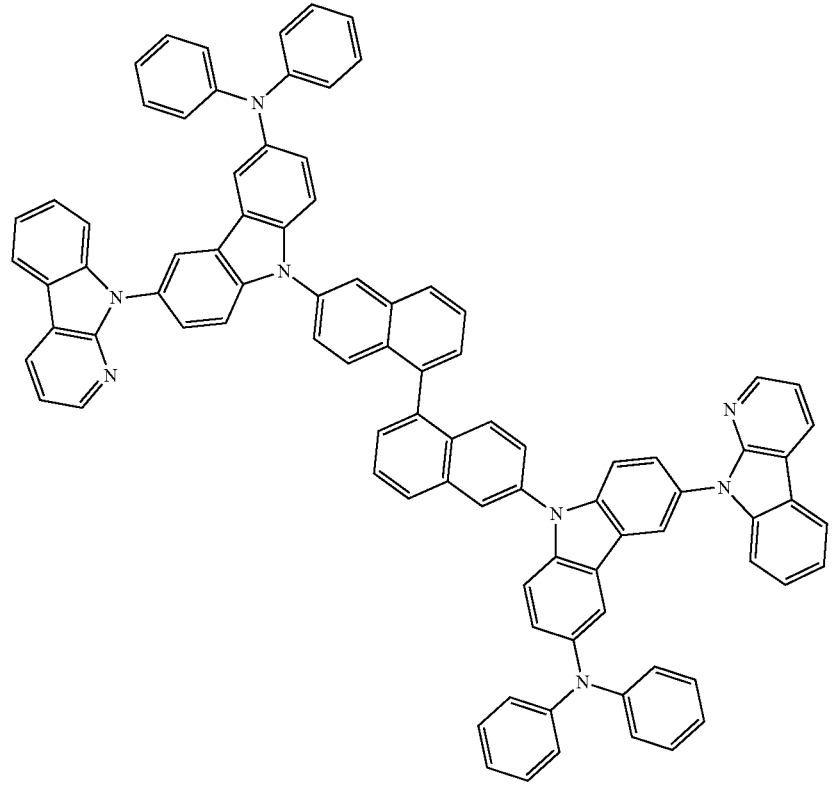
[H08]
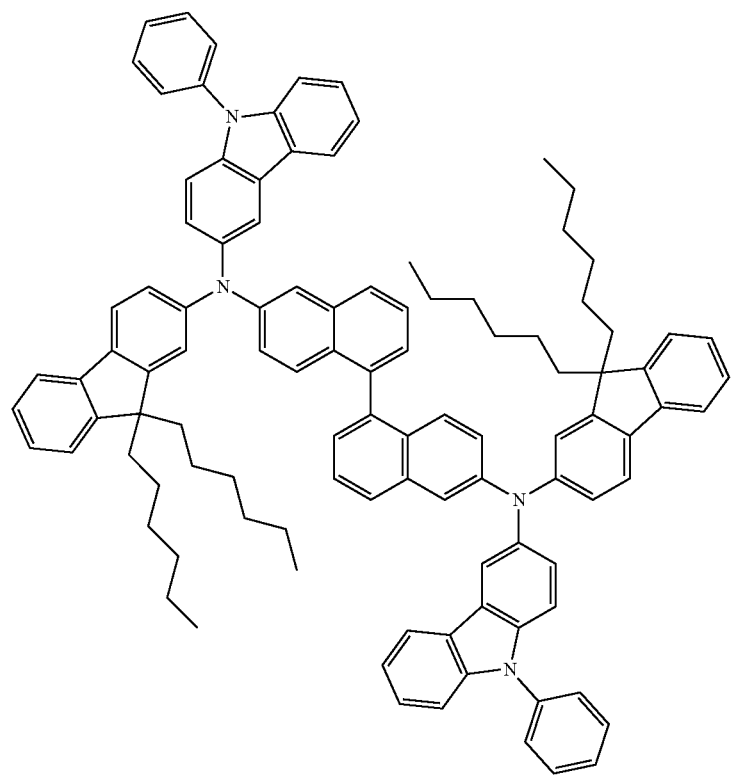
[H09]

-continued
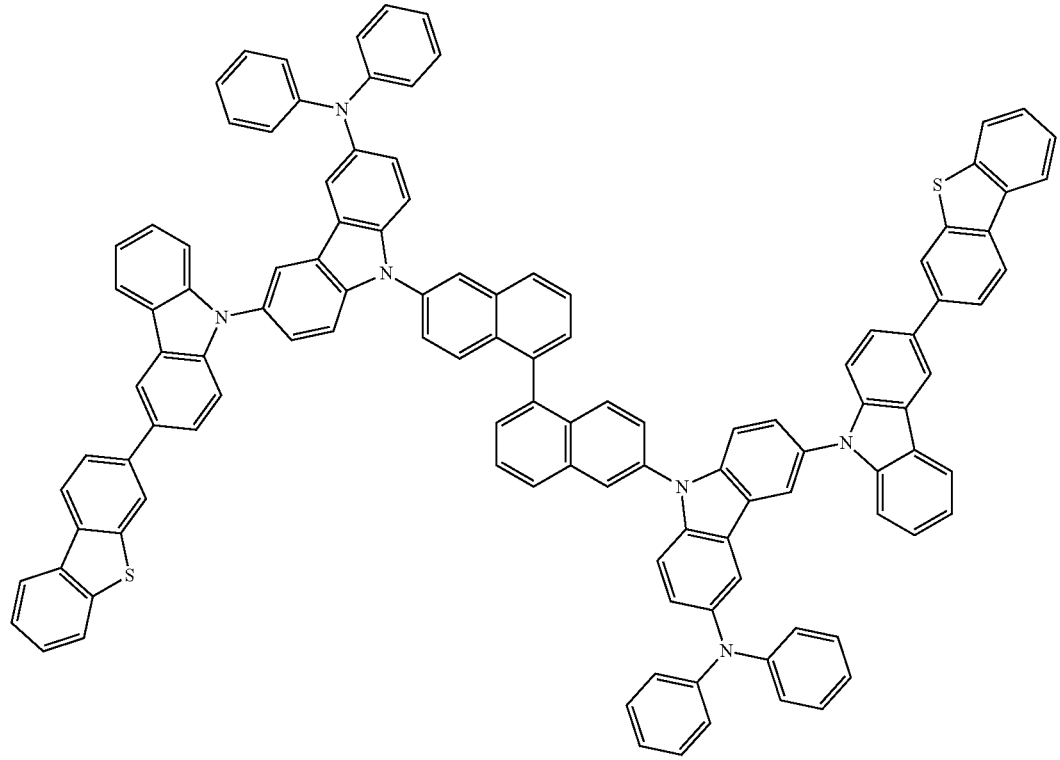
[H10]
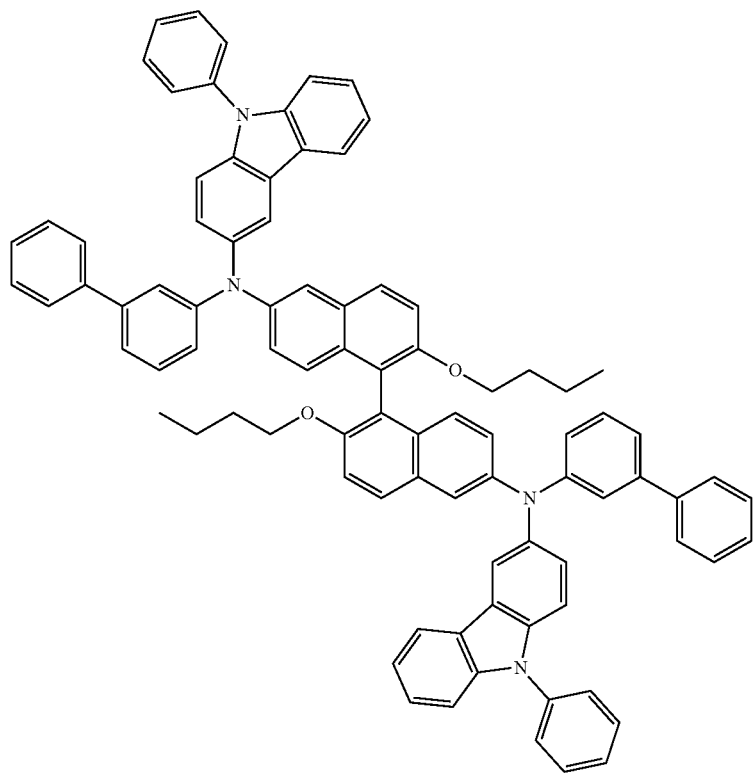
[H11]

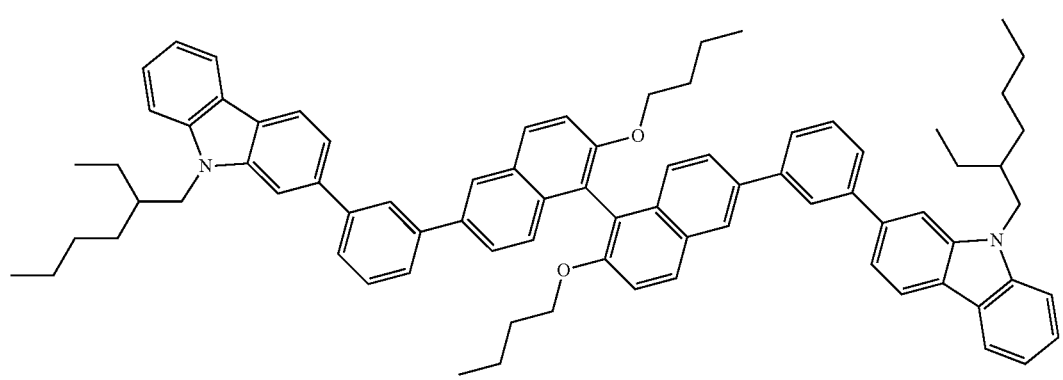
[H12]
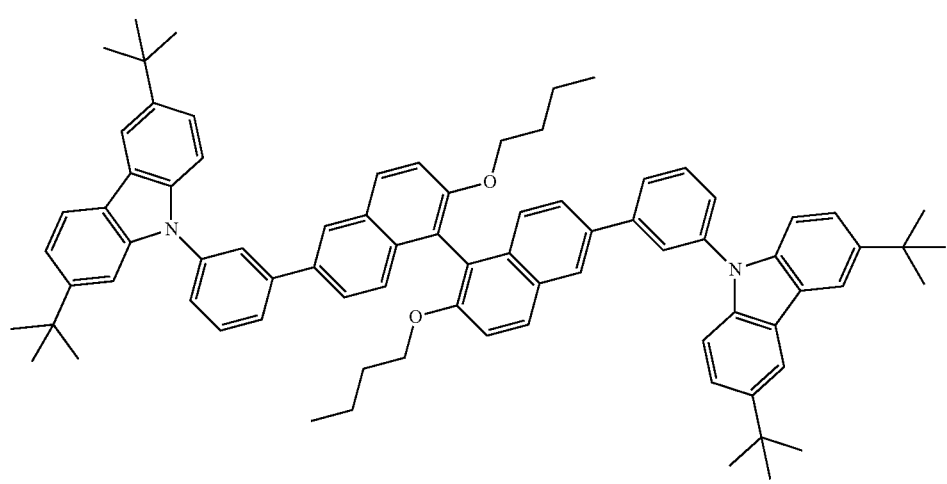
[H13]
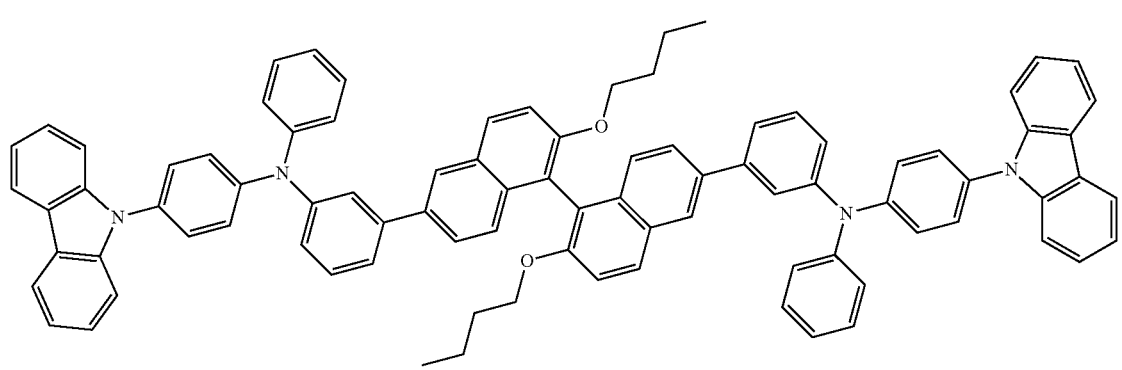
[H14]

-continued
[H15]
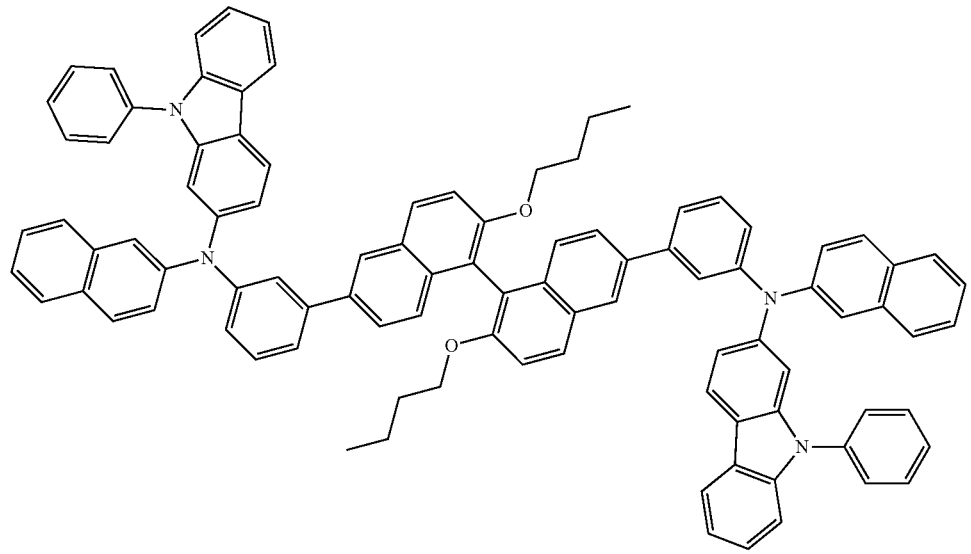
[H16]
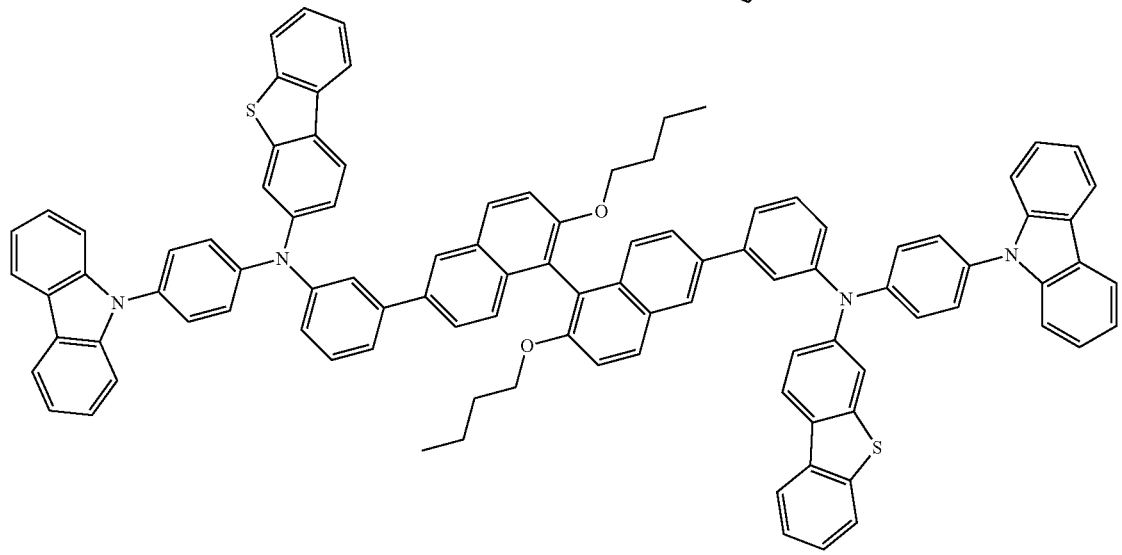
[H17]
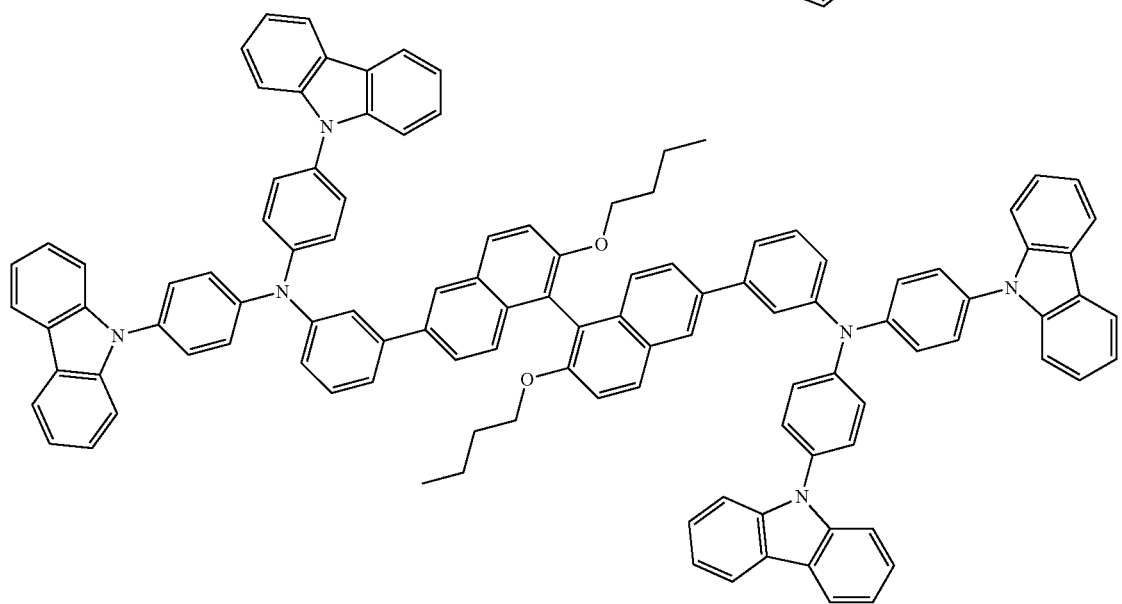

-continued
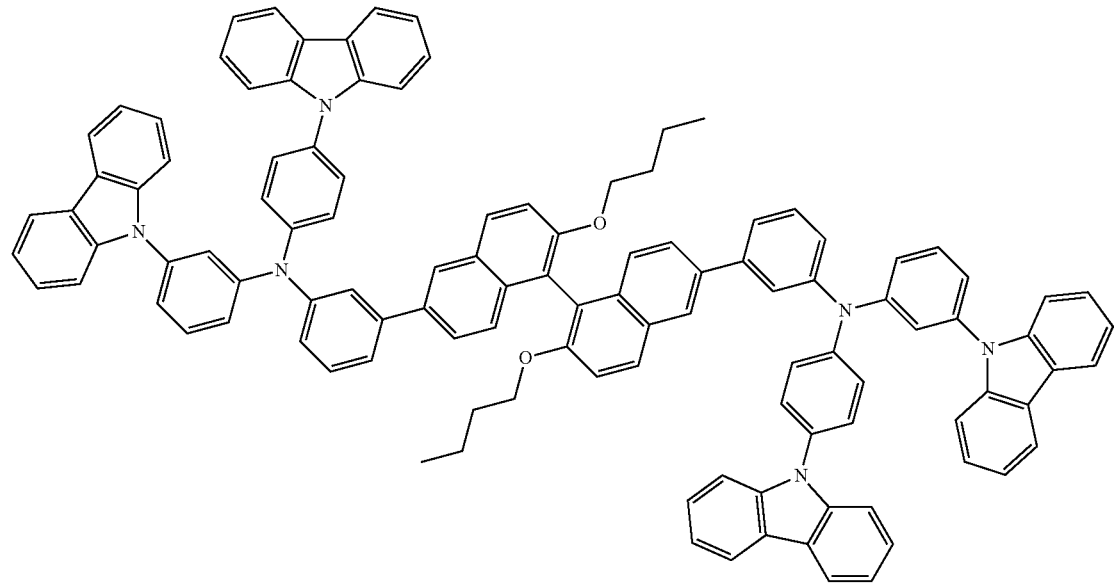
[H18]
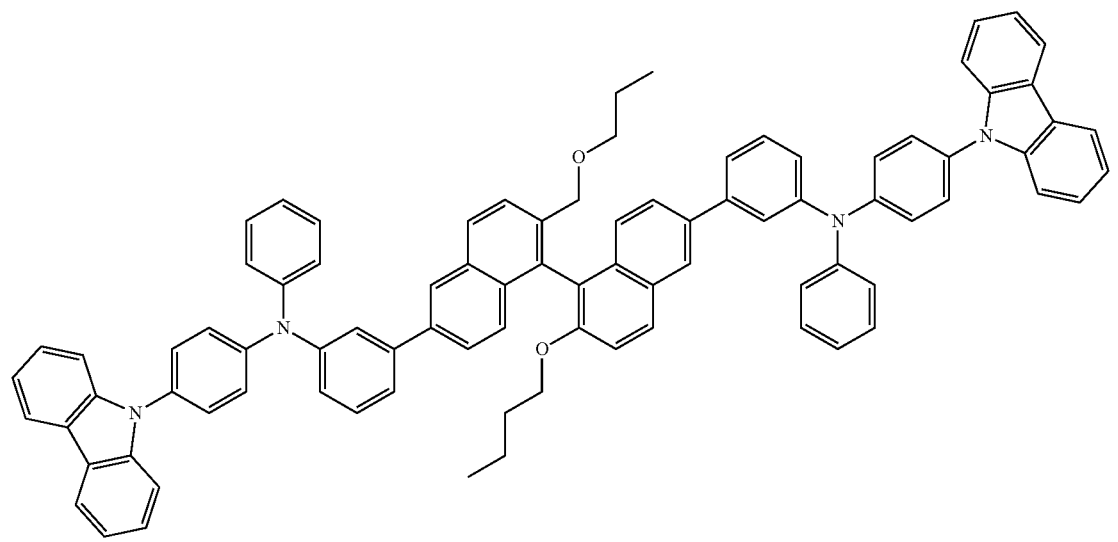
[H19]
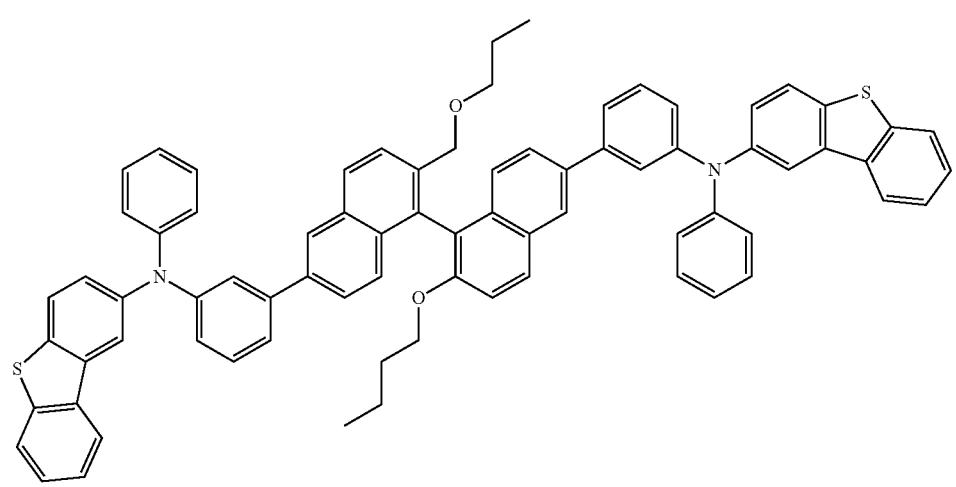
[H20]

[H21]

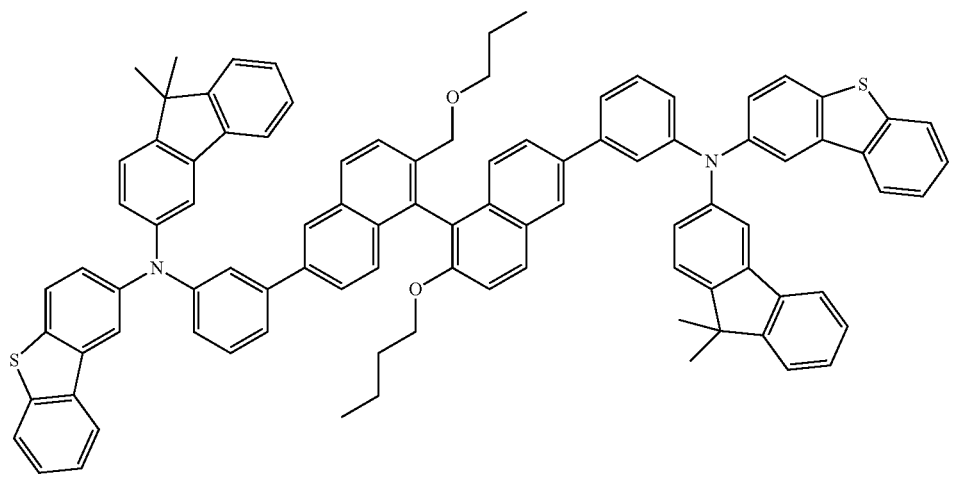

[H22]

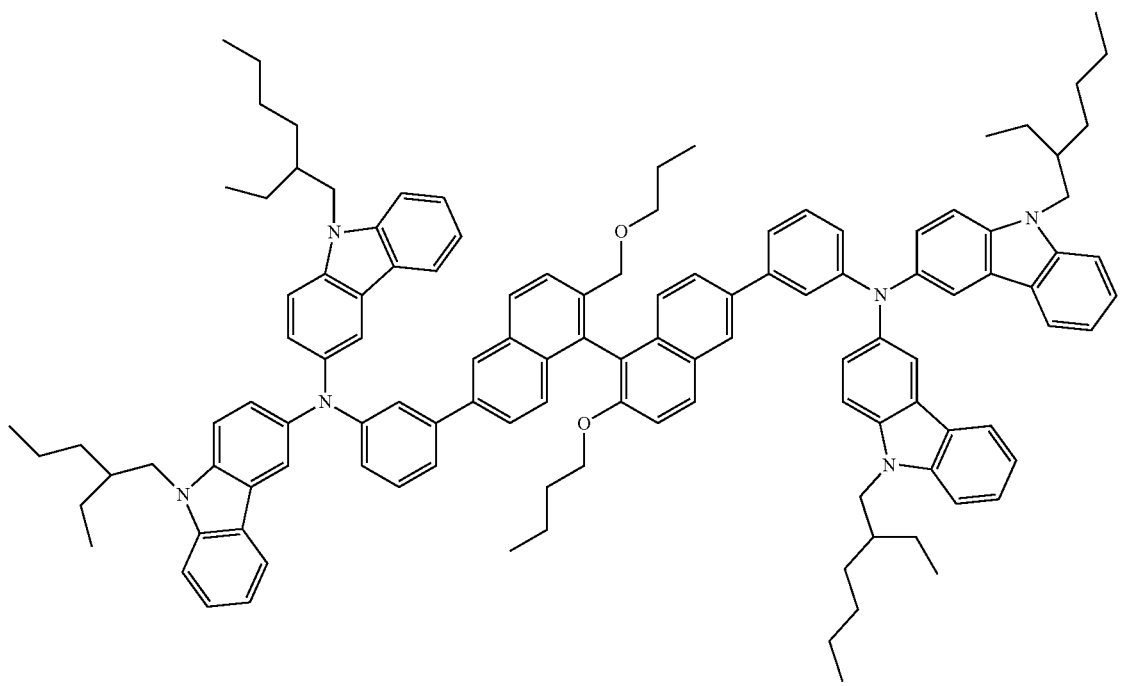

Light Emitting Diode and Light Emitting Device

The organic compound having the structure of anyone in Chemical Formulae 1 to 4 has a low HOMO energy level and is excellent in hole mobility, and can be laminated by using a solution process, so that the organic compound can be applied to a light emitting diode. The light emitting diode having the organic compound having the structure of anyone in Chemical Formulae 1 to 4 may be applied to a light emitting device such as a light emitting display device and a light emitting illumination device. FIG. 1 is a schematic cross-sectional view illustrating a light emitting display device of the present disclosure.

As illustrated in FIG. 1, a light emitting display device 100 includes a substrate 102, a thin film transistor Tr over the substrate 102 and a light emitting diode 200 connected to the thin film transistor Tr. The thin film transistor Tr includes a semiconductor layer 110, a gate electrode 130, a source electrode 152 and a drain electrode 154.

The substrate 102 may include, but are not limited to, glass, thin flexible material and/or polymer plastics. For example, the flexible material may be selected from the group, but are not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the light emitting diode 200 are arranged, forms an array substrate.

A buffer layer 104 may be disposed over the substrate 102, and the thin film transistor Tr is disposed over the buffer layer 104. The buffer layer 104 may be omitted.

A semiconductor layer 110 is disposed over the buffer layer 104. In one exemplary aspect, the semiconductor layer 110 may include, but are not limited to, oxide semiconductor materials. In this case, a light-shied pattern (not shown) may be disposed under the semiconductor layer 110, and the light-shield pattern (not shown) can prevent light from being incident toward the semiconductor layer 110, and thereby preventing the semiconductor layer 110 from being deteriorated by the light. Alternatively, the semiconductor layer 110 may include polycrystalline silicon. In this case, opposite edges of the semiconductor layer 110 may be doped with impurities.

A gate insulating layer 120 made of insulating material is disposed on the semiconductor layer 110. The gate insulating layer 120 may include, but are not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 may be patterned identically as the gate electrode 130.

An interlayer insulating layer 140 made of an insulating material is disposed on the gate electrode 130 with covering over an entire surface of the substrate 102. The interlayer insulating layer 140 may include, but are not limited to, an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over both sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, each of which includes a conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and source and drain electrodes are disposed over the semiconductor layer. In this case, the semiconductor layer may include, but are not limited to, amorphous silicon.

Although not shown in FIG. 1, a gate line and a data line, which cross each other to define a pixel region, and a switching element, which is connected to the gate line and the data line, may be further formed in the pixel region. The switching element is connected to the thin film transistor Tr, which is a driving element. Besides, a power line is spaced apart in parallel from the gate line or the data line, and the thin film transistor Tr may further includes a storage capacitor configured to constantly keep a voltage of the gate electrode for one frame.

In addition, the light emitting display device 100 may include a color filter (not shown) for absorbing a light emitted from the organic light emitting diode 200. For example, the color filter (not shown) may absorb a light of specific wavelength such as red (R), green (G) or blue (B). In this case, the light emitting display device 100 can implement full-color through the color filter (not shown).

For example, when the light emitting display device 100 is a bottom-emission type, the color filter (not shown) may be disposed on the interlayer insulating layer 140 with corresponding to the light emitting diode 200. Alternatively, when the light emitting display device 100 is a top-emission type, the color filter (not shown) may be disposed over the light emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 154, it may be spaced apart from the second semiconductor layer contact hole 154.

The light emitting diode 200 includes a first electrode 210 that is disposed on the passivation layer 160 and connected to the drain electrode 154 of the thin film transistor Tr. The organic light emitting diode 200 further includes an emission layer 230 as an emitting unit and a second electrode 220 each of which is disposed sequentially on the first electrode 210.

The first electrode 210 is disposed in each pixel region. The first electrode 210 may be an anode and include a conductive material having relatively high work function value. For example, the first electrode 210 may include, but are not limited to, a doped or undoped metal oxide such as indium-tin-oxide (ITO), indium-zinc-oxide (IZO), indium-tin-zinc oxide (ITZO), indium-copper-oxide (ICO), tin oxide ($SnO_2$), indium oxide ($In_2O_3$), cadmium:zinc oxide (Cd:ZnO), fluorine:tin oxide ($F:SnO_2$), indium:tin oxide ($In:SnO_2$), gallium:tin oxide ($Ga:SnO_2$) or aluminum:zinc oxide (Al:ZnO; AZO). Optionally, the first electrode 210 may include a metal or nonmetal material such as nickel (Ni), platinum (Pt), gold (Au), silver (Ag), iridium (Ir) or a carbon nanotube (CNT), other than the above-described metal oxide.

In one exemplary aspect, when the light emitting display device 100 is a top-emission type, a reflective electrode or a reflective layer (not shown) may be disposed under the first electrode 210. For example, the reflective electrode or the reflective layer (not shown) may comprise, but are not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

An emission layer 230 as an emitting unit is disposed on the first electrode 210. In one exemplary aspect, the emission layer 230 may have a mono-layered structure of an emitting material layer. Alternatively, the emission layer 230 may have a multiple-layered structure of a first charge transfer layer 340, 440 540 or 640, an emitting material layer 350, 450, 550 or 650 and a second charge transfer layer 360, 460, 560 or 660 as illustrated in FIGS. 2, 5, 6 and 8. In one exemplary aspect, the organic compound having the structure of anyone in Chemical Formulae 1 to 4 may be induced into the first charge transfer layer 340 or 440, or the second charge transfer layer 560 or 660. The configuration and locations of those layers in the emissive layer 230 will be explained in more detail below.

The second electrode 220 is disposed over the substrate 102 above which the emission layer 230 is disposed. The second electrode 220 may be disposed over a whole display area, may include a conductive material having a relatively low work function value compared to the first electrode 210, and may be a cathode. For example, the second electrode 220 may include, but are not limited to, Ca, Ba, Ca/Al, LiF/Ca, LiF/Al, BaF$_2$/Al, CsF/Al, CaCO$_3$/Al, BaF$_2$/Ca/Al, Al, Mg, Au:Mg or Ag:Mg.

In addition, an encapsulation film 180 may be disposed over the second electrode 220 in order to prevent outer moisture from penetrating into the light emitting diode 200. The encapsulation film 180 may have, but are not limited to, a laminated structure of a first inorganic insulating film 182, an organic insulating film 184 and a second inorganic insulating film 186.

Figure 2:
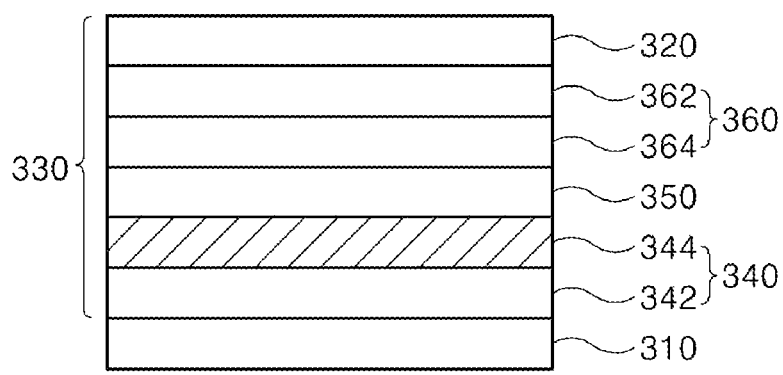
FIG. 2 is a schematic cross-sectional view illustrating a light emitting diode having a normal structure in accordance with an exemplary aspect of the present disclosure.

FIG. 2 is a schematic cross-sectional view illustrating a light emitting diode having a normal structure in accordance with an exemplary aspect of the present disclosure. As illustrated in FIG. 2, the light emitting diode (LED) 300 in accordance with the first aspect of the present disclosure include a first electrode 310, a second electrode 320 facing the first electrode 310 and an emission layer 330 disposed between the first and second electrodes 310 and 320. The emission layer 330 as an emitting unit includes an emitting material layer (EML) 350 disposed between the first and second electrodes 310 and 320, a first charge transfer layer (CTL1) 340 disposed between the first electrode 310 and the EML 350 and a second charge transfer layer (CTL2) 360 disposed between the EML 350 and the second electrode 320.

The first electrode 310 may be an anode such as a hole injection electrode. The first electrode 310 may be located over a substrate (not shown in FIG. 2) that may be a glass or a polymer. As an example, the first electrode 310 may include, but are not limited to, a doped or undoped metal oxide such as indium-tin-oxide (ITO), indium-zinc-oxide (IZO), indium-tin-zinc oxide (ITZO), indium-copper-oxide (ICO), tin oxide (SnO$_2$), indium oxide (In$_2$O$_3$), cadmium: zinc oxide (Cd:ZnO), fluorine:tin oxide (F:SnO$_2$), indium: tin oxide (In:SnO$_2$), gallium:tin oxide (Ga:SnO$_2$) or aluminum:zinc oxide (Al:ZnO; AZO). Optionally, the first electrode 210 may include a metal or nonmetal material such as nickel (Ni), platinum (Pt), gold (Au), silver (Ag), iridium (Ir) or a carbon nanotube (CNT), other than the above-described metal oxide.

The second electrode 320 may be a cathode such as an electron injection electrode. As an example, the second electrode 320 may include, but are not limited to, Ca, Ba, Ca/Al, LiF/Ca, LiF/Al, BaF$_2$/Al, CsF/Al, CaCO$_3$/Al, BaF$_2$/Ca/Al, Al, Mg, Au:Mg or Ag:Mg. As an example, each of the first electrode 310 and the second electrode 320 may have a thickness of, but are not limited to, about 5 to about 300 nm, and alternatively about 10 nm to about 200 nm.

In one exemplary aspect, when the LED 300 is a bottom emission-type LED, the first electrode 310 may include, but are not limited to, a transparent conductive metal oxide such as ITO, IZO, ITZO or AZO, and the second electrode 320 may include, but are not limited to, Ca, Ba, Ca/Al, LiF/Ca, LiF/Al, BaF$_2$/Al, Al, Mg, or an Ag:Mg alloy.

The CTL1 340 is disposed between the first electrode 310 and the EML 350. In this exemplary aspect, the CTL1 340 may be a hole transfer layer that provides holes into the EML 350. As an example, the CTL1 340 may include a hole injection layer (HIL) 342 disposed adjacently to the first electrode 310 between the first electrode 310 and the EML 350, and a hole transport layer (HTL) 344 disposed adjacently to the EML 350 between the first electrode 310 and the EML 350.

The HIL 342 facilitates holes injection from the first electrode 310 into the EML 350. As an example, the HIL 342 may include, but are not limited to, an organic material selected from the group consisting of poly(ethylenedioxythiophene):polystyrenesulfonate (PEDOT:PSS); 4,4',4"-tris(diphenylamino)triphenylamines (TDATA) doped with tetrafluoro-tetracyano-quinodimethane (F4-TCNQ); p-doped phthalocyanine such as zinc phthalocyanine (ZnPc) doped with F4-TCNQ; N,N'-diphenyl-N,N'-bis(1-naphthyl)-1,1'-biphenyl-4,4"-diamine (α-NPD) doped with F4-TCNQ; hexaazatriphenylene-hexanitrile (HAT-CN); and a combination thereof. As an example, the HIL 342 may include the dopant such as F4-TCNQ about 1 to about 30% by weight. The HIL 342 may be omitted in compliance with a structure of the LED 300.

The HTL 344 transports holes from the first electrode 310 into the EML 350. The HTL 344 may include an organic compound having the structure of anyone in Chemical Formulae 1 to 4. When the organic compound having the structure of anyone in Chemical Formulae 1 to 4 is induced into the HTL 344, holes and electrons can be injected into the EML 350 in a balanced manner.

In FIG. 2, while the CTL1 340 as a hole transfer layer is divided into the HIL 342 and the HTL 344, the CTL1 340 may have a mono-layered structure. For example, the CTL1 340 may include only the HTL 344 without the HIL 342 or may include the above-mentioned hole transporting material doped with the hole injection material (e.g. PEDOT:PSS).

The CTL1 340 including the HIL 342 and the HTL 344 may be laminated by any vacuum deposition process such as vacuum vapor deposition and sputtering, or by any solution process such as spin coating, drop coating, dip coating, spray coating, roll coating, flow coating, casting, screen printing and inkjet printing, or a combination thereof. For example, each of the HIL 342 and the HTL 344 may have a thickness, but are not limited to, between about 10 nm and 200 nm, and alternatively about 10 nm and 100 nm.

The EML 350 may include inorganic luminescent particles or organic luminescent material. As an example, the EML 350 may include inorganic luminescent particles such as quantum dots (QDs) or quantum rods (QRs). QDs or QRs are inorganic luminescent particles that emit light as unstable stated excitons drop from conduction band to valence band.

These inorganic luminescent particles have very large extinction coefficient, high quantum yield among inorganic particles and generates strong fluorescence. In addition, these inorganic luminescent particles shows different luminescence wavelengths as its sizes, it is possible to emit lights within the whole visible light spectra so as to implement various colors by adjusting sizes of these inorganic luminescent particles. When these inorganic luminescent particles such as QDs and/or QRs are used as a luminous material in the EML 350, it is possible to enhance color purity in individual pixel region and realize White (W) light consisting of red (R), green (G) and blue (B) lights having high color purity.

In one exemplary aspect, QDs or QRs may have a single-layered structure. In another exemplary aspect, QDs or QRs may have a multiple-layered heterologous structure, i.e. core/shell structure. In this case, each of the core and the shell may have single layer or multiple layers, respectively. The reactivity of precursors, which can be synthesized to the core and/or the shell, injection rates of the precursors into a reaction vessel, reaction temperature and kinds of ligands bonded to an outer surface of those inorganic luminescent particles such as QDs or QRs may have affect upon the growth rates and crystal structures of those inorganic luminescent particles. As a result, it is possible to emit lights of various luminescent wavelength ranges, as the energy level bandgap of those inorganic luminescent particles are adjusted.

In one exemplary aspect, inorganic luminescent particles (e.g. QDs and/or QRs) may have a type I core/shell structure where an energy level bandgap of the core is within an energy level bandgap of the shell. In case of using the type I core/shell structure, electrons and holes are transferred to the core and recombined in the core. Since the core emits light from exciton energies, it is possible to adjust luminance wavelengths by adjusting sizes of the core.

In another exemplary aspect, the inorganic luminescent particles (e.g. QDs and/or QRs) may have a type II core/shell structure where the energy level bandgap of the core and the shell are staggered and electrons and holes are transferred to opposite directions among the core and the shell. In case of using the type II core/shell structure, it is possible to adjust luminescence wavelengths as the thickness and the energy bandgap locations of the shell.

In still another exemplary aspect, the inorganic luminescent particles (e.g. QDs and/or QRs) may have a reverse type I core/shell structure where the energy level bandgap of the core is wider than the energy level bandgap of the shell. In case of using the reverse type I core/shell structure, it is possible to adjust luminescence wavelengths as thickness of the shell.

As an example, when the inorganic luminescent particle (e.g. QDs and/or QRs) has a type-I core/shell structure, the core is a region where luminescence substantially occurs, and a luminescence wavelength of the inorganic luminescent particle is determined as the sizes of the core. To achieve a quantum confinement effect, the core necessarily has a smaller size than the exciton Bohr radius according to material of the inorganic luminescent particle, and an optical bandgap at a corresponding size.

The shell of the inorganic luminescent particles (e.g. QDs and/or QRs) promotes the quantum confinement effect of the core, and determines the stability of the particles. Atoms exposed on a surface of colloidal inorganic luminescent particles (e.g. QDs and/or QRs) having only a single structure have lone pair electrons which do not participate in a chemical bond, unlike the internal atoms. Since energy levels of these surface atoms are between the conduction band edge and the valence band edge of the inorganic luminescent particles (e.g. QDs and/or QRs), the charges may be trapped on the surface of the inorganic luminescence particles (e.g. QDs and/or QRs), and thereby resulting in surface defects. Due to a non-radiative recombination process of excitons caused by the surface defects, the luminous efficiency of the inorganic luminescence particles may be degraded, and the trapped charges may react with external oxygen and compounds, leading to a change in the chemical composition of the inorganic luminescence particles, or to a permanent loss of the electrical/optical properties of the inorganic luminescent particles.

To effectively form the shell on the surface of the core, a lattice constant of the material in the shell needs to be similar to that of the material in the core. As the surface of the core is enclosed by the shell, the oxidation of the core may be prevented, the chemical stability of the inorganic luminescence particles (e.g. QDs and/or QRs) may be enhanced, and the photo-degradation of the core by an external factor such as water or oxygen may be prevented. In addition, the loss of excitons caused by the surface trap on the surface of the core may be minimized, and the energy loss caused by molecular vibration may be prevented, thereby enhancing the quantum efficiency.

In one exemplary aspect, each of the core and the shell may include, but are not limited to, a semiconductor nanocrystals and/or metal oxide nanocrystals having quantum confinement effect. For example, the semiconductor nanocrystals of the core and the shell may be selected from the group, but are not limited to, consisting of Group II-VI compound semiconductor nanocrystals, Group III-V compound semiconductor nanocrystals, Group IV-VI compound semiconductor nanocrystals, Group I-III-VI compound semiconductor nanocrystals and combination thereof.

Particularly, Group II-VI compound semiconductor nanocrystals of the core and/or the shell may be selected from the group, but are not limited to, consisting of MgS, MgSe, MgTe, CaS, CaSe, CaTe, SrS, SrSe, SrTe, BaS, BaSe, BaTe, ZnS, ZnSe, ZnTe, ZnSeS, ZnTeSe, ZnO, CdS, CdSe, CdTe, CdSeS, CdZnS, CdSeTe, CdO, HgS, HgSe, HgTe, CdZnTe, HgCdTe, HgZnSe, HgZnTe, CdS/ZnS, CdS/ZnSe, CdSe/ZnS, CdSe/ZnSe, ZnSe/ZnS, ZnS/CdSZnS, CdS/CdZnS/ZnS, ZnS/ZnSe/CdSe and combination thereof.

Group III-V compound semiconductor nanocrystals of the core and/or shell may be selected from the group, but are not limited to, consisting of AN, AlP, AlAs, AlSb, GaN, GaP, $Ga_2O_3$, GaAs, GaSb, InN, $In_2O_3$, InP, InAs, InSb, AlGaAs, InGaAs, InGaP, AlInAs, AlInSb, GaAsN, GaAsP, GaAsSb, AlGaN, AlGaP, InGaN, InAsSb, InGaSb, AlGaInP, AlGaAsP, InGaAsP, InGaAsSb, InAsSbP, AlInAsP, AlGaAsN, InGaAsN, InAlAsN, GaAsSbN, GaInNAsSb and combination thereof.

Group IV-VI compound semiconductor nanocrystals of the core and/or shell may be selected from the group, but are not limited to, consisting of $TiO_2$, $SnO_2$, SnS, $SnS_2$, SnTe, PbO, $PbO_2$, PbS, PbSe, PbTe, PbSnTe and combination thereof. Also, Group I-III-VI compound semiconductor nanocrystals of the core and/or shell may be selected from the group, but are not limited to, $AgGaS_2$, $AgGaSe_2$, $AgGaTe_2$, $AgInS_2$, $CuInS_2$, $CuInSe_2$, $Cu_2SnS_3$, $CuGaS_2$, $CuGaSe_2$ and combination thereof. Alternatively, each of the core and the shell may independently include multiple layers each of which has different Groups compound semiconductor nanocrystals, e.g., Group II-VI compound semiconductor nanocrystals and Group III-V compound semiconductor nanocrystals such as InP/ZnS, InP/ZnSe, GaP/ZnS, and the likes, respectively.

In another aspect, the metal oxide nanocrystals of the core and/or shell may include, but are not limited to, Group II or Group III metal oxide nanocrystals. As an example, the metal oxide nanocrystals of the core and/or the shell may be selected from the group, but are not limited to, MgO, CaO, SrO, BaO, $Al_2O_3$ and combination thereof.

The semiconductor nanocrystals of the core and/or the shell may be doped with a rare earth element such as Eu, Er, Tb, Tm, Dy or an arbitrary combination thereof or may be doped with a transition metal element such as Mn, Cu, Ag, Al or an arbitrary combination thereof.

As an example, the core in QDs or QRs may include, but are not limited to, ZnSe, ZnTe, CdSe, CdTe, InP, ZnCdS, $Cu_xIn_{1-x}S$, $Cu_xIn_{1-x}Se$, $Ag_xIn_{1-x}S$ and combination thereof. The shell in QDs or QRs may include, but are not limited to, ZnS, GaP, CdS, ZnSe, CdS/ZnS, ZnSe/ZnS, ZnS/ZnSe/CdSe, GaP/ZnS, CdS/CdZnS/ZnS, ZnS/CdSZnS, $Cd_xZn_{1-x}S$ and combination thereof.

In another exemplary aspect, the inorganic luminescent particle may include, but are not limited to, alloy QD or alloy QR such as homogenous alloy QD or QR or gradient alloy QD or QR, e.g. $CdS_xSe_{1-x}$, $CdSe_xTe_{1-x}$, $Cd_xZn_{1-x}S$, $Zn_xCd_{1-x}Se$, $Cu_xIn_{1-x}S$, $Cu_xIn_{1-x}Se$, $Ag_xIn_{1-x}S$.

When the EML 350 includes inorganic luminescent particles such as QDs and/or QRs, the EML 350 may be laminated through any solution process, i.e. coating the dispersion solution, which contains inorganic luminescent particles dissolved in a solvent, on the CTL1 340, for example the HTL 344, and evaporating the solvent. In one aspect, the EML 350 may be laminated on the CTL1 340 using any solution process such as spin coating, drop coating, dip coating, spray coating, roll coating, flow coating, casting, screen printing and inkjet printing, or a combination thereof.

In one exemplary aspect, the EML 350 may include inorganic luminescent particles such as QDs and/or QRs having photoluminescence (PL) wavelength peaks of 440 nm, 530 nm, and 620 nm so as to realize white LED. Optionally, the EML 350 may include inorganic luminescent particles such as QDs or QRs having any one of red, green and blue colors, and may be formed to emit any one color.

In an alternative aspect, the EML 350 may include an organic luminous material. The organic luminous material is not limited to specific organic luminous material. As an example, the EML 350 may include an organic luminous material that emits red (R), green (G) or blue (B) light, and may include fluorescent material or phosphorescent material. As an example, the organic luminous material in the EML 350 may include a host and a dopant. When the organic luminous material constitutes a host-dopant system, the EML 350 may include the dopant, but are not limited to, about 1 to about 50% by weight, and alternatively about 1 to about 30% by weight.

The organic host, which can be used in the EML 350, is not limited to specific organic luminous material. As an example, the organic host in the EML 350 may include, but are not limited to, Tris(8-hydroxyquinoline)aluminum ($Alq_3$), TCTA, PVK, 4,4'-bis(N-carbazolyl)-1,1'-biphenyl (CBP), 4,4'-Bis(9-carbazolyl)-2,2'-dimethylbiphenyl (CDBP), (9,10-di(naphthalene-2-yl)anthracene (ADN), 3-tert-butyl-9,10-di(naphtha-2-yl)anthracene (TB ADN), 2-methyl-9,10-bis(naphthalene-2-yl) anthracene (MADN), 1,3,5-tris(N-phenylbenzimidazole-2-yl)benzene (TPBi), distyrylarylene (DSA), mCP and/or 1,3,5-tris(carbazol-9-yl)benzene (TCP).

In one exemplary aspect, when the EML 350 emits red light, the dopant in the EML 350 may include, but are not limited to, an organic compound and/or a metal complex such as 5,6,11,12-tetraphenylnaphthalene (Rubrene), (Bis(2-benzo-thiophene-2-yl-pyridine)(acetylacetonate)iridium (III) ($Ir(btp)_2(acac)$), Bis[1-(9,9-dimethyl-9H-fluorn-2-yl)-isoquinoline](acetylacetonate)iridium(III) ($Ir(fliq)_2(acac)$), Bis[2-(9,9-dimethyl-9H-fluorn-2-yl)-quinoline](acetylacetonate)iridium(III) ($Ir(flq)_2(acac)$), Bis-(2-phenylquinoline)(2-(3-methylphenyl)pyridinate)irideium(III) ($Ir(phq)_2typ$) and/or Iridium(III)bis(2-(2,4-difluorophenyl)quinoline)picolinate (FPQIrpic).

In another exemplary aspect, when the EML 350 emits green light, the dopant in the EML 350 may include, but are not limited to, an organic compound and/or a metal complex such as N,N'-dimethyl-quinacridone (DMQA), coumarine 6,9,10-bis[N,N-di-(p-tolyl)amino]anthracene (TTPA), 9,10-bis[phenyl(m-tolyl)-amino]anthracene (TPA), bis(2-phenylpyridine)(acetylacetonate)iridium(III) ($Ir(ppy)_2(acac)$), fac-tris(phenylpyridine)iridium(III) (fac-$Ir(ppy)_3$) and/or tris[2-(p-tolyl)pyridine]iridium(III) ($Ir(mppy)_3$).

In still another exemplary aspect, when the EML 350 emits blue right, the dopant in the EML 350 may include, but are not limited to, an organic compound and/or a metal complex such as 4,4'-bis[4-(di-p-tolylamino)styryl]biphenyl (DPAVBi), perylene, 2,5,8,11-tetra-tert-butylpherylene (TBPe), bis(3,5-difluoro-2-(2-pyridyl)phenyl-(2-carbozylpyridyl)iridium(III) (FirPic), mer-tris(1-phenyl-3-methylimidazolin-2ylidene-C,C2') iridium(DI (mer-$Ir(pmi)_3$) and/or tris(2-(4,6-difluorophenyl)pyridine)iridium (III) ($Ir(Fppy)_3$).

Alternatively, when the EML 350 includes an organic luminous material, the EML 350 may include a delayed fluorescent material.

When the EML 350 includes an organic luminous material, the EML 350 may be laminated by any vacuum deposition process such as vacuum vapor deposition and sputtering, or by any solution process such as spin coating, drop coating, dip coating, spray coating, roll coating, flow coating, casting, screen printing and inkjet printing, or a combination thereof.

For example, the EML 350 may have a thickness, but are not limited to, between about 5 nm and about 300 nm, and alternatively about 10 nm and about 200 nm.

In accordance with an exemplary aspect, the EML 350 may include inorganic luminescent particles such as QDs and/or QRs. Even if the LED 300 has high luminance by increasing current density or driving voltage, the inorganic luminescent particles are not degraded, so that the life span of the LED 300 may not be reduced.

The CTL2 360 is disposed between the EML 350 and the second electrode 320. The CTL2 360 may be an electron transfer layer which provides electrons into the EML 350. In one exemplary aspect, the CTL2 360 may include an electron injection layer (EIL) 362 disposed adjacently to the second electrode 320 between the second electrode 320 and the EML 350, and an electron transport layer (ETL) 364 disposed adjacently to the EML 350 between the second electrode 320 and the EML 350.

The EIL 362 facilitates the injection of electrons from the second electrode 320 into the EML 350. For example, the EIL 362 may include, but are not limited to, a metal such as Al, Cd, Cs, Cu, Ga, Ge, In and/or Li, each of which is undoped or doped with fluorine; and/or metal oxide such as titanium dioxide ($TiO_2$), zinc oxide (ZnO), zirconium oxide (ZrO), tin oxide ($SnO_2$), tungsten oxide ($WO_3$) and/or tantalum oxide ($Ta_2O_3$), each of which is undoped or doped with Al, Mg, In, Li, Ga, Cd, Cs or Cu.

The ETL 364 transfers electrons into the EML 350. The ETL 364 may include inorganic and/or organic materials. In one exemplary aspect, when the EML 350 includes inorganic luminescent particles, the ETL 364 may include an inorganic material so as to prevent an interface defect from being formed at an interface between the EML 350 and the ETL 364, and thereby securing driving stability of the LED 300. When the ETL 364 includes an inorganic material having high charge mobility, the electron transport rate provided from the second electrode 320 may be improved, and electrons can be transported efficiently into the EML 350 owing to high electron levels or concentrations.

In addition, when the EML 350 includes an inorganic luminescent particle, the inorganic luminescent particle in the EML 350 typically has a very deep valence band (VB) energy level, which corresponds to a highest occupied molecular orbital (HOMO) energy level of an organic material, compared to a HOMO energy level of an organic luminous material. An organic compound having electron transporting property typically has a shallower HOMO energy level than the VB energy level of the inorganic luminescent particle. In this case, the holes, injected from the first electrode 310 into the EML 350 having the inorganic luminescent particles, may be leaked toward the second electrode via the ETL 364 including the organic compound as an electron transporting material.

In one exemplary aspect, the ETL 364 may include an inorganic material having relatively deep VB energy level compared to VB energy level or HOMO energy level of the luminous material in the EML 350. As an example, an inorganic material having wide energy level bandgap (Eg) between the VB energy level and a conduction band energy level, which corresponds to a lowest unoccupied molecular orbital (LUMO) energy level of an organic compound, may be used as an electron transporting material of the ETL 364. In this case, the holes, injected from the first electrode 310 into the EML 350 having the inorganic luminescent particles, cannot be leaked to the ETL 364, and electrons provided from the second electrode 320 can be injected efficiently into the EML 350.

As an example, when the ETL 364 includes an inorganic material, the ETL 364 may include, but are not limited to, a metal oxide undoped or doped with at least one of Al, Mg, In, Li, Ga, Cd, Cs and Cu; a semiconductor particle undoped or doped with at least one of Al, Mg, In, Li, Ga, Cd, Cs and Cu; metal nitrides; and combination thereof.

In one exemplary aspect, the metal component of the metal oxide in the ETL 364 may be selected from, but are not limited to, zinc (Zn), calcium (Ca), magnesium (Mg), titanium (Ti), tin (Sn), tungsten (W), tantalum (Ta), hafnium (Hf), aluminum (Al), zirconium (Zr), barium (Ba) and combination thereof. Particularly, the metal oxide in the ETL 364 may include, but are not limited to, titanium dioxide ($TiO_2$), zinc oxide (ZnO), magnesium zinc oxide (ZnMgO), zirconium oxide (ZrO), tin oxide ($SnO_2$), tungsten oxide ($WO_3$), tantalum oxide ($Ta_2O_3$), hafnium oxide ($HfO_3$), aluminum oxide ($Al_2O_3$), barium titanium oxide ($BaTiO_3$), and barium zirconium oxide ($BaZrO_3$), each of which is undoped or doped with Al, Mg, In, Li, Ga, Cd, Cs or Cu.

Other inorganic material in the ETL 364 may include, but are not limited to, a semiconductor particle such as CdS, ZnSe, ZnS, each of which is undoped or doped with Al, Mg, In, Li, Ga, Cd, Cs or Cu; nitrides such as $Si_3N_4$; and combination thereof.

In another exemplary aspect, when the ETL 364 includes an organic material, the ETL 364 may include, but are not limited to, oxazole-based compounds, isooxazole-based compounds, triazole-based compounds, isotriazole-based compounds, oxadiazole-based compounds, thiadiazole-based compounds, phenanthroline-based compounds, perylene-based compound, benzoxazole-based compounds, benzothiazole-based compounds, benzimidazole-based compounds, triazine-based compounds and/or aluminum complexes. Particularly, the organic material of the ETL 364 may include, but are not limited to, 3-(biphenyl-4-yl)-5-(4-tertbutylphenyl)-4-phenyl-4H-1,2,4-triazole (TAZ), bathocuproine (2,9-dimethyl-4,7-diphenyl-1,10-phenanthroline; BCP), 2,2',2"-(1,3,5-Benzinetriyl)-tris(1-phenyl-1-H-benzimidazole) (TPBi), Tris(8-hydroxyquinoline)aluminum ($Alq_3$), Bis(2-methyl-8-quninolinato)-4-phenylphenolatealuminum(III) (Balq), bis(2-methyl-quinolinato)(tripnehylsiloxy) aluminum(III) (Salq) and combination thereof.

Similar to the CTL1 340, while FIG. 2 illustrates CTL2 360 as a bi-layered structure including the EIL 362 and the ETL 364, the CTL2 360 may have a mono-layered structure having only the ETL 364. Alternatively, the CTL2 360 may have a mono-layered structure of ETL 364 including a blend of the above-described electron-transporting inorganic material with cesium carbonate.

The CTL2 360, which includes the EIL 362 and/or the ETL 364, may be laminated on the EML 350 by any vacuum deposition process such as vacuum vapor deposition and sputtering, or by any solution process such as spin coating, drop coating, dip coating, spray coating, roll coating, flow coating, casting, screen printing and inkjet printing, or combination thereof. As an example, each of the EIL 362 and the ETL 364 may have a thickness, but are not limited to, between about 10 nm and about 200 nm, and alternatively about 10 nm and 100 nm.

For example, the LED 300 may have a hybrid charge transfer layer (CTL) in which the HTL 344 of the CTL1 340 includes the organic material as describe above and the CTL2 360, for example, the ETL 364 includes the inorganic material as described above. In this case, The LED 300 may enhance its luminous properties.

When holes are transported to the second electrode 320 through the EML 350, or electrons are transported to the first electrode 310 through the EML 350, the lifespan and efficiency of the LED 300 may be reduced. To prevent such deterioration, the LED 300 may further include at least one exciton blocking layer disposed adjacently to the EML 350.

For example, the LED 300 may include an electron blocking layer (EBL) capable of controlling and preventing the transfer of electrons between the HTL 344 and the EML 350. As an example, the EBL (not shown) may include, but are not limited to, TCTA, tris[4-diethylamino)phenyl] amine), N-(biphenyl-4-yl)-9,9-dimethyl-N-(4-(9-phenyl-9H-carbazole-3-yl)phenyl)-9H-fluorene-2-amine, tri-p-tolylamine, 1,1-bis(4-(N,N'-di(ptolyl)amino)phenyl) cyclohexane (TAPC), m-MTDATA, 1,3-bis(N-carbazolyl) benzene (mCP), 3,3'-bis(N-carbazolyl)-1,1'-biphenyl (mCBP), Poly-TPD, copper phthalocyanine (CuPc), DNTPD and/or 1,3,5-tris[4-diphenylamino)phenyl]benzene (TDAPB), and combination thereof.

In addition, a hole blocking layer (HBL), as a second exciton blocking layer, may be disposed between the EML 350 and the ETL 364 to prevent the transfer of holes between the EML 350 and the ETL 364. In one exemplary aspect, the HBL (not shown) may include, but are not limited to, oxadiazole-based compounds, triazole-based compounds, phenanthroline-based compounds, benzoxazole-based compounds, benzothiazole-based compounds, benzimidazole-based compounds, triazine-based compounds, and the likes, which may be used for the ETL 364. For example, the HBL (not shown) may include, but are not limited to, 2,9-dimethyl-4,7-diphenyl-1,10-phenanthroline (BCP), BAlq, Alq3, PBD, spiro-PBD and/or Liq, which have/has a deeper HOMO energy level than that of the material used for the EML 350.

As described above, the organic compound having the structure of anyone in Chemical Formulae 1 to 4 includes a fused aromatic ring having a binaphthyl core so that the organic compound shows a very deep or low HOMO energy level. In addition, since the organic compound includes at least one substituent having an excellent hole mobility property, the organic compound has enhanced hole transporting property. Accordingly, holes and electrons can be injected into the EML 350 in a balanced manner in the LED 300 including the organic compound.

Figure 3:
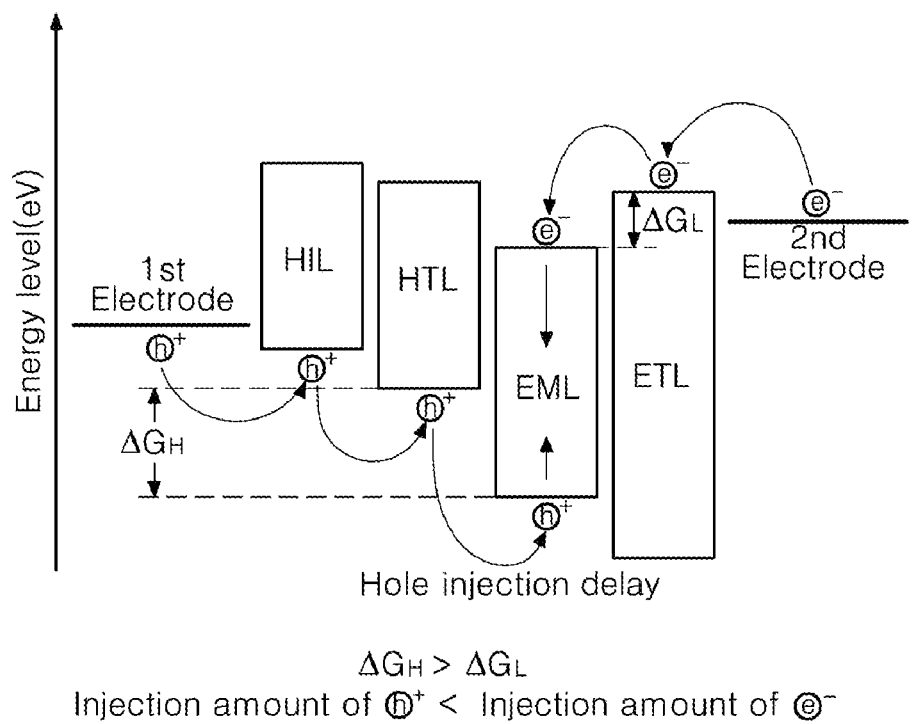
FIG. 3 is a schematic diagram illustrating energy levels among materials in an emissive layers between electrodes in the related art.

FIG. 3 is a schematic diagram illustrating energy levels among materials in an emissive layers between electrodes in the prior art. A light emitting diode is a device that emits light as charge carriers are injected into an EML, which includes a luminous material, between a hole injection electrode (first electrode) and an electron injection electrode (second electrode), and then those charge carriers such as electrons "e" and holes "h+" form excitons and then disappear. The holes "h+" injected from the first electrode and the electrons "e" injected from the second electrode are recombined with each other in the EML to from excitons. The energy, which is generated in the course of forming excitons, enables the luminous material in the EML to be excited state and can be emitted light energy form.

Both the HIL 342 and the HTL 344 inject and transport positive charge carriers, i.e. holes "h+" into the EML from the first electrode 310, and the ETL injects and transports negative charge carriers, i.e. electrons "e" into the EML 350 from the second electrode 320. Each layer in the emissive layer 330 must include material having appropriate energy level and energy level bandgap so as to inject or transport the holes "h+" and electrons "e" into the EML 350.

The luminous material of the EML has a lower or deeper HOMO energy level $HOMO_{EML}$ than a HOMO energy level $HOMO_{HTL}$ of the prior-art hole transporting material of the HTL. Particularly, when the EML 350 includes an inorganic luminescent particles such as QDs or QRs as a luminous material, the VB energy level $VB_{EML}$ of these inorganic luminescent particles, which corresponds to a HOMO energy level of the organic compounds, is much lower than a HOMO energy level of an organic luminous material.

In addition, the luminous material in the EML 350 has a high conduction band energy level $CV_{EML}$ (inorganic material) or Lowest Unoccupied Molecular Orbital (LUMO) energy level $LUMO_{EML}$. Accordingly, when the holes are transported from the HTL to the EML as well as when the electrons are transported from the ETL to the EML, energy barriers are formed between the EML and the HTL or ETL owing to energy level bandgap between the luminous material in the EML 350 and charge transporting materials in the charge transport layers HTL 344 and ETL 364 disposed adjacently to the EML 350.

However, the energy level bandgap "$\Delta G_H$" between the HOMO energy level $HOMO_{HTL}$ of the HTL 344 and the HOMO energy level HOMOEML of the EML 350 is much larger than the energy level bandgap "$\Delta G_L$" between the LUMO energy level $LUMO_{ETL}$ of the ETL 364 and the LUMO energy level $LUMO_{EML}$ of the EML 350. In other words, the luminous material of the EML 350 has a very lower HOMO energy level $HOMO_{EML}$ compared to the HOMO energy level $HOMO_{HTL}$ of the prior-art hole transporting materials in the HTL.

Accordingly, the holes transportations and injections into the EML are delayed compared to the electrons transportations injections into the EML, i.e., the holes "h+" are injected slowly than the electrons "e" into the EML. As a result, positive charged carriers, holes "h+" and negative charged carriers, electrons "e" cannot be injected into the EML in a balanced manner. Particularly, when the EML includes an inorganic luminescent material having very low valence band energy level $VB_{EML}$, the injection unbalance between holes "h++" and electrons "e" into the EML becomes more serious.

As excessive amount of electrons "e" are injected compared to an amount of holes "h+", a large amount of the excessively injected electrons "e" does not recombine with the holes "h+" and thus is quenched without forming excitons (electron quenching). As electrons "e" are injected into the EML excessively compared to holes h+, electrons "e" and holes "h+" are recombined at an interface between the EML and the HTL, not in the luminous materials within the EML. Due to the charge unbalancing, not only the luminous efficiency of the LED is lowered but also a high driving voltage is required in order to realize a desired luminescence, which results in increase in power consumption.

Figure 4:
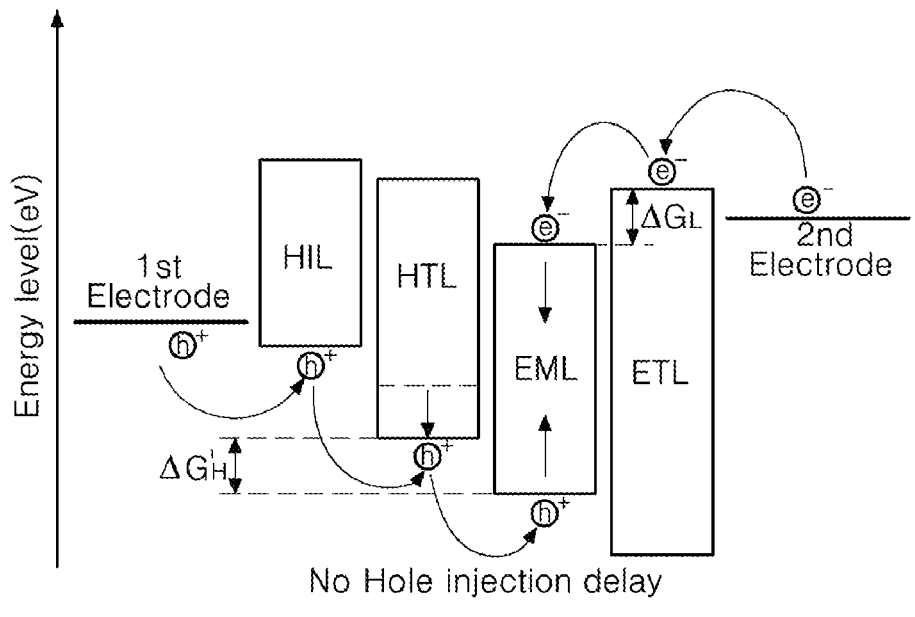
FIG. 4 is a schematic diagram illustrating energy levels among materials in emissive layers between electrodes in accordance with an exemplary aspect of the present disclosure.

On the contrary, since the HTL 344 includes an organic compound having the structure anyone in Chemical Formulae 1 to 4, it is possible to solve those charge unbalancing. FIG. 4 is a schematic diagram illustrating energy levels among materials in emissive layers between electrodes in accordance with an exemplary aspect of the present disclosure.

As illustrated in FIG. 4, when the organic compound having the structure of anyone in Chemical Formulae 1 to 4 is used in the CTL1, for example, HTL 344, the whole HOMO energy level $HOMO_{HTL}$ of the HTL 344 becomes lower (deep $HOMO_{HTL}$). As the energy level energy bandgap "$\Delta G'_H$" between the HOMO energy level $HOMO_{HTL}$ of the HTL 344 and the HOMO energy level $HOMO_{EML}$ of the EML 350 is reduced, i.e. "$\Delta'G_H$"<"$\Delta G_H$", the energy barrier between the HTL 344 and the EML 350 may be removed. In other words, when the organic compound has the structure of anyone in Chemical Formulae 1 to 4, the energy level bandgap "$\Delta'G_H$" between the HOMO energy level $HOMO_{HTL}$ of the HTL 344 and the HOMO energy level $HOMO_{EML}$ of the EML 350 is substantially the same as the energy level bandgap "$\Delta G_L$" between the LUMO energy level $LUMO_{ETL}$ or conduction band energy level $CB_{ETL}$ of the ETL 364 and the LUMO energy level $LUMO_{EML}$ of the EML 350.

When the organic compound having the structure of anyone in Chemical Formulae 1 to 4 is used as a material in the HTL 344, since the electrons "e" and the holes "h+" can be injected into the EML in a balanced manner to form excitons, the amount of electrons that is quenched without forming excitons can be reduced or minimized. Since the electrons "e" and holes "h+" are recombined with each other in the luminous material within the EML 350, not at interfaces between the EML 350 and adjacent CTL (e.g. HTL or ETL), and thereby resulting in efficient light emissions. Accordingly, the LED 300 can maximize its luminous efficiency and lower power consumption since it can be driven at lower voltage.

In one exemplary aspect, the HTL 344 includes only the organic compound having the structure of anyone in Chemical Formulae 1 to 4. In another exemplary aspect, the organic compound having the structure of anyone in Chemical Formulae 1 to 4 may be used as a dopant in the HTL 344. In this case, the HTL 344 may include a host. The host may include, but are not limited to, an organic material having an aryl amine moiety, a fluorene moiety and/or an carbazole moiety, each of which has excellent hole mobility. As an example, the host of the HTL 344 may include, but are not limited to, any organic material having each of the following structure of Chemical Formulae 5 to 8:

Chemical Formula 5

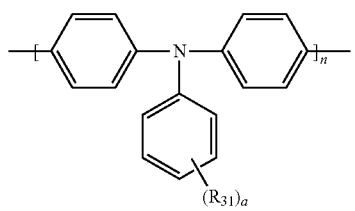

Chemical Formula 6

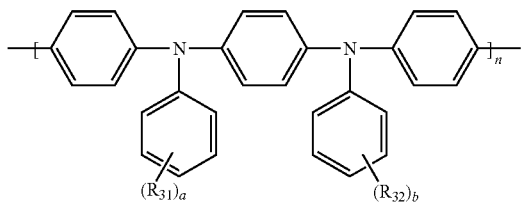

Chemical Formula 7

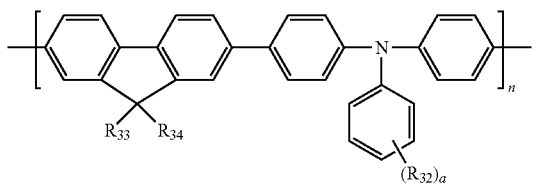

Chemical Formula 8

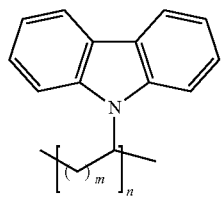

In Chemical Formulae 5 to 7, each of $R_{31}$ to $R_{34}$ is independently unsubstituted or substituted linear or branched $C_1$~$C_{20}$ alkyl group, unsubstituted or substituted $C_1$~$C_{20}$ alkoxy group, unsubstituted or substituted $C_5$~$C_{30}$ aryl group or unsubstituted or substituted $C_4$~$C_{30}$ hetero aryl group. Each of a and b is independently an integer of 1 to 4. In Chemical Formula 8, m is an integer of 1 to 10. In Chemical Formulae 5 to 8, n is an integer of equal to or more than 1.

When the HTL 344 includes the host and the dopant, the HTL 344 may include the organic compound having the structure of anyone in Chemical Formulae 1 to 4 of about 1 to about 50% by weight, but are not limited thereto.

In one exemplary aspect, each of $R_{31}$ to $R_{34}$ in Chemical Formulae 5 to 7 may be independently unsubstituted or substituted linear or branched $C_1$~$C_{10}$ alkyl group. As an example, the organic material having the structure of anyone in Chemical Formulae 5 to 8 may include, but are not limited to, Poly[N,N'-bis(4-butylphenyl)-N,N'-bis(phenyl)-benzidine] (poly-TPD, p-TPD), poly[(9,9-dioctylflorenyl-2,7-diyl)-co-(4,4'-(N-(4-sec-butylphenyl)diphenylamine))] (TFB), poly(N-vinylcarbazole (PVK), poly[bis(4-phenyl)(2,4,6-trimethylphenyl)amine] (PTAA) and the likes.

In an alternative aspect, the host in the HTL 344 may include an organic material having a non-polymer structure. The hole transporting host having the non-polymer structure may include, but are not limited to, N,N'-Bis(3-methylphenyl)-N,N'-bis(phenyl)benzidine (TPD), N,N'-Bis(3-methylphenyl)-N,N'-bis(phenyl)-2,7-diamino-9,9'-spirofluorene (spiro-TPD), N,N'-Bis(3-methylphenyl)-N,N'-bis(phenyl)-9,9'-dioctylfluorene (DOFL-TPD), $N^2,N^7$-Di(naphthalene-1-yl)-9,9-dioctyl-N2,N7-diphenyl-9H-fluorene-2,7-diamine (DOFL-NPB), N,N'-Bis(4-methylphenyl)-N,N'-bis(phenyl) benzidine), $N^1,N^4$-diphenyl-$N^1,N^4$-di-m-tolylbenzene-1,4-diamine (TTP), N,N,N',N'-tetra(3-methylphenyl)3,3'-dimethylbenzidien (HMTPD), di-[4-(N,N'-di-p-tolyl-amino)-phenyl]cyclohexane (TAPC), $N^4,N^{4'}$-Bis(4-(6-((3-ethyloxetan-3-yl)methoxy)hexyl)phenyl)-N4,N4'-diphenylbiphenyl-4,4'-diamine (OTPD), 4,4',4"-tris(N,N-phenyl-3-methylphenylamino)triphenylamine), and the likes.

Figure 5:
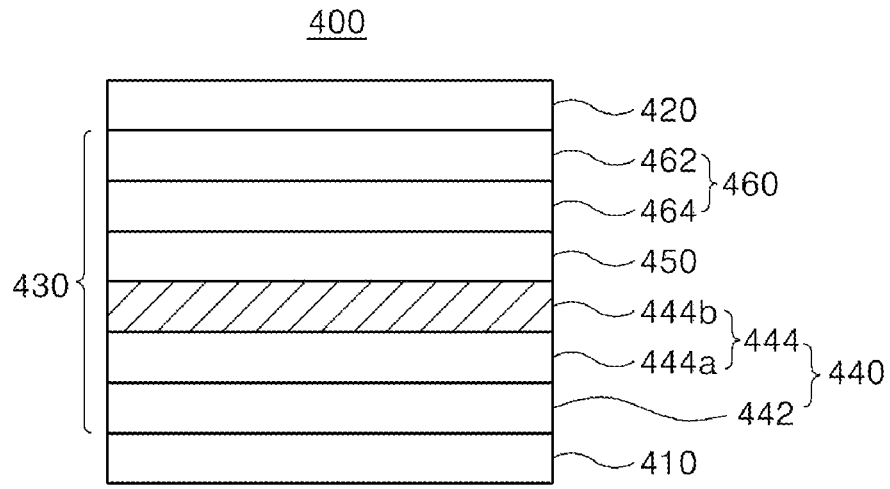
FIG. 5 is a schematic cross-sectional view illustrating a light emitting diode having a normal structure in accordance with another exemplary aspect of the present disclosure.

In one exemplary aspect, the HLT 344 may include the organic material having the polymer structure of anyone in Chemical Formulae 5 to 8 as a host and the organic compound having the structure of anyone in Chemical Formulae 1 to 4 as a dopant. In this case, the hole mobility property of the HTL 344 is increased, the HOMO energy level $HOMO_{HTL}$ of the HTL 344 is lowered (deep $HOMO_{HTL}$), so that it is possible to reduce or remove the HOMO energy barrier between the HTL 344 and the EML 350.

the above first aspect, the OLED 300 has a mono-layered HTL 344. Unlike that aspect, an LED may include a multiple-layered HTL. FIG. 5 is a schematic cross-sectional view illustrating a light emitting diode having a normal structure in accordance with another exemplary aspect of the present disclosure. As illustrated in FIG. 5, the light emitting diode (LED) 400 in accordance with the second aspect of the present disclosure includes a first electrode 410, a second electrode 420 facing the first electrode 410 and an emission layer 430 as an emitting unit disposed between the first and second electrodes 410 and 420. The emissive layer 430 includes an emitting material layer (EML) 450 disposed between the first and second electrodes 410 and 420, a first charge transfer layer (CTL1) 440 disposed between the first electrode 410 and the EML 450 and a second charge transfer layer (CTL2) 460 disposed between the second electrode and the EML 450.

In the second aspect of the present disclosure, the first electrode 410 may be a hole injection electrode and the second electrode 420 may be an electron injection electrode. The CTL1 440 may be a hole transfer layer and may include a hole injection layer (HIL) 442 and a hole transport layer (HTL) 444. The EML 450 may include an inorganic luminescent particles such as QDs and/or QRs or an organic luminous material such an organic host and an organic dopant. The CTL2 460 may be an electron transfer layer and may include an electron injection layer (EIL) 462 and an electron transport layer (ETL) 464.

In an alternative aspect, the LED 400 may further include at least one charge blocking layer such as an electron blocking layer (EBL, not shown) that can control and prevent electron transportations between the HTL 444 and the EML 450 and/or a hole blocking layer (HBL, not shown) that can control and prevent hole transportation between the EML 450 and the ETL 464. The emission layer 430 may have identical structure as the emission layer 330 except the HTL 444.

In this exemplary aspect, the HTL 444 includes a first hole transport layer (HTL1) 444a disposed between the HIL 442 and the EML 450 and a second hole transport layer (HTL2) 444b disposed between the HTL1 444a and the EML 450. Since the organic compound having the structure of anyone in Chemical Formulae 1 to 4 includes a fused aryl or hetero aryl ring, the organic compound has a low HOMO energy level. Considering this property, the HTL1 444a may include other hole transporting material and the HTL2 444b may include the organic compound having the structure of anyone in Chemical Formulae 1 to 4.

As an example, the hole transporting material in the HTL1 444a may include, but are not limited to, an organic material having an aryl or hetero aryl amine moiety, a fluorene moiety and/or a carbazole moiety, each of which shows excellent hole mobility. As an example, the hole transporting material in the HTL1 444a may include the organic material having the structure of anyone in Chemical Formulae 5 to 8. The organic material having the structure of anyone in Chemical Formulae 5 to 8 may include, but are not limited to, p-TPD, TFB, PVK, PTAA and the likes.

In an alternative aspect, the HTL1 444a may include another hole transporting material having a non-polymer structure. The hole transporting material having the non-polymer structure in the HTL1 444a may include, but are not limited to, TPD, spiro-TPD, DOFL-TPD, DOFL-NPB, TTP, HMTPD, TAPC, OTPD, 4,4',4"-tris(N,N-phenyl-3-ethyl-amino)triphenylamine and the likes.

In one exemplary aspect, the HTL 440 may include the hole transporting material having the structure of anyone in Chemical Formulae 5 to 8 in the HTL1 444a and the organic compound having the structure of anyone in Chemical Formulae 1 to 4 in the HTL2 444b. In this case, the hole mobility property of the HTL 444 is increased and a HOMO energy barrier between the HTL 444 and the EML 450 can be reduced, which is resulted from the low HOMO energy level $HOMO_{HTL2}$ of the HTL2 444b. Accordingly, the LED 400 can enhance its luminous efficiency and lower its driving voltage as the holes and electrons are injected into the EML 450 in a balanced manner.

Figure 6:
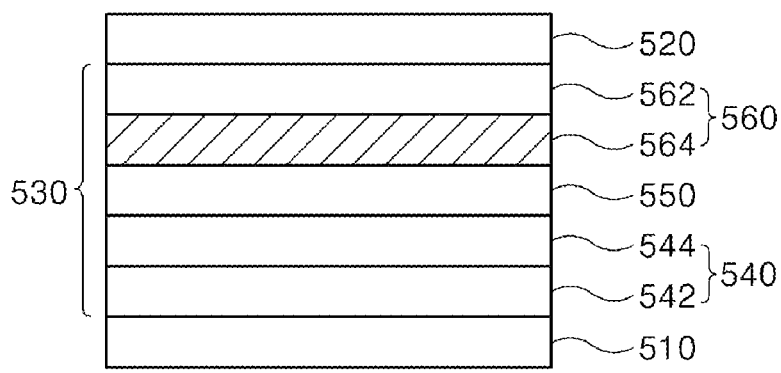
FIG. 6 is a schematic cross-sectional view illustrating a light emitting diode having an inverted structure in accordance with another exemplary aspect of the present disclosure.

In the above aspects, the LEDs 300 and 400 have a normal structure where the hole transfer layer is disposed between the first electrode having relatively higher work function value and the EML and the electron transfer layer is disposed between the second electrode having relatively lower work function value and the EML. In contrast, a light emitting diode may have an inverted structure, not the normal structure. FIG. 6 is a schematic cross-sectional view illustrating a light emitting diode having an inverted structure in accordance with another exemplary aspect of the present disclosure.

As illustrated in FIG. 6, the light emitting diode 500 in accordance with the third aspect of the present disclosure include a first electrode 510, a second electrode 520 facing the first electrode 510 and an emissive layer 530 as an emitting unit disposed between the first and second electrodes 510 and 520. The emissive layer 530 includes an emitting material layer (EML) 550 disposed between the first and second electrodes 510 and 520, a first charge transfer layer (CTL1) 540 disposed between the first electrode 510 and the EML 550 and a second charge transfer layer (CTL2) 560 disposed between the second electrode 520 and the EML 550.

The first electrode 510 may be a cathode such as an electron injection electrode. As an example, the first electrode 510 may include, but are not limited to, a doped or undoped metal oxide such as ITO, IZO, ITZO, OCO, $SnO_2$, $In_2O_3$, Cd:ZnO, F:$SnO_2$, In:$SnO_2$, Ga:$SnO_2$ and AZO, or metal or nonmetal material such as Ni, Pt, Au, Ag, Ir or CNT, other than the above-described metal oxide.

The second electrode 520 may be an anode such as a hole injection layer. As an example, the second electrode 520 may include, but are not limited to, Ca, Ba, Ca/Al, LiF/Ca, LiF/Al, $BaF_2$/Al, CsF/Al, $CaCO_3$/Al, $BaF_2$/Ca/Al, Al, Mg, Au:Mg or Ag:Mg. As an example, each of the first electrode 510 and the second electrode 520 may have a thickness of, but are not limited to, about 5 to about 300 nm, and alternatively about 10 nm to about 200 nm.

The CTL1 540 may be an electron transfer layer which provides electrons into the EML 550. In one exemplary aspect, the CTL1 540 may include an electron injection layer (EIL) 542 disposed adjacently to the first electrode 510 between the first electrode 510 and the EML 550, and an electron transport layer (ETL) 544 disposed adjacently to the EML 550 between the first electrode 510 and the EML 550.

The EIL 542 may include, but are not limited to, a metal such as Al, Cd, Cs, Cu, Ga, Ge, In and/or Li, each of which is undoped or doped with fluorine; and/or metal oxide such as $TiO_2$, ZnO, ZrO, $SnO_2$, $WO_3$ and/or $Ta_2O_3$, each of which is undoped or doped with Al, Mg, In, Li, Ga, Cd, Cs or Cu.

The ETL 544 may include an inorganic material or an organic material. In one exemplary aspect, the ETL 544 may include an inorganic material having excellent charge mobility (i.e. electron mobility) and having a HOMO energy level, or a valence band energy level deeper or lower than a HOMO energy level of the luminous material in the EML 550.

As an example, when the ETL 544 includes an inorganic material, the ETL 544 may include, but are not limited to, a metal oxide undoped or doped with at least one of Al, Mg, In, Li, Ga, Cd, Cs and Cu; a semiconductor particle undoped or doped with at least one of Al, Mg, In, Li, Ga, Cd, Cs and Cu; metal nitrides; and combination thereof.

In one exemplary aspect, the metal component of the metal oxide in the ETL 544 may be selected from, but are not limited to, zinc (Zn), calcium (Ca), magnesium (Mg), titanium (Ti), tin (Sn), tungsten (W), tantalum (Ta), hafnium (Hf), aluminum (Al), zirconium (Zr), barium (Ba) and combination thereof. Particularly, the metal oxide may include, but are not limited to, titanium dioxide ($TiO_2$), zinc oxide (ZnO), magnesium zinc oxide (ZnMgO), zirconium oxide (ZrO), tin oxide ($SnO_2$), tungsten oxide ($WO_3$), tantalum oxide ($Ta_2O_3$), hafnium oxide ($HfO_3$), aluminum oxide ($Al_2O_3$), barium titanium oxide ($BaTiO_3$), and barium zirconium oxide ($BaZrO_3$), each of which is undoped or doped with Al, Mg, In, Li, Ga, Cd, Cs or Cu.

Other inorganic material in the ETL 544 may include, but are not limited to, a semiconductor particle such as CdS, ZnSe, ZnS, each of which is undoped or doped with Al, Mg, In, Li, Ga, Cd, Cs or Cu; nitrides such as $Si_3N_4$; and combination thereof.

In another exemplary aspect, when the ETL 544 includes an organic material, the ETL 544 may include, but are not limited to, oxazole-based compounds, isooxazole-based compounds, triazole-based compounds, isotriazole-based compounds, oxadiazole-based compounds, thiadiazole-based compounds, phenanthroline-based compounds, perylene-based compound, benzoxazole-based compounds, benzothiazole-based compounds, benzimidazole-based compounds, triazine-based compounds and/or aluminum complexes. Particularly, the organic compound of the ETL 544 may include, but are not limited to, TAZ, BCP, TPBi, $Alq_3$, Balq, Salq and combination thereof.

The CTL1 540 may have a mono-layered structure having only the ETL 544. Alternatively, the CTL1 540 may have a mono-layered structure of ETL 544 including a blend of the above-described electron-transporting inorganic material with cesium carbonate.

The CTL1 540, which includes the EIL 542 and/or the ETL 544, may be laminated by any vacuum deposition process such as vacuum vapor deposition and sputtering, or by any solution process such as spin coating, drop coating, dip coating, spray coating, roll coating, flow coating, casting, screen printing and inkjet printing, or combination thereof. As an example, each of the EIL 542 and the ETL 544 may have a thickness, but are not limited to, between about 10 nm and about 200 nm, and alternatively about 10 nm and 100 nm.

The EML 550 may include inorganic luminescent particles or organic luminescent material. As an example, the EML 550 may include inorganic luminescent particles such as quantum dots (QDs) or quantum rods (QRs). The QDs or QRs may have a single-layered structure or a multiple-layered heterologous structure, i.e. core/shell structure. In this case, each of the core and the shell may have single layer or multiple layers, respectively. As an example, the QDs or the QRs may have a type I core/shell structure, a type II core/shell structure or a reverse type I core/shell structure.

In one exemplary aspect, each of the core and the shell may include, but are not limited to, a semiconductor nanocrystals and/or metal oxide nanocrystals having quantum confinement effect. For example, the semiconductor nanocrystals of the core and the shell may be selected from the group, but are not limited to, consisting of Group II-VI compound semiconductor nanocrystals, Group III-V compound semiconductor nanocrystals, Group IV-VI compound semiconductor nanocrystals, Group I-III-VI compound semiconductor nanocrystals and combination thereof.

Particularly, Group II-VI compound semiconductor nanocrystals of the core and/or the shell may be selected from the group, but are not limited to, consisting of MgS, MgSe, MgTe, CaS, CaSe, CaTe, SrS, SrSe, SrTe, BaS, BaSe, BaTe, ZnS, ZnSe, ZnTe, ZnSeS, ZnTeSe, ZnO, CdS, CdSe, CdTe, CdSeS, CdZnS, CdSeTe, CdO, HgS, HgSe, HgTe, CdZnTe, HgCdTe, HgZnSe, HgZnTe, CdS/ZnS, CdS/ZnSe, CdSe/ZnS, CdSe/ZnSe, ZnSe/ZnS, ZnS/CdSZnS, CdS/CdZnS/ZnS, ZnS/ZnSe/CdSe and combination thereof.

Group III-V compound semiconductor nanocrystals of the core and/or shell may be selected from the group, but are not limited to, consisting of AN, AlP, AlAs, AlSb, GaN, GaP, $Ga_2O_3$, GaAs, GaSb, InN, $In_2O_3$, InP, InAs, InSb, AlGaAs, InGaAs, InGaP, AlInAs, AlInSb, GaAsN, GaAsP, GaAsSb, AlGaN, AlGaP, InGaN, InAsSb, InGaSb, AlGaInP, AlGaAsP, InGaAsP, InGaAsSb, InAsSbP, AlInAsP, AlGaAsN, InGaAsN, InAlAsN, GaAsSbN, GaInNAsSb and combination thereof.

Group IV-VI compound semiconductor nanocrystals of the core and/or shell may be selected from the group, but are not limited to, consisting of $TiO_2$, $SnO_2$, SnS, $SnS_2$, SnTe, PbO, $PbO_2$, PbS, PbSe, PbTe, PbSnTe and combination thereof. Also, Group I-III-VI compound semiconductor nanocrystals of the core and/or shell may be selected from the group, but are not limited to, $AgGaS_2$, $AgGaSe_2$, $AgGaTe_2$, $AgInS_2$, $CuInS_2$, $CuInSe_2$, $Cu_2SnS_3$, $CuGaS_2$, $CuGaSe_2$ and combination thereof. Alternatively, each of the core and the shell may independently include multiple layers each of which has different Groups compound semiconductor nanocrystals, e.g., Group II-VI compound semiconductor nanocrystals and Group III-V compound semiconductor nanocrystals such as InP/ZnS, InP/ZnSe, GaP/ZnS, and the likes, respectively.

In another aspect, the metal oxide nanocrystals of the core and/or shell may include, but are not limited to, Group II or Group III metal oxide nanocrystals. As an example, the metal oxide nanocrystals of the core and/or the shell may be selected from the group, but are not limited to, MgO, CaO, SrO, BaO, $Al_2O_3$ and combination thereof.

The semiconductor nanocrystals of the core and/or the shell may be doped with a rare earth element such as Eu, Er, Tb, Tm, Dy or an arbitrary combination thereof or may be doped with a transition metal element such as Mn, Cu, Ag, Al or an arbitrary combination thereof.

As an example, the core in QDs or QRs may include, but are not limited to, ZnSe, ZnTe, CdSe, CdTe, InP, ZnCdS, $Cu_xIn_{1-x}S$, $Cu_xIn_{1-x}Se$, $Ag_xIn_{1-x}S$ and combination thereof. The shell in QDs or QRs may include, but are not limited to, ZnS, GaP, CdS, ZnSe, CdS/ZnS, ZnSe/ZnS, ZnS/ZnSe/CdSe, GaP/ZnS, CdS/CdZnS/ZnS, ZnS/CdSZnS, $Cd_xZn_{1-x}S$ and combination thereof.

In another exemplary aspect, the inorganic luminescent particle may include, but are not limited to, alloy QD or alloy QR such as homogenous alloy QD or QR or gradient alloy QD or QR, e.g. $CdS_xSe_{1-x}$, $CdSe_xTe_{1-x}$, Cd $Cd_xZn_{1-x}S$, $Zn_xCd_{1-x}Se$, $Cu_xIn_{1-x}S$, $Cu_xIn_{1-x}Se$, $Ag_xIn_{1-x}S$.

When the EML 550 includes inorganic luminescent particles such as QDs and/or QRs, the EML 550 may be laminated through any solution process, i.e. coating the dispersion solution, which contains inorganic luminescent particles dissolved in a solvent, on the CTL1 540, for example the HTL 544, and evaporating the solvent. In one aspect, the EML 550 may be laminated on the CTL1 540 using any solution process such as spin coating, drop coating, dip coating, spray coating, roll coating, flow coating casting, screen printing and inkjet printing, or a combination thereof.

In an alternative aspect, the EML 550 may include an organic luminous material. The organic luminous material is not limited to specific organic luminous material. As an example, the EML 550 may include an organic luminous material that emits red (R), green (G) or blue (B) light, and may include fluorescent material or phosphorescent material. As an example, the organic luminous material in the EML 550 may include a host and a dopant. When the organic luminous material constitutes a host-dopant system, the EML 550 may include the dopant, but are not limited to, about 1 to about 50% by weight, and alternatively about 1 to about 30% by weight. Alternatively, when the EML 550 includes an organic luminous material, the EML 550 may include a delayed fluorescent material.

When the EML 550 includes an organic luminous material, the EML 550 may be laminated by any vacuum deposition process such as vacuum vapor deposition and sputtering, or by any solution process such as spin coating, drop coating, dip coating, spray coating, roll coating, flow coating, casting, screen printing and inkjet printing, or a combination thereof. For example, the EML 550 may have a thickness, but are not limited to, between about 5 nm and about 300 nm, alternatively about 10 nm and about 200 nm.

The CTL2 560 may be a hole transfer layer which provides holes into the EML 550. In one exemplary aspect, the CTL2 560 may include a hole injection layer (HIL) 562 disposed adjacently to the second electrode 520 between the second electrode 520 and the EML 550, and a hole transport layer (HTL) 564 disposed adjacently to the EML 550 between the second electrode 520 and the EML 550.

The HIL 562 may include, but are not limited to, a material PEDOT:PSS, TDATA doped with F4-TCNQ, p-doped phthalocyanine such as ZnPc doped with F4-TCNQ, α-NPD doped with F4-TCNQ, HAT-CN and combination thereof. As an example, the HIL 562 may include the dopant such as F4-TCNQ about 1 to about 30% by weight. The HIL 562 may be omitted in compliance with a structure of the LED 500.

The HTL 564 includes the organic compound having the structure of anyone in Chemical Formulae 1 to 4. In one exemplary aspect, the HTL 564 may include only the organic compound having the structure of anyone in Chemical Formula 1 to 4. In another exemplary aspect, the organic compound having the structure of anyone in Chemical Formulae 1 to 4 may be used as dopant in the HTL 564. In this case, the HTL 564 includes other hole transporting material as a host.

The hole transporting host in the HTL 564 is not limited to specific material. In one exemplary aspect, the hole transporting host may be polymer material having an aryl or hetero aryl amine moiety, a fluorene moiety and/or a carbazole moiety, each of which has an excellent hole mobility. As an example, the hole transporting host in the HTL 564 may include, but are not limited to, any organic polymer material having the structure of anyone in Chemical Formulae 5 to 8. The organic polymer material which can be used as the hole transporting material in the HTL 564 may include, but are not limited to, p-TPD, TFB, PVK, PTAA, and the likes.

In another alternative aspect, the hole transporting host in the HTL 564 may be a non-polymer organic material. The hole transporting host of non-polymer structure may include, but are not limited to TPD, spiro-TPD, DOFL-TPD, DOFL-NPB, TTP, HMTPD, TAPC, OTPD, 4,4',4"-tris(N, N-phenyl-3-methhylphenylamino)triphenylamine, and the likes.

In FIG. 6, while the CTL2 560 as a hole transfer layer is divided into the HIL 562 and the HTL 564, the CTL2 560 may have a mono-layered structure. For example, the CTL2 560 may include only the HTL 564 without the HIL 562 or may include the above-mentioned hole transporting material doped with the hole injection material (e.g. PEDOT:PSS).

The CTL2 560 including the HIL 562 and the HTL 564 may be laminated by any vacuum deposition process such as vacuum vapor deposition and sputtering, or by any solution process such as spin coating, drop coating, dip coating, spray coating, roll coating, flow coating, casting, screen printing and inkjet printing, or a combination thereof. For example, each of the HIL 562 and the HTL 564 may have a thickness, but are not limited to, between about 10 nm and 200 nm, and alternatively about 10 nm and 100 nm.

The LED 500 in accordance with the third aspect of the present disclosure may further include at least one exciton blocking layer disposed adjacently to the EML 550. For example, the LED 500 may further include an electron blocking layer (EBL, not shown) that can control and prevent electron transportations between the EML 550 and the HTL 564 and/or a hole blocking layer (HBL, not shown) that can control and prevent hole transportations between the ETL 544 and the EML 550.

Figure 7:
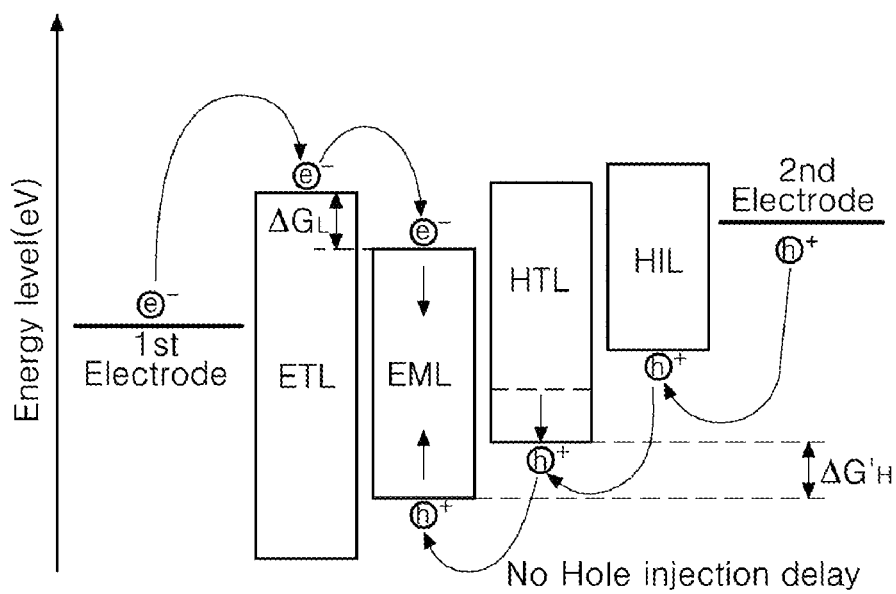
FIG. 7 is a schematic diagram illustrating energy levels among materials in emissive layers between electrodes in accordance with another exemplary aspect of the present disclosure.

The HTL 564 constituting the CTL2 560 disposed between the second electrode 520 and the EML 550 in the LED in accordance with the third aspect of the present disclosure includes the organic compound having the structure of anyone in Chemical Formulae 1 to 4. As described above, the organic compound having the structure of anyone in Chemical Formulae 1 to 4 has a very low HOMO energy level $HOMO_{HTL}$. Accordingly, as the energy level bandgap "$\Delta'G_H$" between the HOMO energy level $HOMO_{HTL}$ of the HTL 564 and the HOMO energy level $HOMO_{EML}$ of the EML 550 is greatly reduced, it is possible to reduce or minimize the energy barrier between the HTL 564 and the EML 550, as illustrated in FIG. 7, which is a schematic diagram illustrating energy levels among materials in emissive layers between electrodes in accordance with another exemplary aspect of the present disclosure.

In other words, when the organic compound having the structure of anyone in Chemical Formulae 1 to 4 is applied into the HTL 564, the energy level bandgap "$\Delta'G_H$" between the HOMO energy level $HOMO_{HTL}$ of the HTL 564 and the HOMO energy level $HOMO_{EML}$ of the EML 550 is substantially the same as the energy level bandgap "$\Delta G_L$" between the LUMO energy level $LUMO_{ETL}$ or conduction band energy level $CB_{ETL}$ of the ETL 544 and the LUMO energy level $LUMO_{EML}$ of the EML 550. Since the electrons "(e)$^-$" and the holes "(h)$^+$" can be injected into the EML in a balanced manner to form excitons, the amount of electrons that is quenched without forming excitons can be reduced or minimized. In addition, the electrons "(e)$^-$" and holes "(h)$^+$" are recombined with each other in the luminous material within the EML 550, not at interfaces between the EML 550 and adjacent CTL (e.g. HTL or ETL). Accordingly, the LED 500 can maximize its luminous efficiency and lower power consumption since it can be driven at lower voltage.

Figure 8:
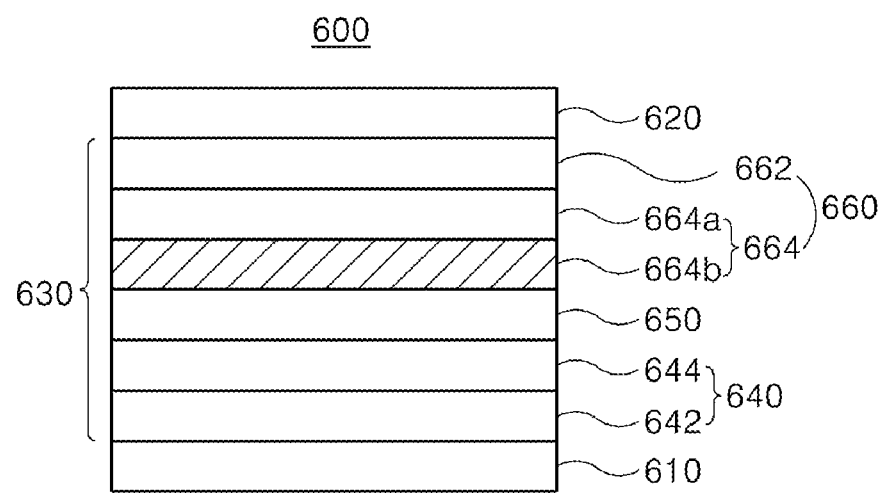
FIG. 8 is a schematic cross-sectional view illustrating a light emitting diode having an inverted structure in accordance with still another exemplary aspect of the present disclosure.

An LED having an inverted structure may have a multiple-layered hole transport layer. FIG. 8 is a schematic cross-sectional view illustrating a light emitting diode having an inverted structure in accordance with still another exemplary aspect of the present disclosure.

As illustrated in FIG. 8, the light emitting diode (LED) 600 in accordance with the fourth aspect of the present disclosure includes a first electrode 610, a second electrode 620 facing the first electrode 610 and an emission layer 630 as an emitting unit disposed between the first and second electrodes 610 and 620. The emissive layer 630 includes an emitting material layer (EML) 650 disposed between the first and second electrodes 610 and 620, a first charge transfer layer (CTL1) 640 disposed between the first electrode 610 and the EML 650 and a second charge transfer layer (CTL2) 660 disposed between the second electrode and the EML 650.

In the fourth aspect of the present disclosure, the first electrode 610 may an electron injection electrode and the second electrode 620 may be a hole injection electrode. The CTL1 640 may be an electron transfer layer and may include an electron injection layer (EIL) 642 and an electron transport layer (ETL) 644. The EML 650 may include an inorganic luminescent particles such as QDs and/or QRs or an organic luminous material such an organic host and an organic dopant. The CTL2 660 may be a hole transfer layer and may include a hole injection layer (HIL) 662 and a hole transport layer (HTL) 664.

In an alternative aspect, the LED 600 may further include at least one charge blocking layer such as an electron blocking layer (EBL, not shown) that can control and prevent electron transportations between the HTL 664 and the EML 650 and/or a hole blocking layer (HBL, not shown) that can control and prevent hole transportation between the EML 650 and the ETL 644. The emission layer 630 may have identical structure as the emission layer 530 except the HTL 664.

In this exemplary aspect, the HTL 664 includes a first hole transport layer (HTL1) 664a disposed between the HIL 662 and the EML 650 and a second hole transport layer (HTL2) 664b disposed between the HTL1 664a and the EML 650. As an example, the HTL1 664a may include other hole transporting material and the HTL2 664b may include the organic compound having the structure of anyone in Chemical Formulae 1 to 4.

As an example, the hole transporting material in the HTL1 664a may include, but are not limited to, an organic material having an aryl or hetero aryl amine moiety, a fluorene moiety and/or a carbazole moiety, each of which shows excellent hole mobility. As an example, the hole transporting material in the HTL1 664a may include the organic material having the structure of anyone in Chemical Formulae 5 to 8. The organic material having the structure of anyone in Chemical Formulae 5 to 8 may include, but are not limited to, p-TPD, TFB, PVK, PTAA and the likes.

In an alternative aspect, the HTL1 664a may include another hole transporting material having a non-polymer structure. The hole transporting material having the non-polymer structure in the HTL1 664a may include, but are not limited to, TPD, spiro-TPD, DOFL-TPD, DOFL-NPB, TTP, HMTPD, TAPC, OTPD, 4,4',4"-tris(N,N-phenyl-3-ethyl-amino)triphenylamine and the likes.

In one exemplary aspect, the HTL 664 may include the hole transporting material having the structure of anyone in Chemical Formulae 5 to 8 in the HTL1 664a and the organic compound having the structure of anyone in Chemical Formulae 1 to 4 in the HTL2 664b. In this case, the hole mobility property of the HTL 664 is increased and a HOMO energy barrier between the HTL 664 and the EML 650 can be reduced, which is resulted from the low HOMO energy level HOMO$_{HTL2}$ of the HTL2 664b. Accordingly, the LED 600 can enhance its luminous efficiency and lower its driving voltage as the holes and electrons are injected into the EML 650 in a balanced manner.

Synthesis Example 1: Synthesis of Compound H01

(1) Synthesis of Intermediate 1-1

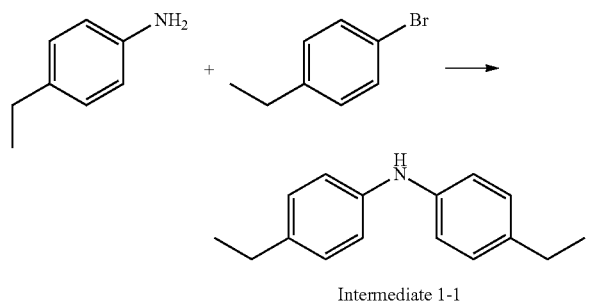

Intermediate 1-1

30.0 g (247 mmol) of 4-ethyl aniline, 45.81 g (248 mmol) of 1-bromo-4-ethyl benzene, 1.27 g (2.5 mmol) of bis(tr-tert-butylphosphine) palladium (0) (Pd(P(t-Bu)$_3$)$_2$), and 90 g of sodium-tert-butoxide (t-BuONa) were placed into a 1000 mL round bottom flask, 300 mL of toluene was added into the flask, and then the solution was stirred. After reaction was completed, the solution was extracted with 500 mL of dichloromethane and water and then distilled under reduced pressure to obtain a solid. Then, the solid was separated and purified by column chromatography to give 50 g of intermediate 1-1.

(2) Synthesis of Intermediate 1-2

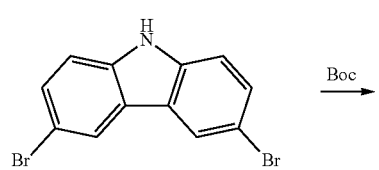

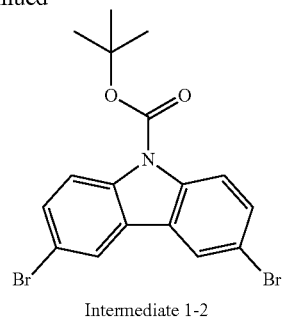

Intermediate 1-2

50.0 g (154 mmol) of 3,6-dibromo-9H-carbazole, 33.80 g (154 mmol) of di-tert-butyl dicarbonate (BOC), 28 g (231 mmol) of 4-dimethylaminopyridine (4-DMAP) and 31.2 g (308 mmol) of triethylamine were placed into a 1000 mL round bottom flasks, 500 mL of tetrahydrofuran (THF) was added into the flask, and then the solution was stirred. After reaction was completed, the solution was extracted with 500 mL of dichloromethane and water, and then distilled under reduced pressure to obtain a solid. Then, the solid was separated and purified by column chromatography to give 70 g of intermediate 1-2.

(3) Synthesis of Intermediate 1-3

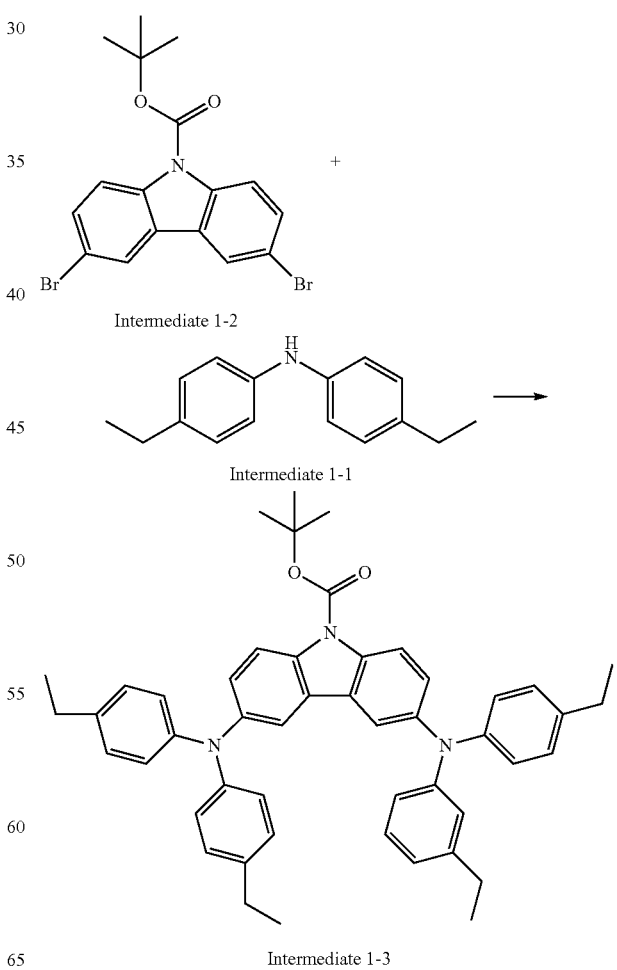

Intermediate 1-3

30.0 g (70.9 mmol) of intermediate 1-2, 17.5 g (78.0 mmol) of intermediate 1-1, 0.36 g (0.71 mmol) of Pd(P(t-Bu)$_3$)$_2$ and 20 g (212 mmol) of t-BuONa were placed into a 1000 mL round bottom flasks, 300 mL of toluene was added into the flasks, and then the solution was stirred. After reaction was completed, the solution was extracted with 300 mL of dichloromethane and water, and then distilled under reduced pressure to obtain a solid. Then, the solid was separated and purified by column chromatography to give 47 g of intermediate 1-3.

(4) Synthesis of Intermediate 1-4

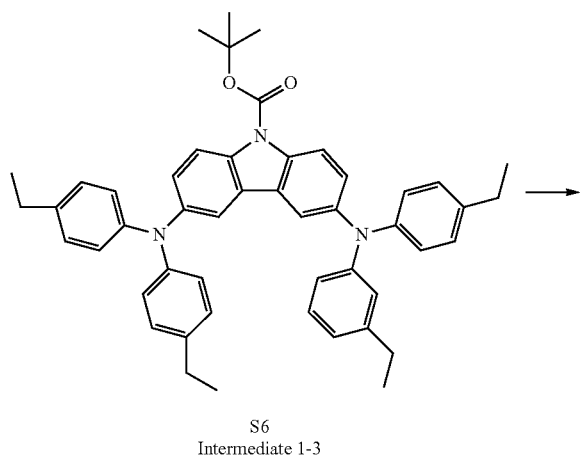

S6
Intermediate 1-3

S7
Intermediate 1-4

47 g (65.9 mmol) of the purified intermediate 1-3 and 14.3 g (65.9 mmol) of HCl were added into a mixed solvent of 20 mL of H$_2$O and 300 mL of THF, and then the solution was stirred at room temperature. After reaction was completed, the solvent was distilled under reduced pressure to give a solid. The solid was recrystallized with dichloromethane and ether to give 50 g of intermediate 1-4.

(5) Synthesis of Intermediate 1-5

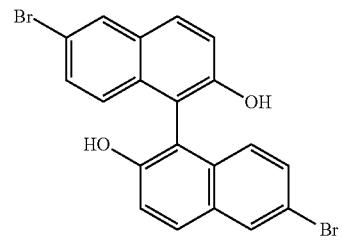

$\xrightarrow{\text{Br}_2}{\text{MC}}$

Intermediate 1-5

20.0 g (69.9 mmol) of 2,2'-dihydroxy-1,1'-binaphthyl and 24.56 g (15 mmol) of Br$_2$ were placed into a 1000 mL round bottom flask, 200 mL of dichloromethane was added into the flask, and then the solution was stirred. After reaction was completed, the solution was extracted with excessive water and then distilled under reduced pressure to obtain a crude product. Then, the crude product was separated and purified by column chromatography to give 28.5 g of intermediated 1-5.

(6) Synthesis of Intermediate 1-6

Intermediate 1-5

Intermediate 1-6

15.5 g (69.5 mmol) of the purified intermediate 1-5, 21 g (153 mmol) of 1-bromobutane and 14.4 g (104 mmol) of K$_2$CO$_3$ were placed into a 1000 mL round bottom flask, 150 mL of toluene was added into the flasks, and then the solution was stirred. After reaction was completed, the solution was extracted with 300 mL of dichloromethane and water and then distilled under reduced pressure to obtain a solid. Then, the solid was separated and purified by column chromatography to give 35 g of intermediate 1-6.

(7) Synthesis of Compound H01

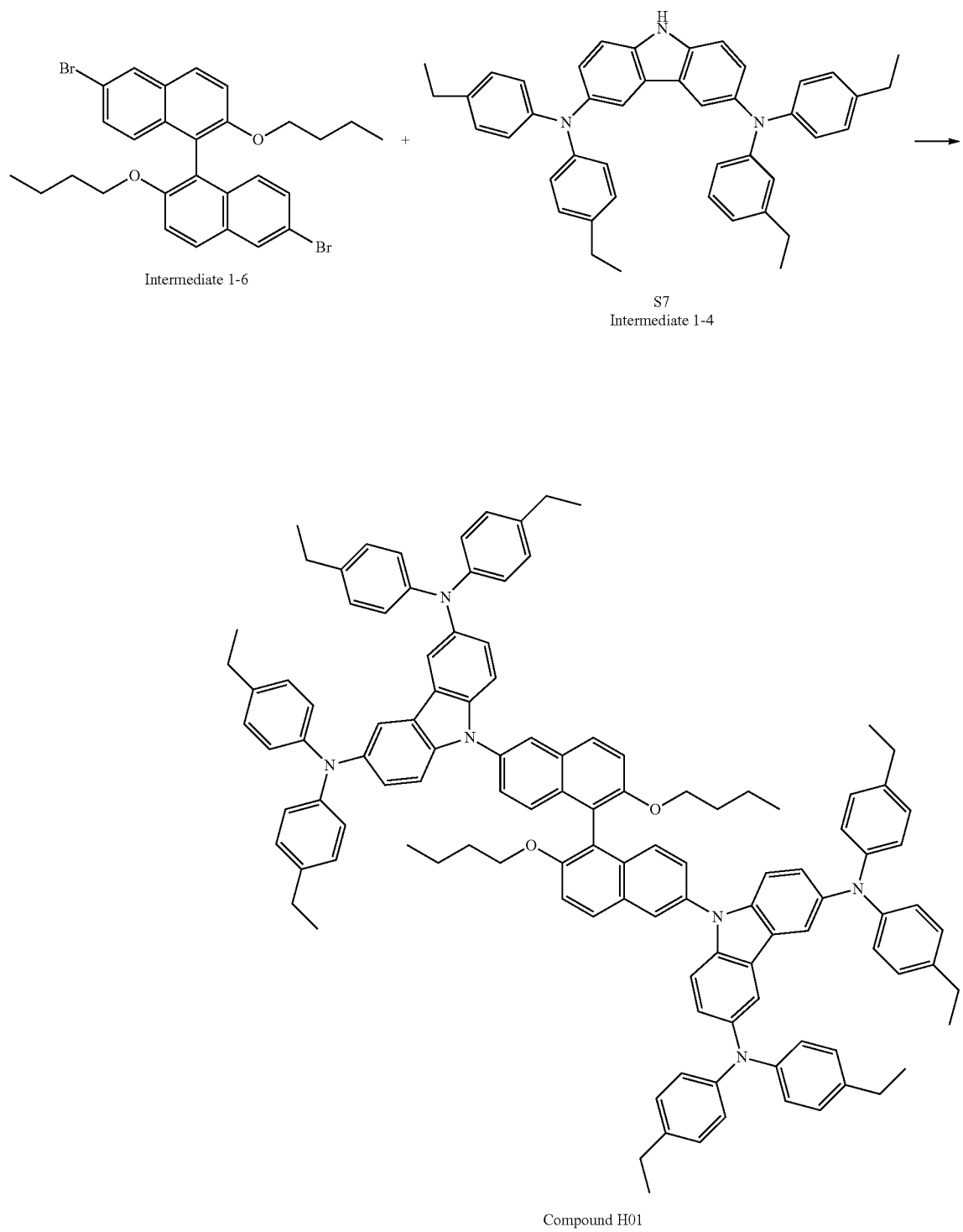

Intermediate 1-6

S7
Intermediate 1-4

Compound H01

10.0 g (18.0 mmol) of intermediate 1-6, 15.45 g (40.0 mmol) of intermediate 1-4, 0.28 g (0.50 mmol) of Pd(P(t-Bu)$_3$)$_2$ and 30 g of t-BuONa were placed into a 1000 mL round bottom flasks, 150 mL of toluene was added into the flasks, and then the solution was stirred. After reaction was completed, the solution was extracted with 300 mL of dichloromethane and water and then distilled under reduced pressure to obtain a solid. Then, the solid was separated and purified by column chromatography to give 21.1 g of Compound H01.

Synthesis Example 2: Synthesis of Compound H02

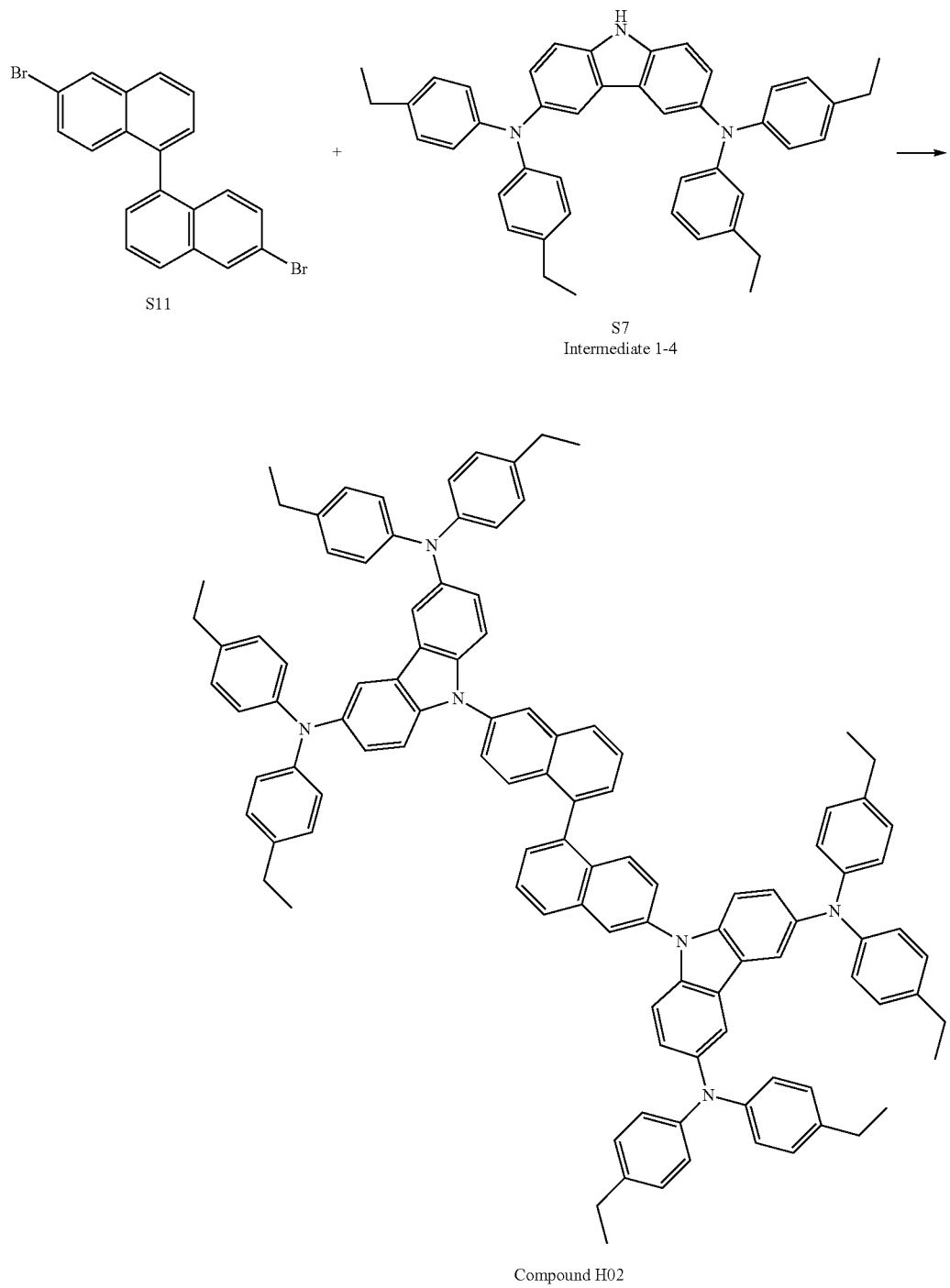 [SMILES: Brc1ccc2c(-c3cccc4cc(Br)ccc34)cccc2c1 ; CCc1ccc(N(c2ccc(CC)cc2)c2ccc3[nH]c4ccc(N(c5ccc(CC)cc5)c5cccc(CC)c5)cc4c3c2)cc1 ; "S11" ; CCc1ccc(N(c2ccc(CC)cc2)c2ccc3c(c2)c2cc(N(c4ccc(CC)cc4)c4ccc(CC)cc4)ccc2n3-c2ccc3c(-c4cccc5cc(-n6c7ccc(N(c8ccc(CC)cc8)c8ccc(CC)cc8)cc7c7cc(N(c8ccc(CC)cc8)c8ccc(CC)cc8)ccc76)ccc45)cccc3c2)cc1]

20.0 g (48.7 mmol) of 6,6-dibromo-1,1'-binaphthyl, 65.8 g (107.1 mmol) of intermediate 1-4, 0.50 g (1.46 mmol) of Pd(P(t-Bu)$_3$)$_2$ and 60 g (146 mmol) of t-BuONa were placed into a 500 mL round bottom flasks, 500 mL of toluene was added into the flasks, and then the solution was stirred. After reaction was completed, the solution was distilled under reduced pressure to remove the solvent, extracted with 300 mL of dichloromethane and water and then distilled under reduced pressure to obtain a solid. Then, the solid was separated and purified by column chromatography to give 35 g of Compound H02.

Synthesis Example 3: Synthesis of Compound H03

(1) Synthesis of Intermediate 3-1

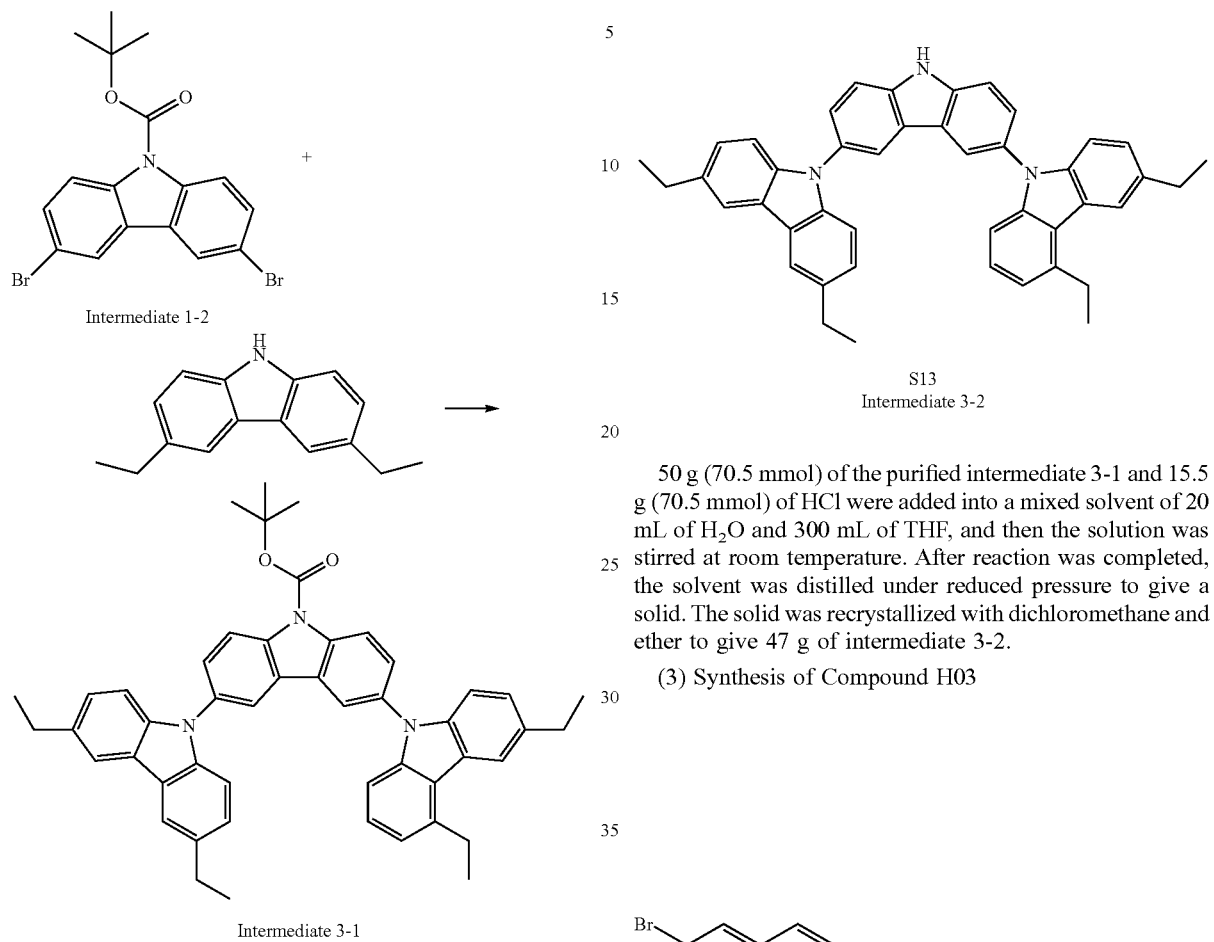

30.0 g (70.9 mmol) of intermediate 1-2, 17.4 g (78.0 mmol) of 3,6-diethyl-9H-carbazole, 0.36 g (0.71 mmol) of Pd(P(t-Bu)$_3$)$_2$ and 20 g (212 mmol) of t-BuONa were placed into a 1000 mL round bottom flasks, 300 mL of toluene was added into the flasks, and then the solution was stirred. After reaction was completed, the solution was extracted with 300 mL of dichloromethane and water, and then distilled under reduced pressure to obtain a solid. Then, the solid was separated and purified by column chromatography to give 50 g of intermediate 3-1.

(2) Synthesis of Intermediate 3-2

50 g (70.5 mmol) of the purified intermediate 3-1 and 15.5 g (70.5 mmol) of HCl were added into a mixed solvent of 20 mL of H$_2$O and 300 mL of THF, and then the solution was stirred at room temperature. After reaction was completed, the solvent was distilled under reduced pressure to give a solid. The solid was recrystallized with dichloromethane and ether to give 47 g of intermediate 3-2.

(3) Synthesis of Compound H03

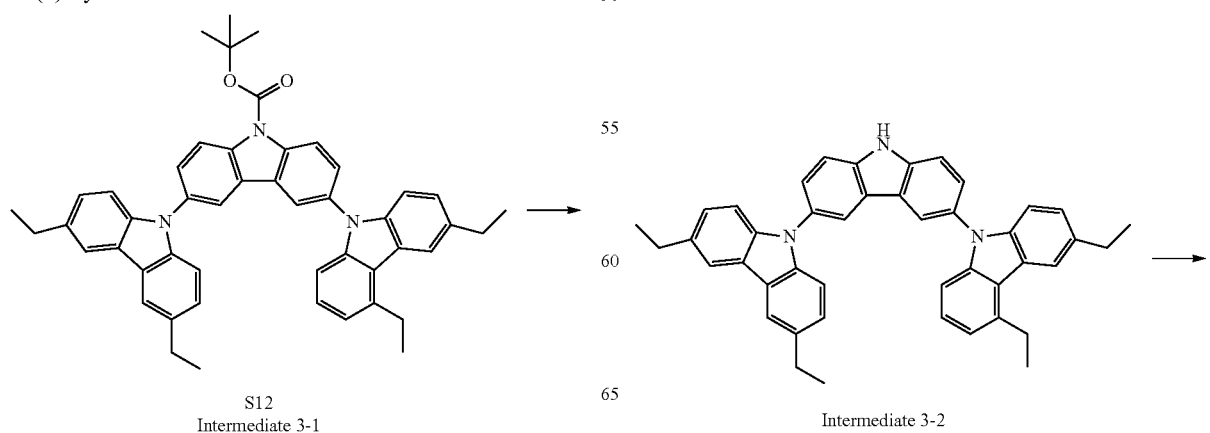

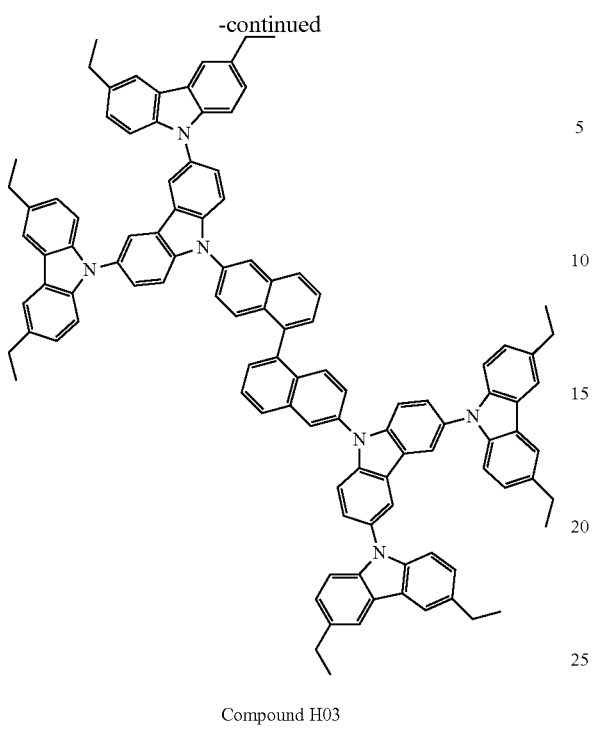

Compound H03

20.0 g (48.7 mmol) of 6,6'-dibromo-1,1'-binaphthyl, 62.4 g (58.6 mmol) of intermediate 3-2, 0.50 g (1.46 mmol) of Pd(P(t-Bu)$_3$)$_2$ and 60 g (146 mmol) of t-BuONa were placed into a 500 mL round bottom flasks, 500 mL of toluene was added into the flasks, and then the solution was stirred. After reaction was completed, the solution was distilled under reduced pressure to remove the solvent, was extracted with 300 mL of dichloromethane and water, and then distilled under reduced pressure to give a solid. Then, the solid was separated and purified by column chromatography to give 35 of Compound H03.

Synthesis Example 4: Synthesis of Compound H12

(1) Synthesis of Intermediate 4-1

130 g (777 mmol) of carbazole, 165 g (855 mmol) of 1-bromo-2-ethylhexane and 20.5 g (855 mmol) of sodium hydride were placed into a 2000 mL round bottom flask, 1300 mL of THF was added into the flask, and then the solution was stirred. After reaction was completed, the solution was extracted with dichloromethane and water and then distilled under reduced pressure to obtain a solid. Then, the solid was separated and purified by column chromatography to give 215 g of intermediate 4-1.

(2) Synthesis of Intermediate 4-2

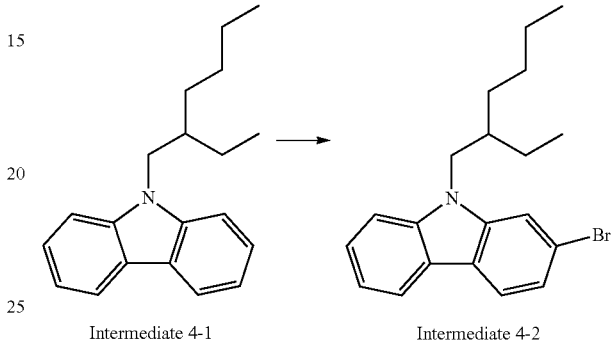

Intermediate 4-1        Intermediate 4-2

108 g (388 mmol) of the purified intermediate 4-1 and 76 g (427 mmol) of N-bromosuccinimide were placed into a 2000 mL round bottom flask, 1100 mL of dichloromethane was added into the flask, and then the solution was stirred. After reaction was completed, the solution was extracted with water and distilled under reduced pressure to obtain a solid. Then, the solid was separated and purified by column chromatography to give 119 g of intermediate 4-2.

(3) Synthesis of Intermediate 4-4

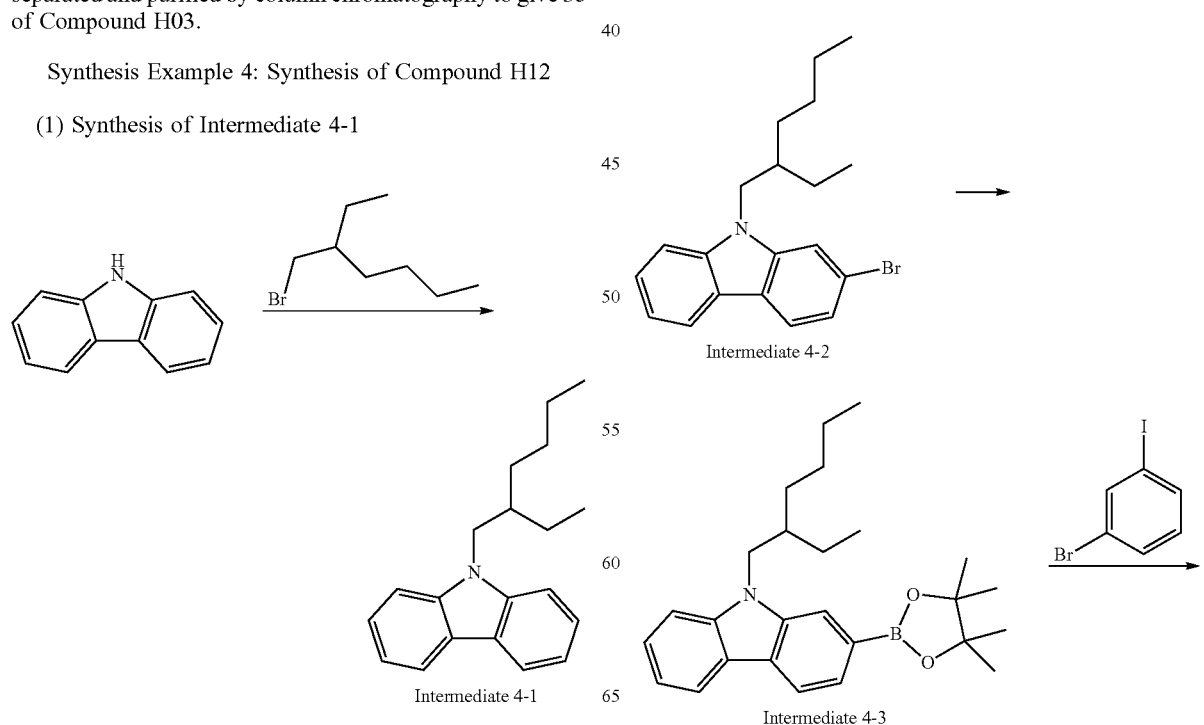

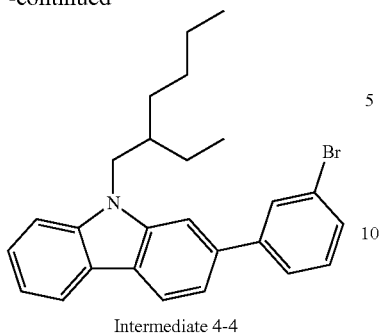

Intermediate 4-4

108 g (389 mmol) of intermediate 4-2 and 76.1 g (178 mmol) of bis(pinacolato)diboron were placed into a 1000 mL round bottom flask, 700 mL of dichloromethane was added into the flask, and then the solution was stirred. After reaction was completed, the solution was extracted with dichloromethane and water and then distilled under reduced pressure to give intermediate 4-3. 39.4 g (97.2 mmol) of the obtained intermediate 4-3, 30.4 g (107 mmol) of 1-bromo-4-iodobenzene, 1.12 g (0.97 mmol) of tetrakis(triphenylphosphine) palladium (0) (Pd(pph$_3$)$_4$) and 295 g of 1M K$_2$CO$_3$ was dissolved in 600 mL of THF, and the solution was heated with stirring. After reaction was completed, the solution was extracted with dichloromethane and water and then distilled under reduced pressure to obtain a solid. Then, the solid was separated and purified by column chromatography to give 40 g of intermediated 4-4.

(4) Synthesis of Intermediate 4-5

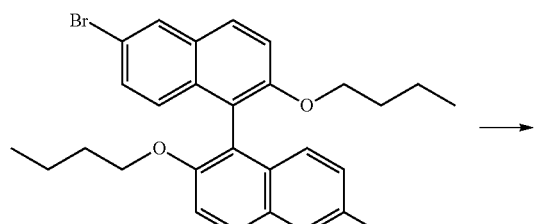

Intermediate 1-6

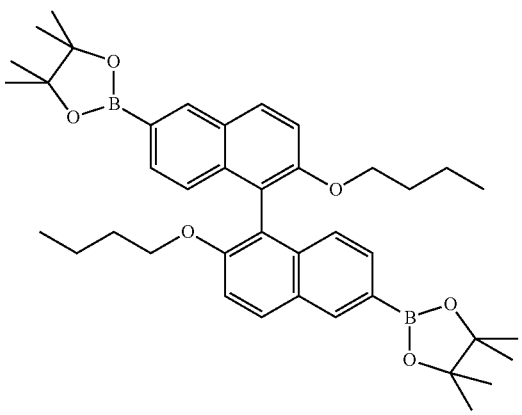

Intermediate 4-5

16 g (28.7 mmol) of intermediate 1-6, 16.2 g (28.7 mmol) of bis(pinacolato)diboron, 0.47 g (0.57 mmol) of [1,1'-bis(diphenylphosphino)ferrocene]dichloro palladium (II) complex with dichloromethane (Pd(dppf)Cl$_2$.DCM) and 5.63 g (57.4 mmol) of potassium acetate (KOAc) were placed into a 500 mL round bottom flasks, 200 mL of 1,4-dioxane was added into the flasks, and then the solution was stirred. After reaction was completed, the solution was distilled under reduced pressure to remove the reaction solvent, extracted with dichloromethane and water and distilled under reduced pressure again to obtain a crude product. Then, the crude product was separated and purified by column chromatography to give 15 g of intermediate 4-5.

(5) Synthesis of Compound H12

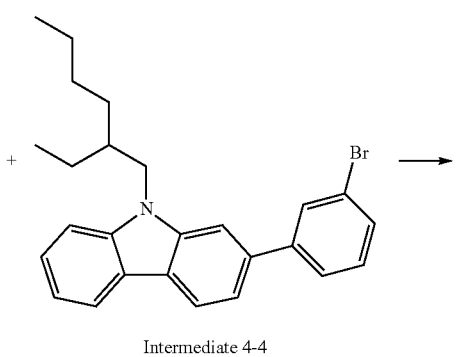

Intermediate 4-5 + Intermediate 4-4 →

-continued

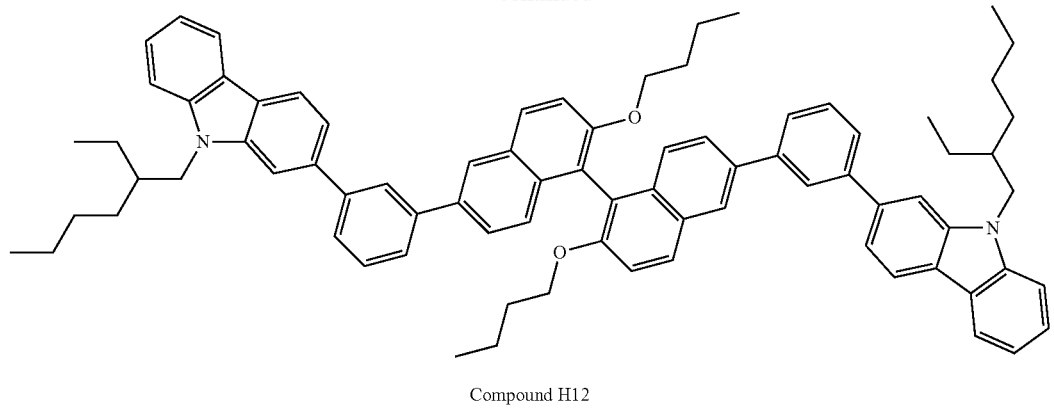

Compound H12

9.3 g (14.3 mmol) of intermediate 4-5, 13.7 g (31.6 mmol) of intermediate 4-4, 0.83 g (0.7 mmol) of Pd(pph$_3$)$_4$ and 140 g of 2M K$_2$CO$_3$ were placed into a 1000 mL round bottom flasks, 300 mL of dioxane was added into the flask, and then the solution was heated with stirring. After reaction was completed, the solution was extracted with dichloromethane and water and then distilled under reduced pressure to obtain a solid. Then, the solid was separated and purified by column chromatography to give 14.5 g of Compound H12.

Synthesis Example 5: Synthesis of Compound H13

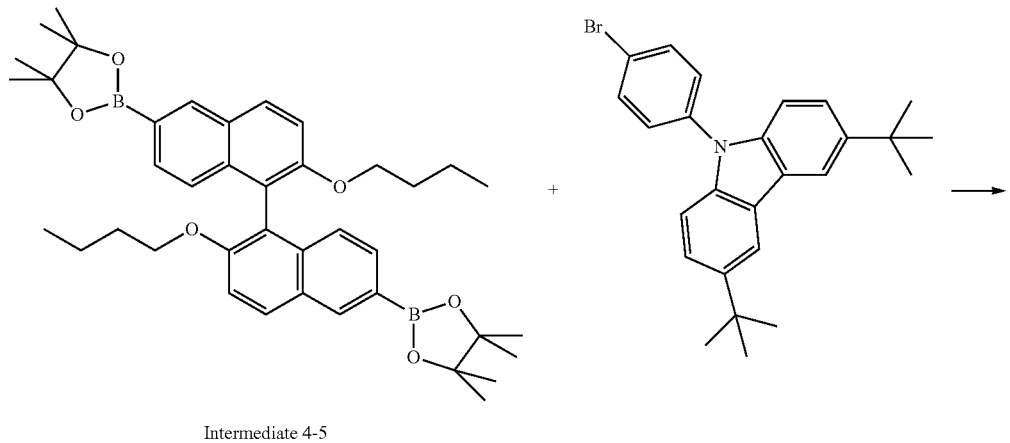

Intermediate 4-5

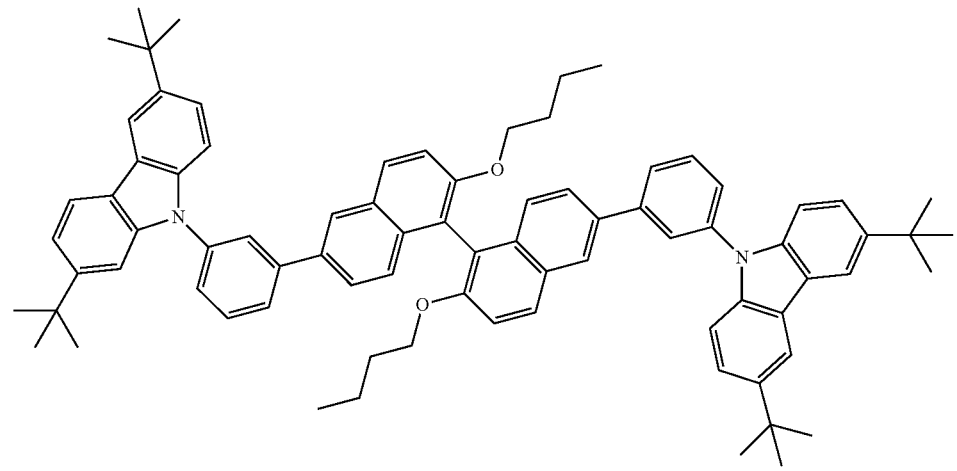

Compound H13

12.5 g (18.5 mmol) of intermediate 4-5, 16.0 g (37.0 mmol) of [9-(4-bromophenyl)]-3,6-di-tert-butyl-9H-carbazole, 1.08 g (0.91 mmol) of Pd(pph$_3$)$_4$ and 156 g of 2M K$_2$CO$_3$ were placed into a 1000 mL round bottom flasks, 500 mL of dioxane was added into the flask, and then the solution was heated with stirring. After reaction was completed, the solution was extracted with dichloromethane and water and then distilled under reduced pressure to obtain a solid. Then, the solid was separated and purified by column chromatography to give 18 g of Compound H13.

Example 1: Fabrication of Light Emitting Diode (LED)

A light emitting diode was fabricated applying Compound H01 synthesized in the Synthesis Example 1 into a hole transport layer. An ITO-glass was patterned to have luminous area 3 mm×3 mm and washed. And an emissive layer and cathode were laminated as the following order:

a hole injection layer (HIL) (PEDOT:PSS; spin coating (5000 rpm) and heating for 30 minutes at 150° C.; 20 to 40 nm); a hole transport layer (HTL) (Compound H01; spin coating (4000 rpm) in toluene (8 mg/mL) and heating for 30 minutes at 170° C.; 10 to 30 nm); an emitting material layer (EML) (red quantum dot InP/ZnSe/ZnS; spin coating (2000 rpm) in hexane (10 mg/mL) and heating for 1 hour at 80° C.; 10 to 30 nm); an electron transport layer (ETL) (ZnO; spin coating (4000 rpm) in ethanol (25 mg/mL) and heating for 30 minutes at 80° C.; 30 to 50 nm).

And then, the ITO-glass substrate having the laminated charge transfer layers and the EML was transferred to a vacuum chamber, where a cathode (Al; 80 nm) was deposited under 10$^{-6}$ Torr. After depositing the cathode, the LED was transferred from the vacuum chamber to a dry box for film formation, followed by encapsulation using UV-curable epoxy and moisture getter. The manufacture organic light emitting diode had an emission area of 9 mm$^2$.

Examples 2 to 5: Manufacture of LED

A LED was manufactured by repeating the same process and using the same material as Example 1, except using the Compound H02 (Example 2), the Compound H03 (Example 3), the Compound H12 (Example 4) or the Compound H13 (Example 5) in place of the Compound H01 as a hole transporting material in the HTL.

Comparative Examples 1 and 2: Manufacture of LED

A LED was manufactured by repeating the same process and using the same material as Example 1, except using p-TPD (Comparative Example 1, Ref. 1) or TFB (Comparative Example, Ref. 2) in place of the Compound 1 as a hole material in the HTL.

Experimental Example 1: Measurement of Luminous Properties of OLED

Each of the light emitting diode manufactured by Examples 1 to 5 and Ref. 1 to 2 was connected to an external power source, and luminous properties for all the diodes were evaluated using a constant current source (KEITHLEY) and a photometer PR650 at room temperature. In particular, driving voltage (V), current efficiency (cd/A), external quantum efficiency (EQE; %) and color coordinates for emission wavelength at a current density of 10 mA/cm$^2$ of the light emitting diodes of Examples 1 to 5 and Ref. 1 to 2 were measured. The results thereof are shown in the following Table 1.

TABLE 1

| | | Luminous Properties LED | | | | |
| | | 10 mA/cm$^2$ | | | | |
| Sample | HTL | V | cd/A | EQE (%) | CIEx | CIEy |
|---|---|---|---|---|---|---|
| Ref. 1 | p-TPD | 9.2 | 0.75 | 1.13 | 0.675 | 0.320 |
| Ref. 2 | TFB | 7.1 | 1.67 | 2.15 | 0.662 | 0.321 |
| Example 1 | H01 | 5.42 | 4.09 | 5.80 | 0.678 | 0.3201 |
| Example 2 | H02 | 5.39 | 3.67 | 5.35 | 0.6774 | 0.3195 |
| Example 3 | H03 | 5.43 | 4.02 | 5.66 | 0.6783 | 0.3202 |
| Example 4 | H12 | 4.4 | 2.84 | 4.22 | 0.681 | 0.316 |
| Example 5 | H13 | 4.4 | 3.54 | 5.17 | 0.678 | 0.316 |

As indicated in Table 1, the LED using the organic compound in the HTL as Examples 1 to 5 has enhanced luminous efficiency compared with the LED using the prior art hole transporting materials, p-TPD or TFB in the HTL as Ref. 1 and Ref. 2. Particularly, compared with the LED using the prior art hole transporting material as the Refs. 1 and 2, the LED using the organic compound in the HTL as Examples 1 to 5 reduced driving voltage up to 52.2%, and improved current efficiency up to 445.3% and EQE up to 400.9%. The LED manufactured in Examples 1 to 5 showed substantially identical color coordinates to the LED manufactured in Refs. 1 and 2, which indicate that it is possible to realize desired luminescence by applying the organic compounds to the HTL.

Examples 6 to 10: Manufacture of LED

A LED was manufactured by repeating the same process and using the same material as Example 1, except using TFB:H01 (host:dopant, 1:1 by volume ratio) (Example 6), TFB:H02 (host:dopant, 1:1 by volume ratio) (Example 7), TFB:H03 (host:dopant, 1:1 by volume ratio) (Example 8), TFB:H12 (host:dopant; 1:1 by volume ratio) (Example 9) or TFB:H13 (host:dopant, 1:1 by volume ration) (Example 10) in place of using only the Compound H01 as a hole transporting material in the HTL.

Comparative Examples 3 and 4: Manufacture of LED

A LED was manufactured by repeating the same process and using the same material as Example 1, except using TFB:CBP (4,4'-Bis(N-carbazolyl)-1,1'-biphenyl) (host:dopant, 1:1 by volume ratio) (Comparative Example 3, Ref. 3) or TFB:TCTA (Tris(3-carbazolyl-9-yl-phenyl)amine) (host:dopant, 1:1 by volume ratio) (Comparative Example 4, Ref. 4) in place of using only the Compound H01 as a hole transporting material of the HTL.

Experimental Example 2: Measurement of Luminous Properties of OLED

Luminous properties for LEDs manufactured in Examples 4 to 6 and Refs. 1 to 4 were measured as the same process as Experimental Example 1. The measurement results are shown in the following Table 2.

TABLE 2

Luminous Properties LED

| Sample | HTL | 10 mA/cm² | | | | |
|---|---|---|---|---|---|---|
| | | V | cd/A | EQE (%) | CIEx | CIEy |
| Ref. 1 | p-TPD | 9.2 | 0.75 | 1.13 | 0.675 | 0.320 |
| Ref. 2 | TFB | 7.1 | 1.67 | 2.15 | 0.662 | 0.321 |
| Ref. 3 | TFB:CBP | 10.9 | 0.56 | 0.85 | 0.678 | 0.316 |
| Ref. 4 | TFB:TCTA | 10.8 | 0.88 | 1.52 | 0.677 | 0.319 |
| Example 6 | TFB:H01 | 4.42 | 4.83 | 5.80 | 0.678 | 0.316 |
| Example 7 | TFB:H02 | 4.77 | 4.36 | 5.91 | 0.680 | 0.318 |
| Example 8 | TFB:H03 | 4.83 | 4.08 | 5.65 | 0.681 | 0.318 |
| Example 9 | TFB:H12 | 4.30 | 4.36 | 5.65 | 0.681 | 0.316 |
| Example 10 | TFB:H13 | 4.0 | 4.39 | 5.91 | 0.680 | 0.3116 |

As indicated in Table 2, the LED using the organic compound as a dopant in the HTL as Examples 6 to 10 has enhanced luminous efficiency compared with the LED using only the prior art hole transporting material or using the prior art hole transporting materials as a dopant in the HTL as Ref. 1 to Ref. 4. Particularly, compared with the LED using the prior art hole transporting material as the Refs. 1 and 2, the LED using the organic compound as a dopant in the HTL as Examples 6 to 10 reduced driving voltage up to 56.5%, and improved current efficiency up to 544.0% and EQE up to 423.3%. In addition, compared with the LED using the prior art hole transporting material as a dopant in the HTL as the Refs. 3 and 4, the LED using the organic compound as a dopant in the HTL as Examples 6 to 10 reduced driving voltage up to 63.3%, and improved current efficiency up to 762.5% and EQE up to 595.3%. The LED manufactured in Examples 6 to 10 showed substantially identical color coordinates to the LED manufactured in Refs. 1 to 4, which indicate that it is possible to realize desired luminescence by applying the organic compounds to the HTL.

Considering those results in the Experimental Examples 1 and 2, it is possible to realize a LED and a light emitting device having low driving voltage as well as enhanced luminous efficiency and quantum efficiency by applying the organic compound synthesized in accordance with the present disclosure to the HTL.

While the present disclosure has been described with reference to exemplary aspects and examples, these aspects and examples are not intended to limit the scope of the present disclosure. Rather, it will be apparent to those skilled in the art that various modifications and variations can be made in the present disclosure without departing from the spirit or scope of the disclosure. Thus, it is intended that the present disclosure covers the modifications and variations of the present disclosure provided they come within the scope of the appended claims and their equivalents.

The various aspects described above can be combined to provide further aspects. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the aspects can be modified, if necessary to employ concepts of the various patents, applications and publications to provide yet further aspects.

These and other changes can be made to the aspects in light of the above detailed description. In general, in the following claims, the terms used should not be construed to limit the claims to the specific aspects disclosed in the specification and the claims, but should be construed to include all possible aspects along with the full scope of equivalents to which such claims are entitled. Accordingly, the claims are not limited by the disclosure.

What is claimed is:

1. An organic compound selected from anyone having the following structure of Chemical Formula 4:

Chemical Formula 4

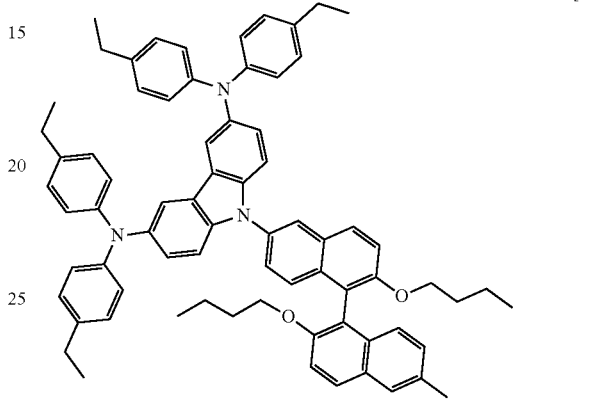

[H01]

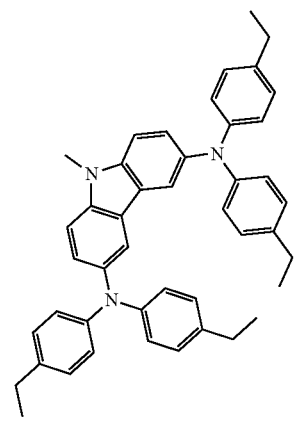

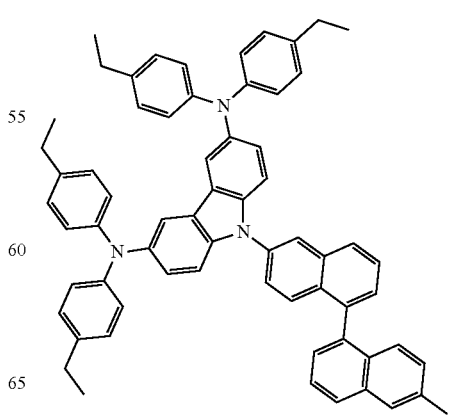

[H02]

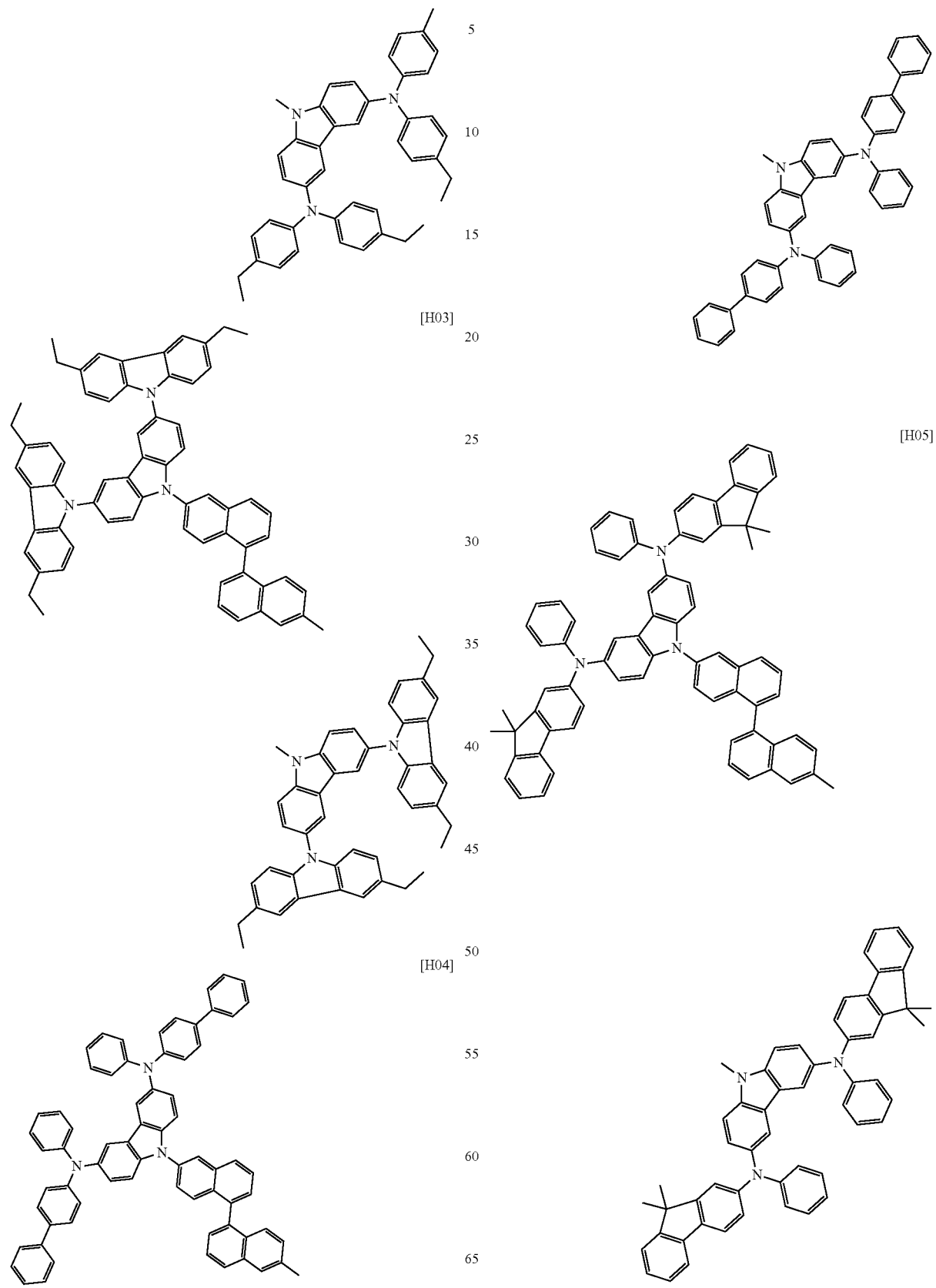

[H06]
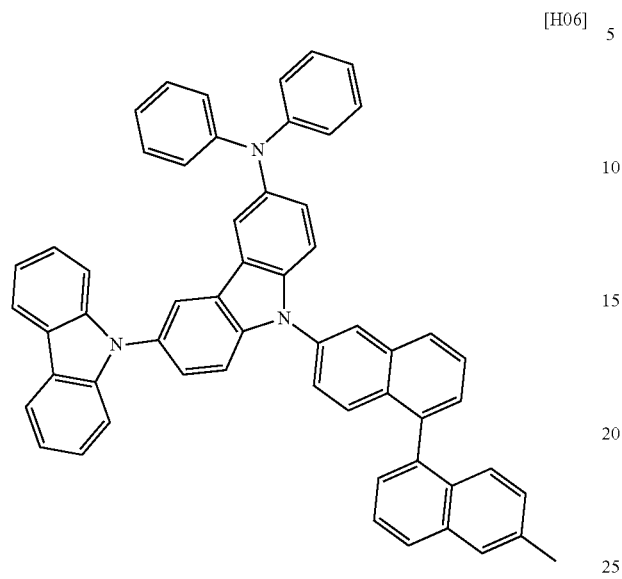
[H07]
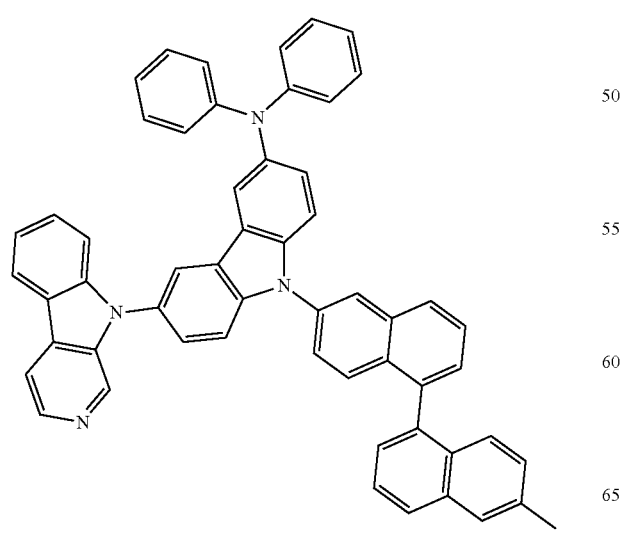
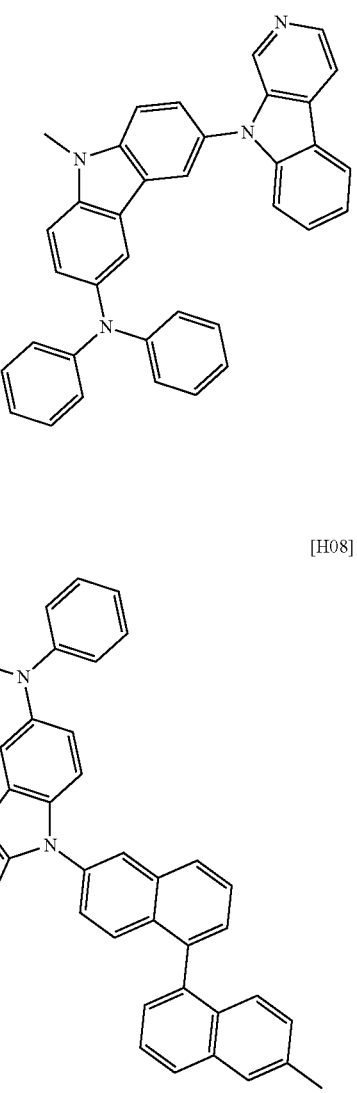
[H08]
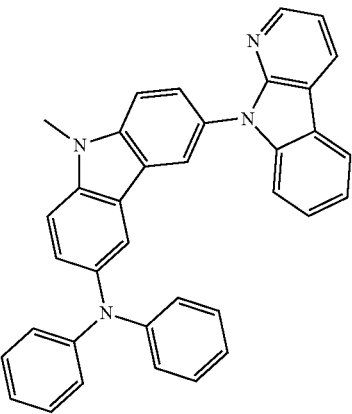

73
-continued
[H09]
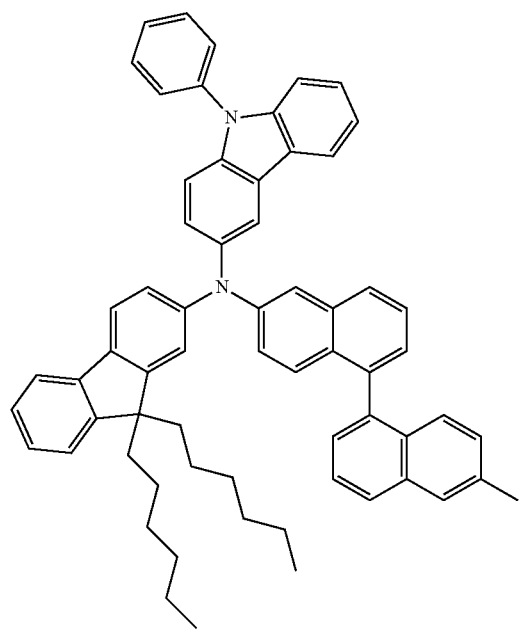
74
-continued
[H10]
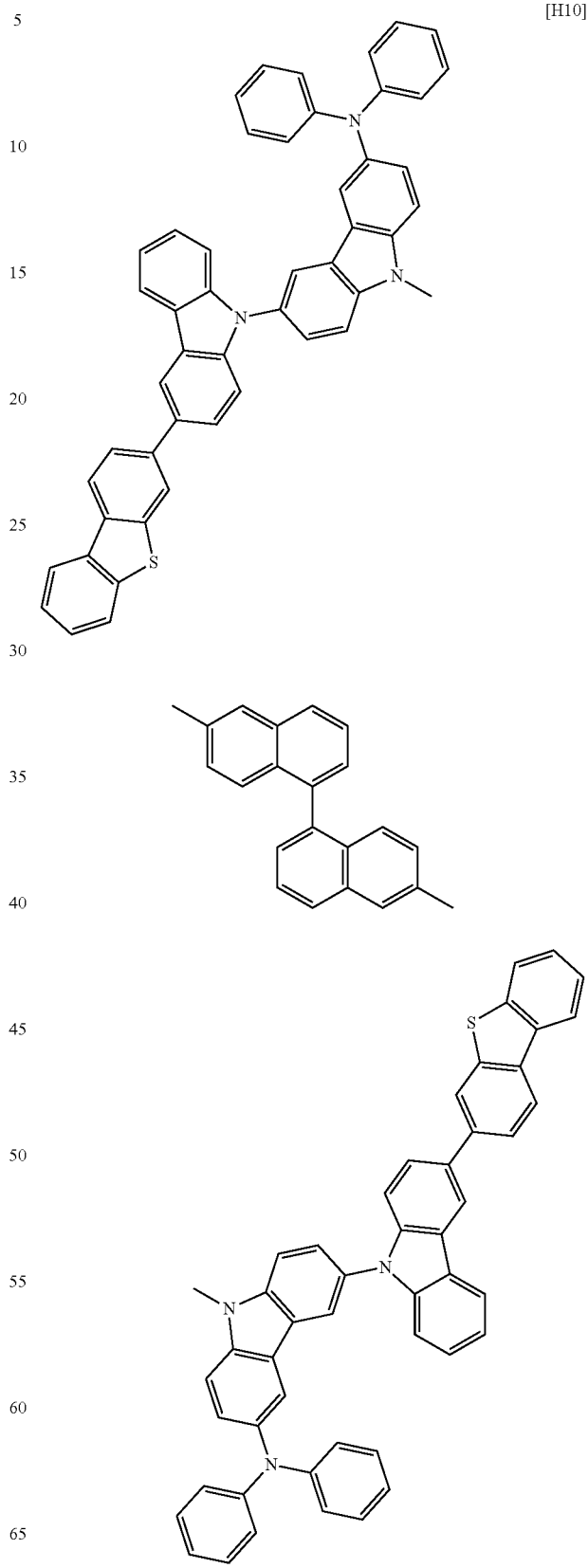

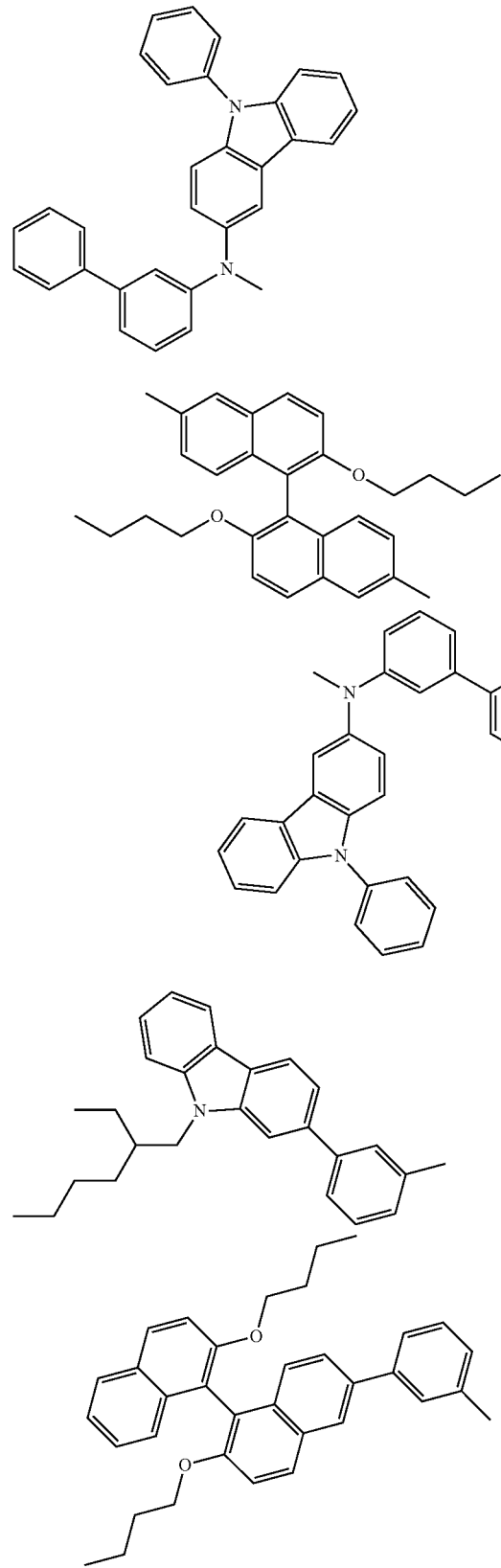
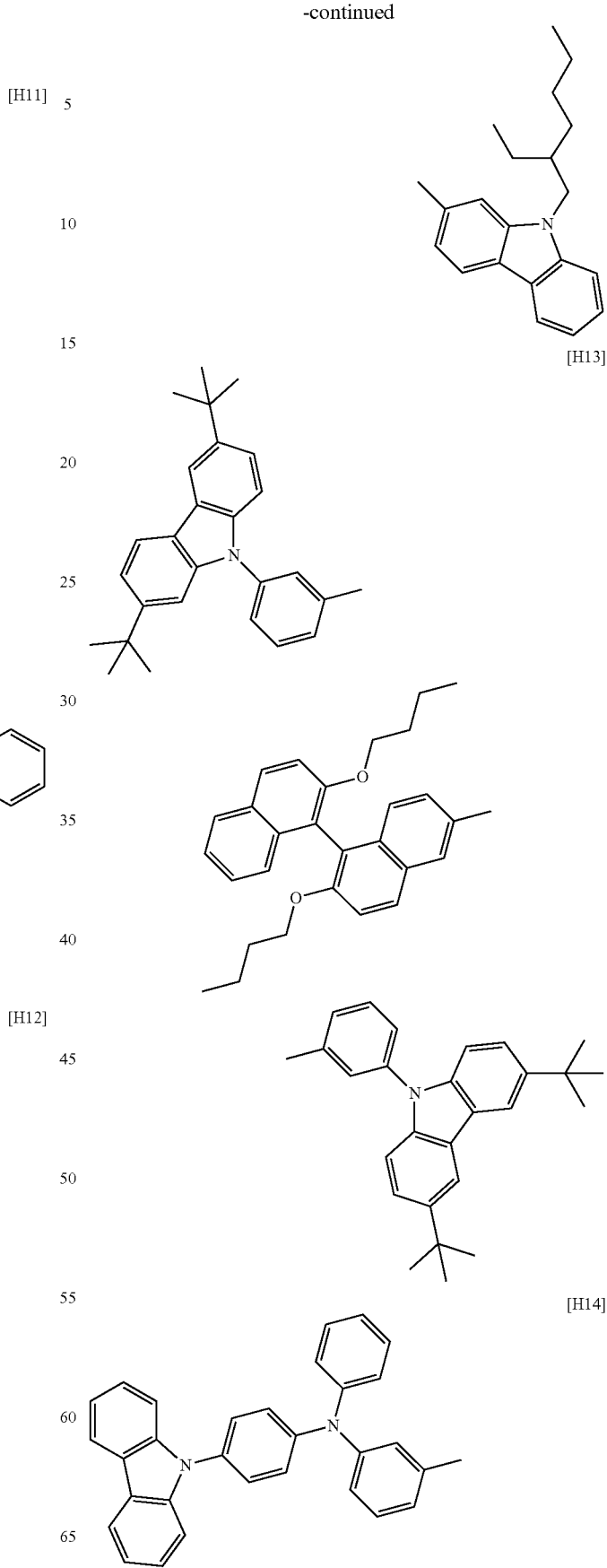

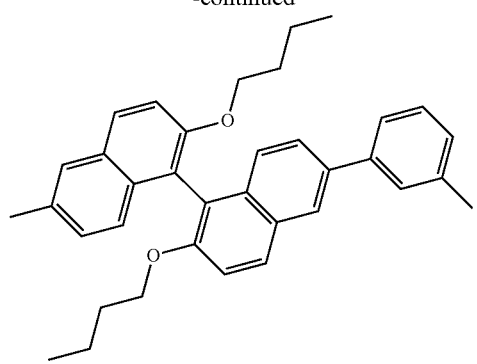
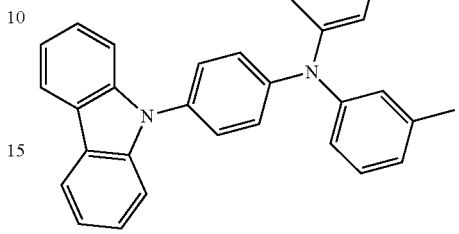
[H16]
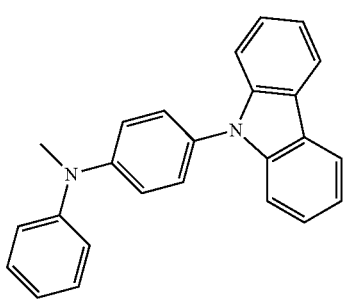
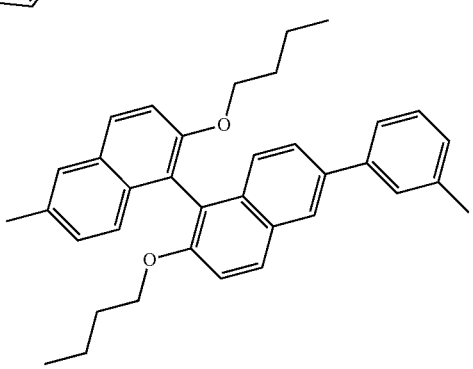
[H15]
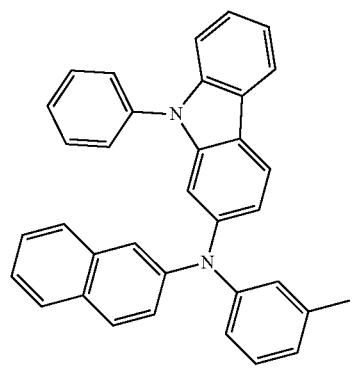
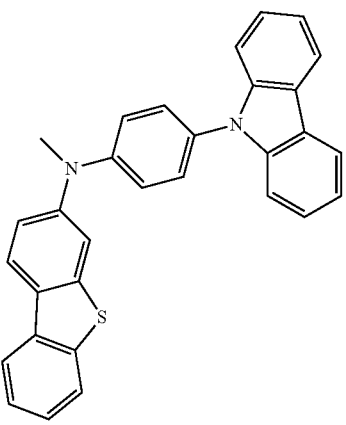
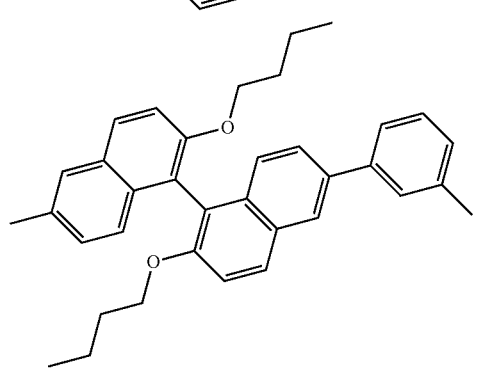
[H17]
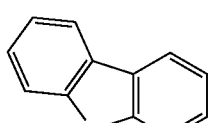
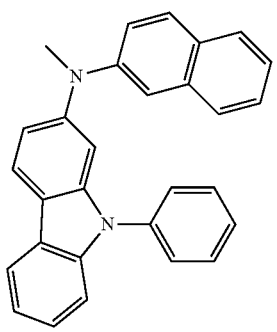
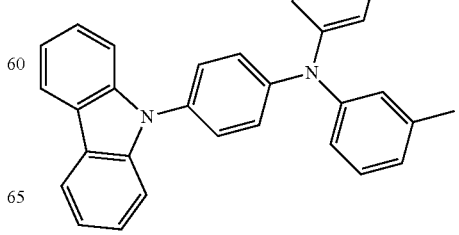

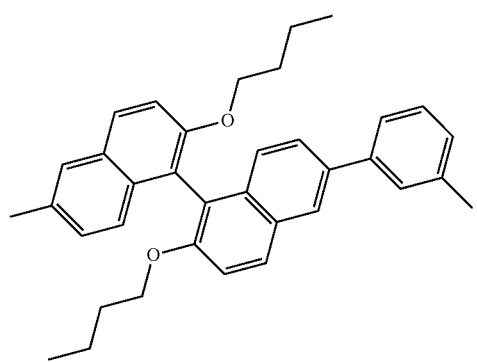
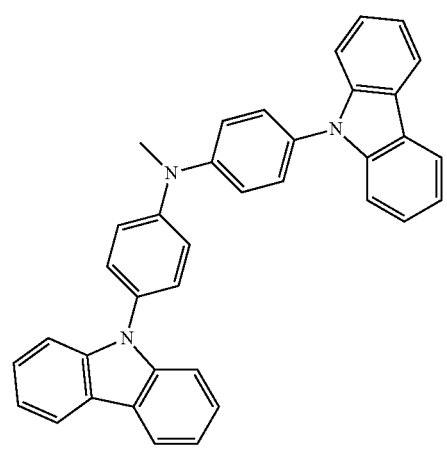
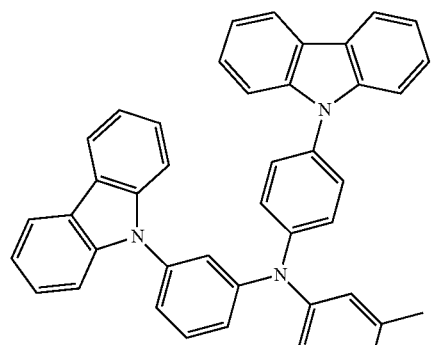
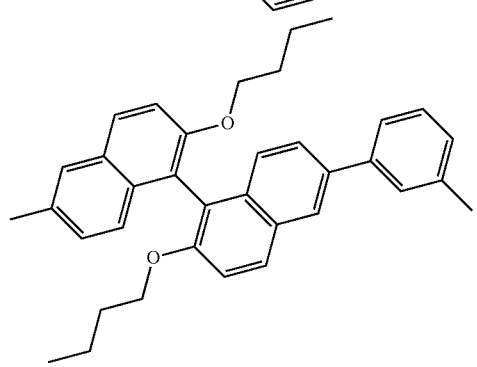
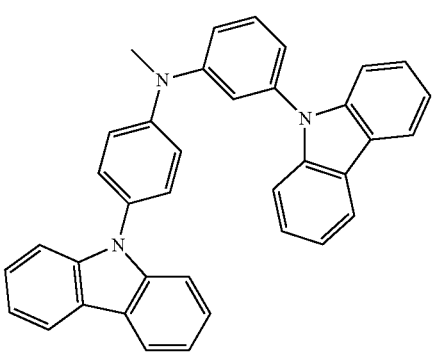
[H19]
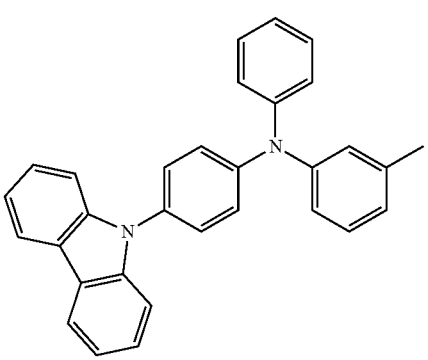
[H18]
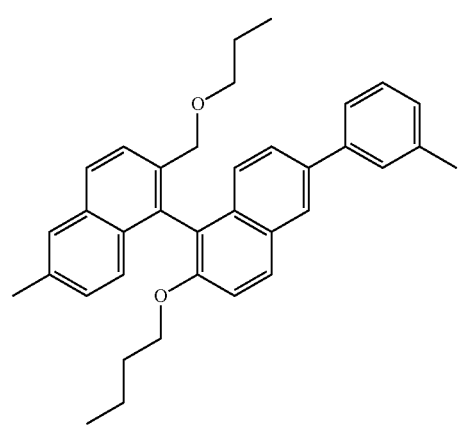
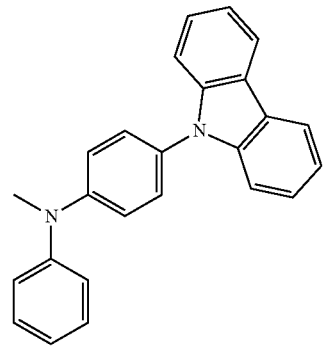

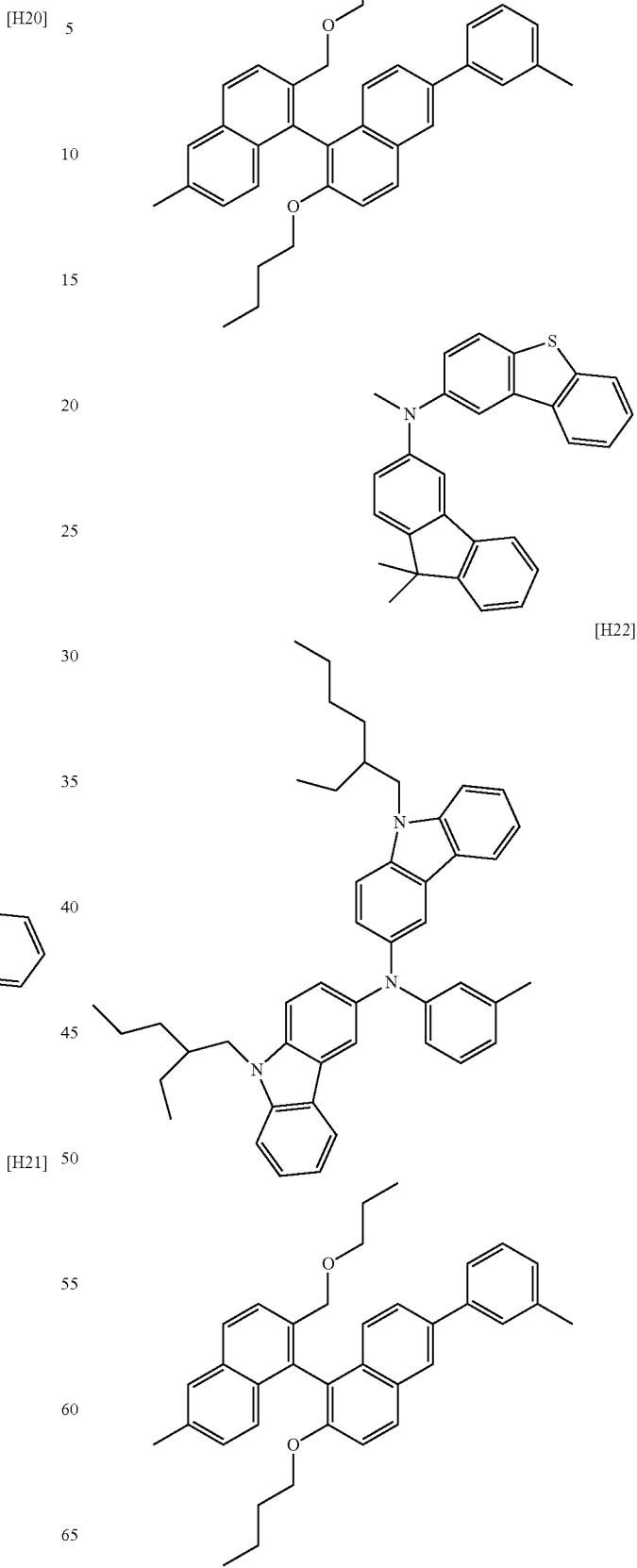
[H20]
[H21]
[H22]

-continued
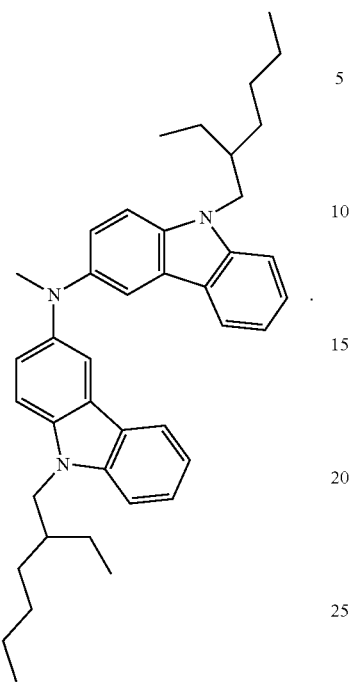
2. A light emitting diode, comprising:
first and second electrodes facing each other; and
an emissive layer between the first and second electrodes and including a hole transfer layer,
wherein the hole transfer layer includes an organic compound selected from anyone having the following structure of Chemical Formula 4:
Chemical Formula 4
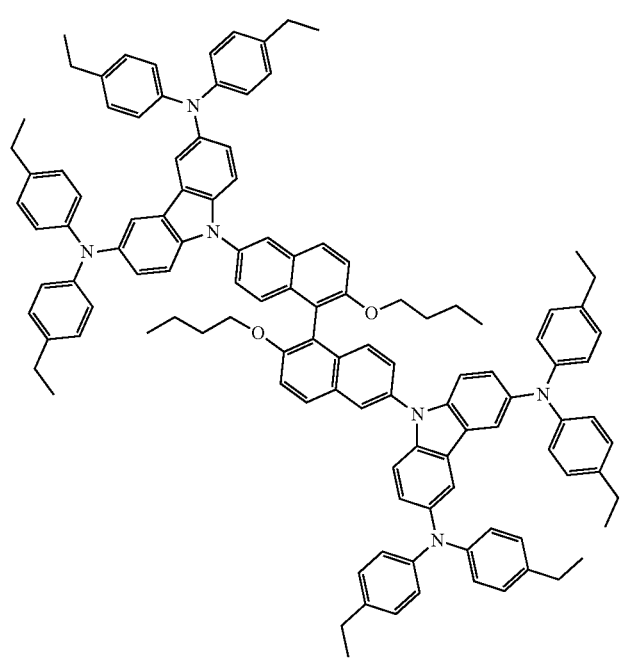
[H01]

-continued
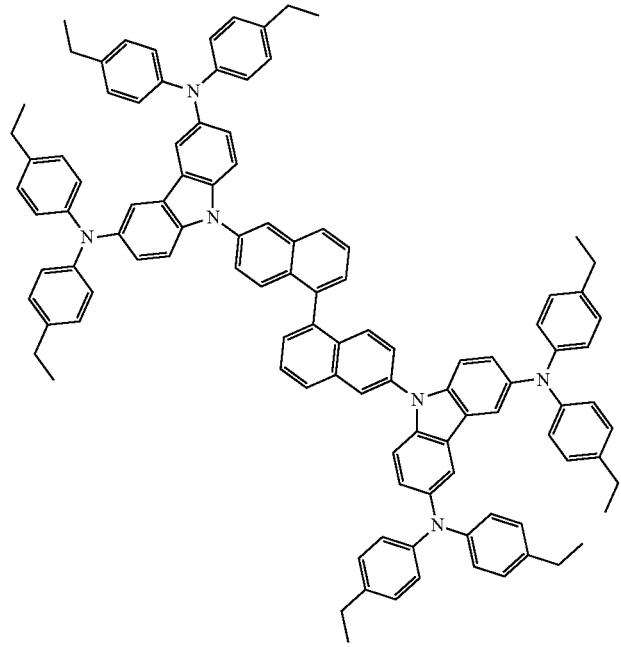
[H02]
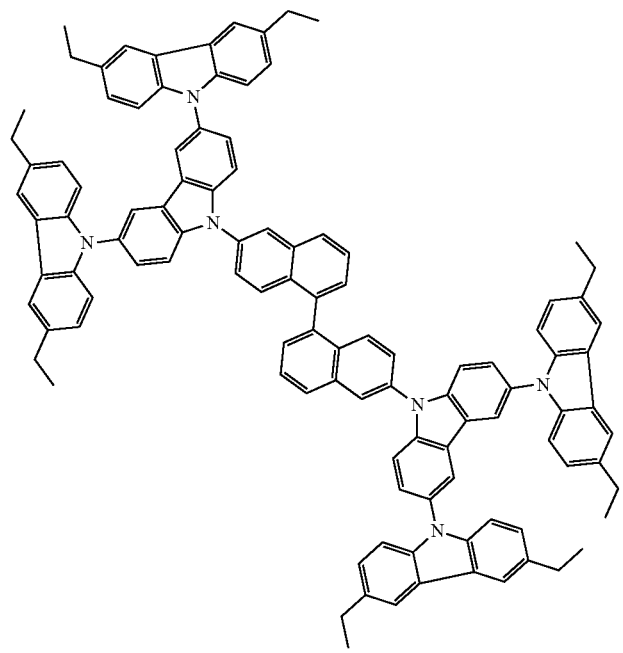
[H03]

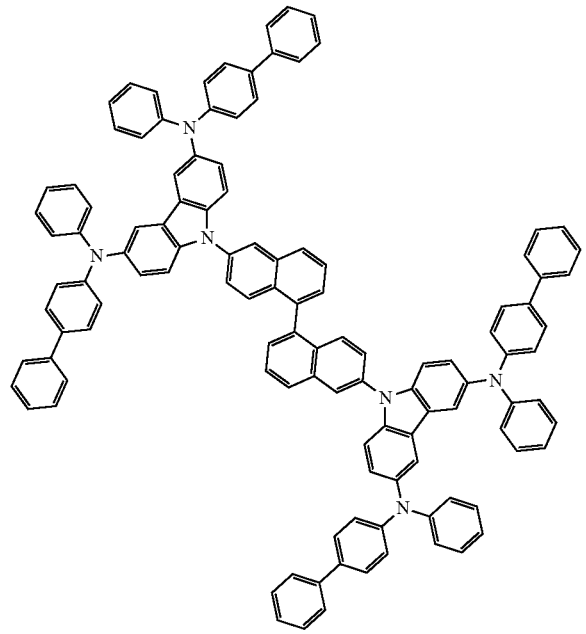
[H04]
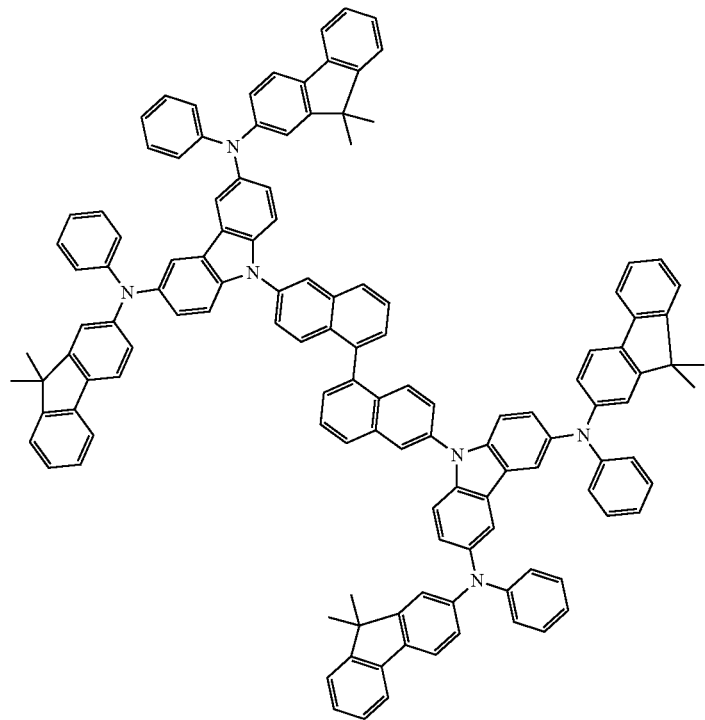
[H05]

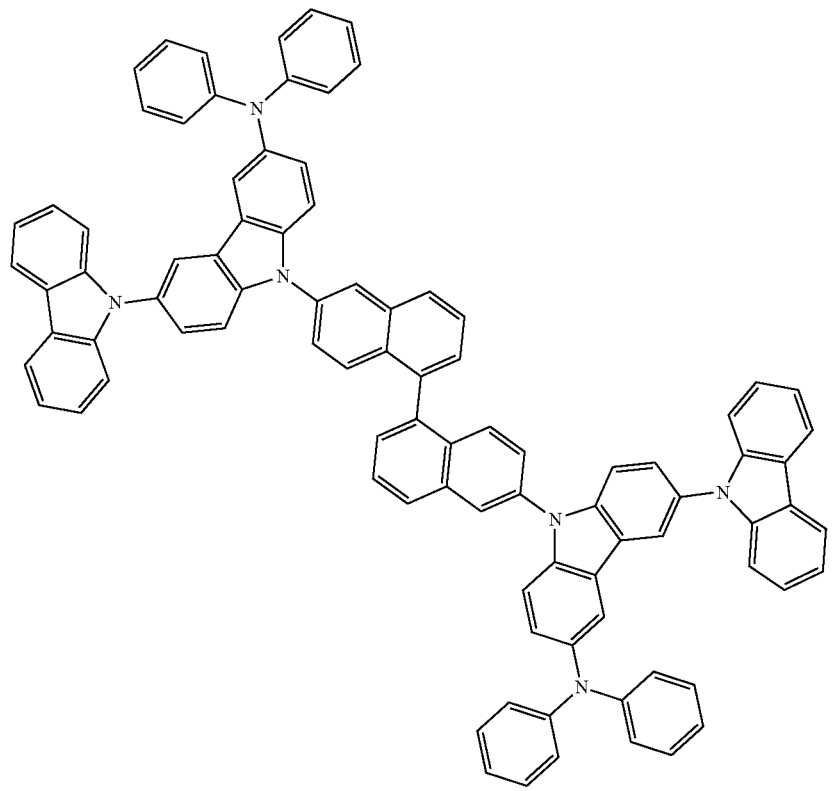
[H06]
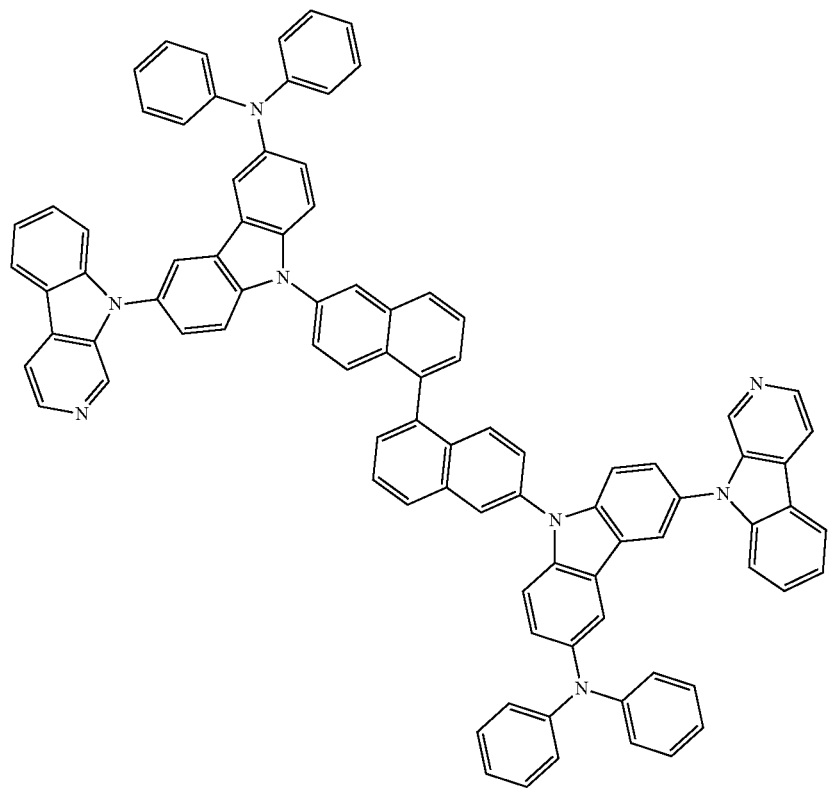
[H07]

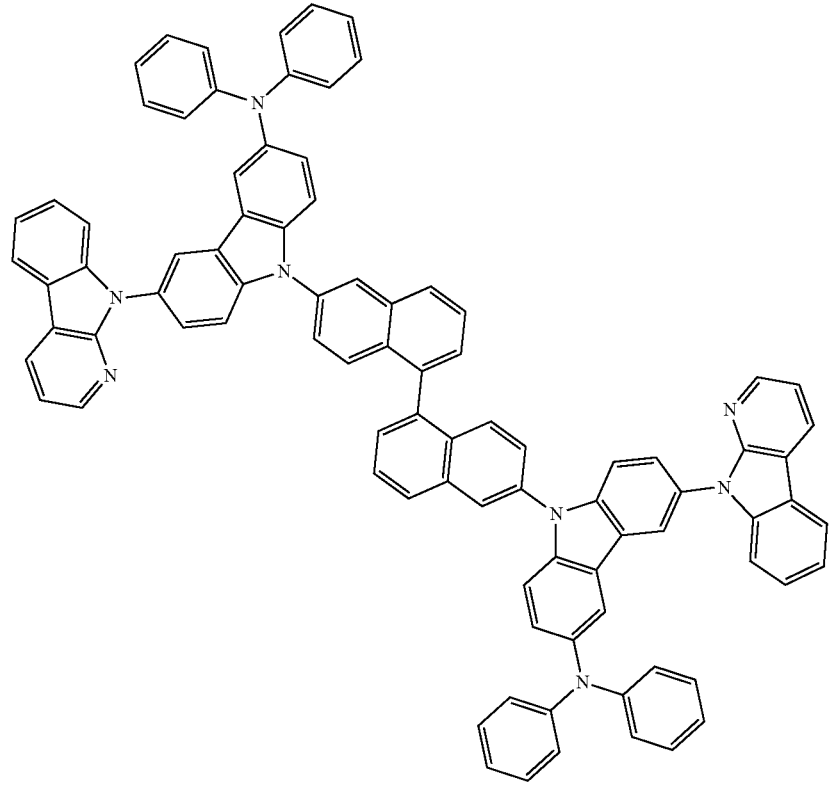
[H08]
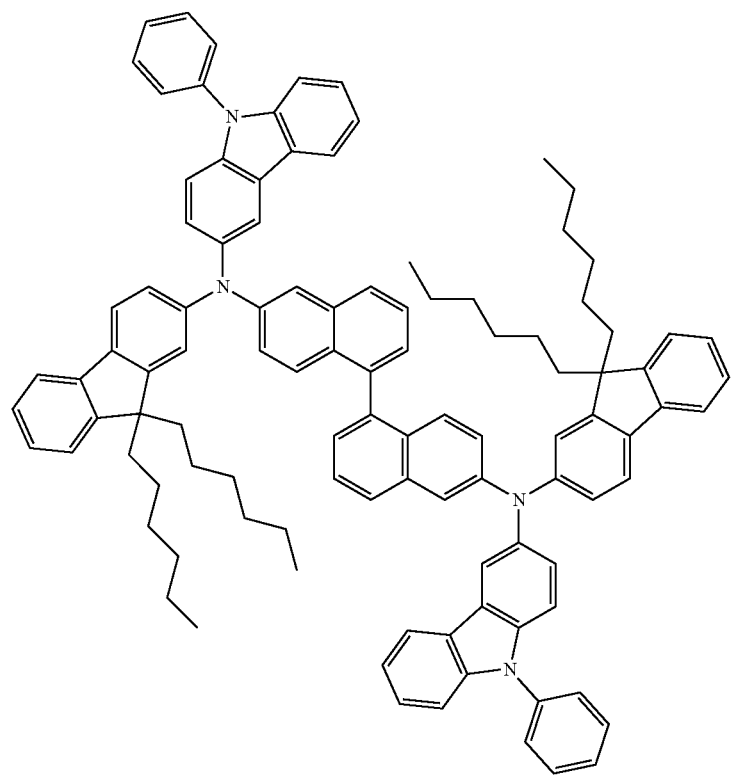
[H09]

-continued
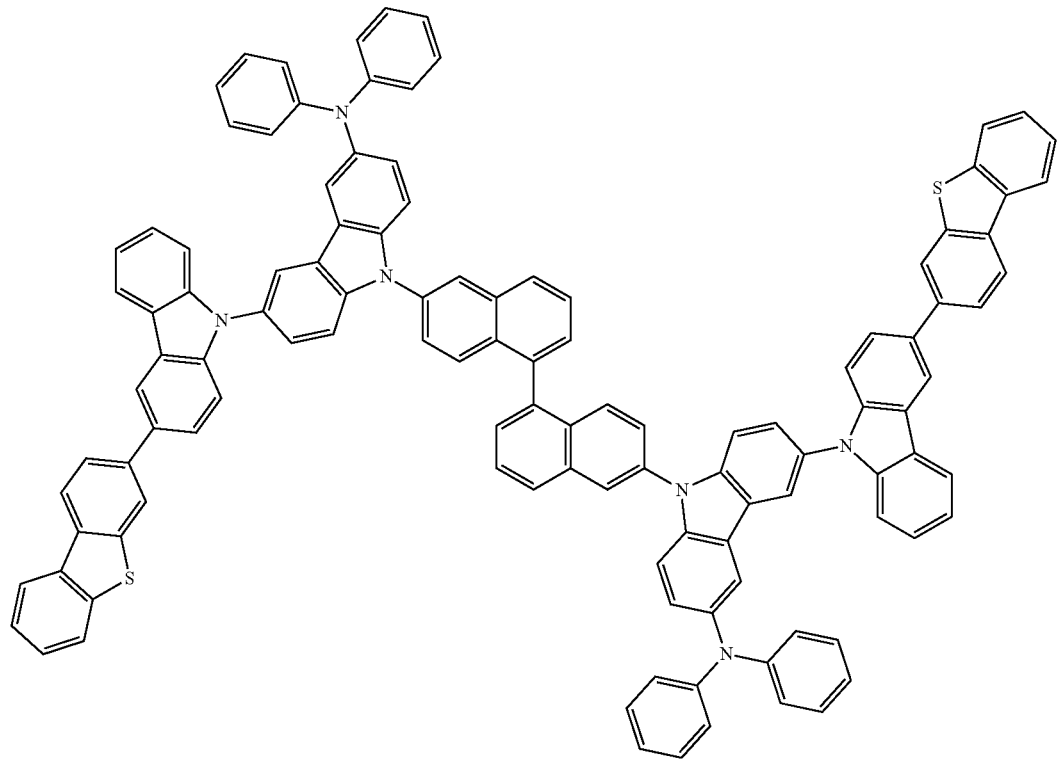
[H10]
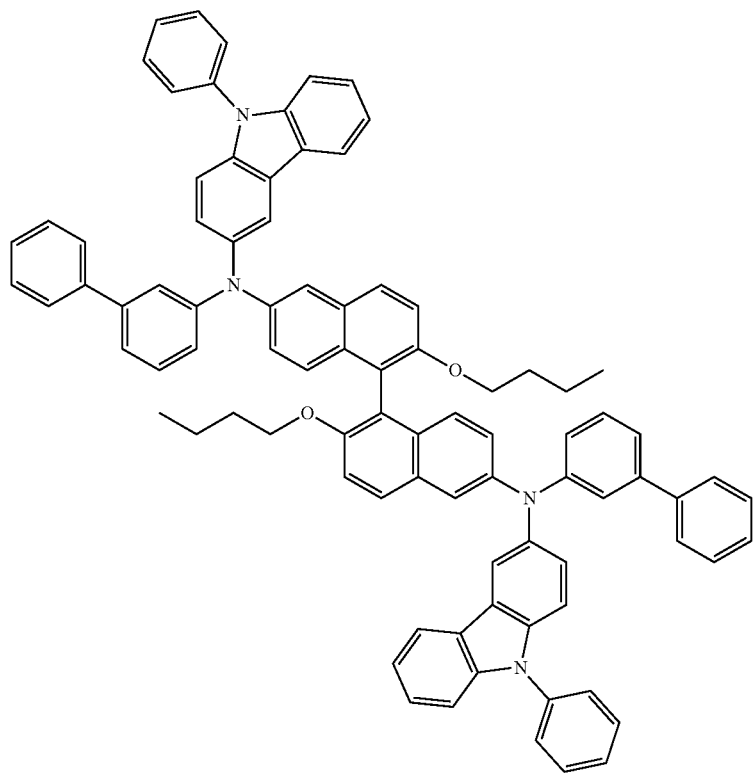
[H11]

-continued
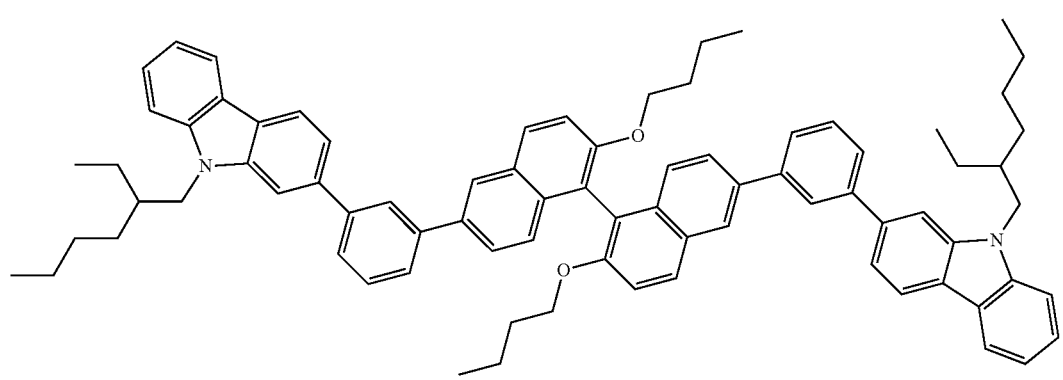
[H12]
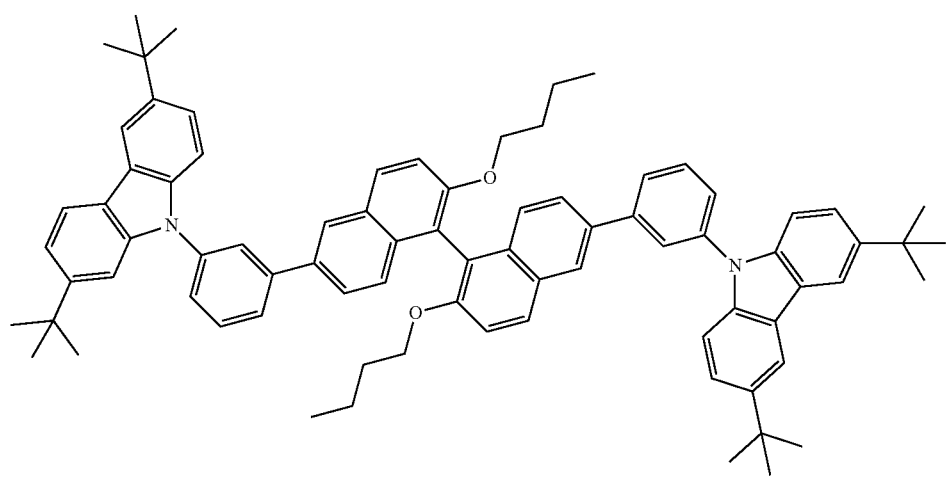
[H13]
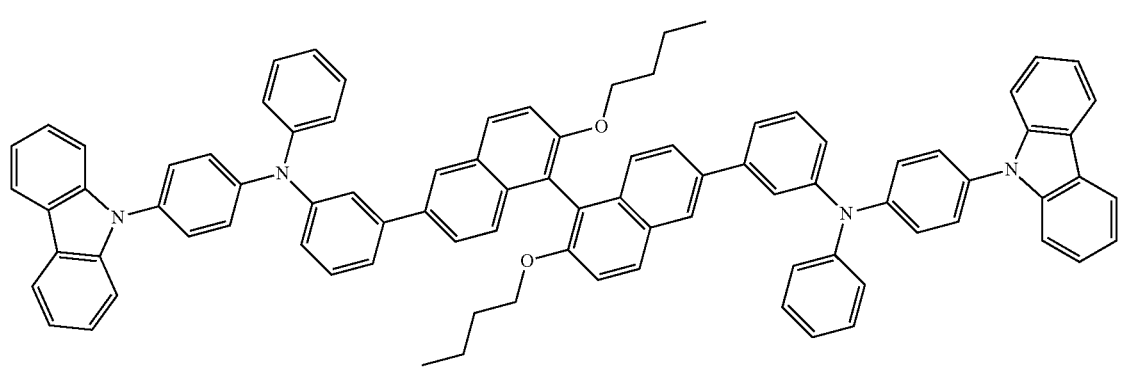
[H14]

-continued
[H15]
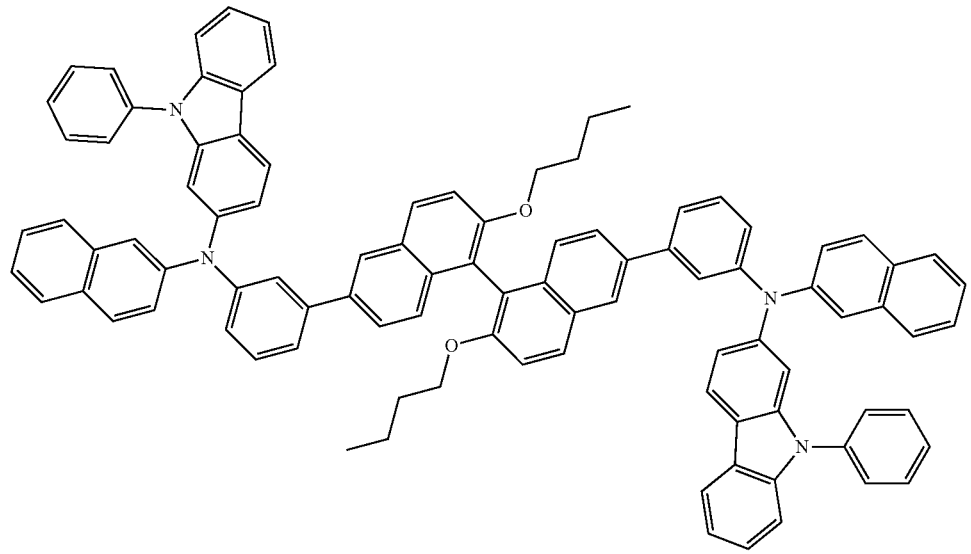
[H16]
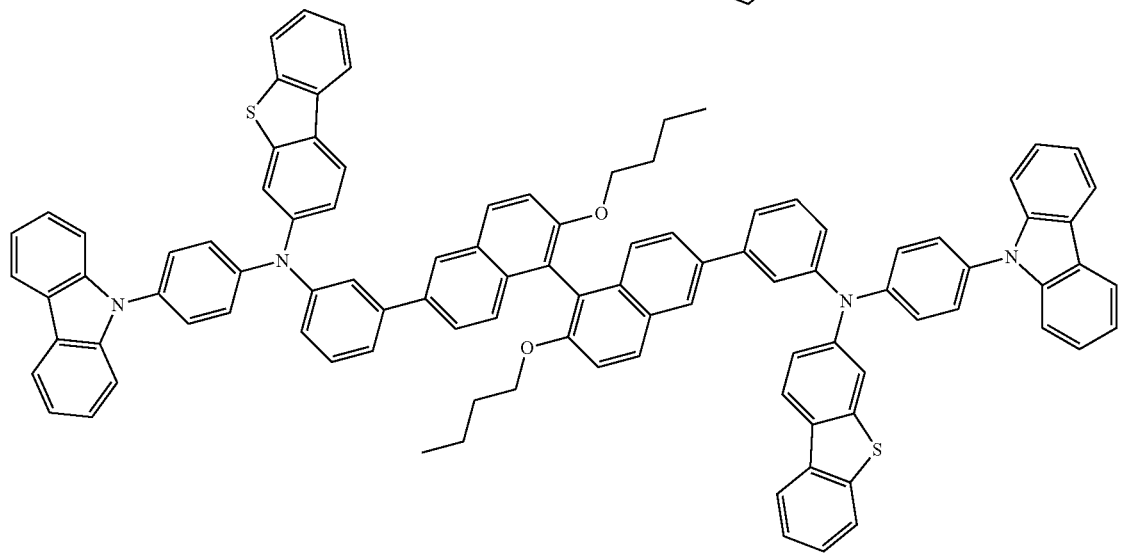
[H17]
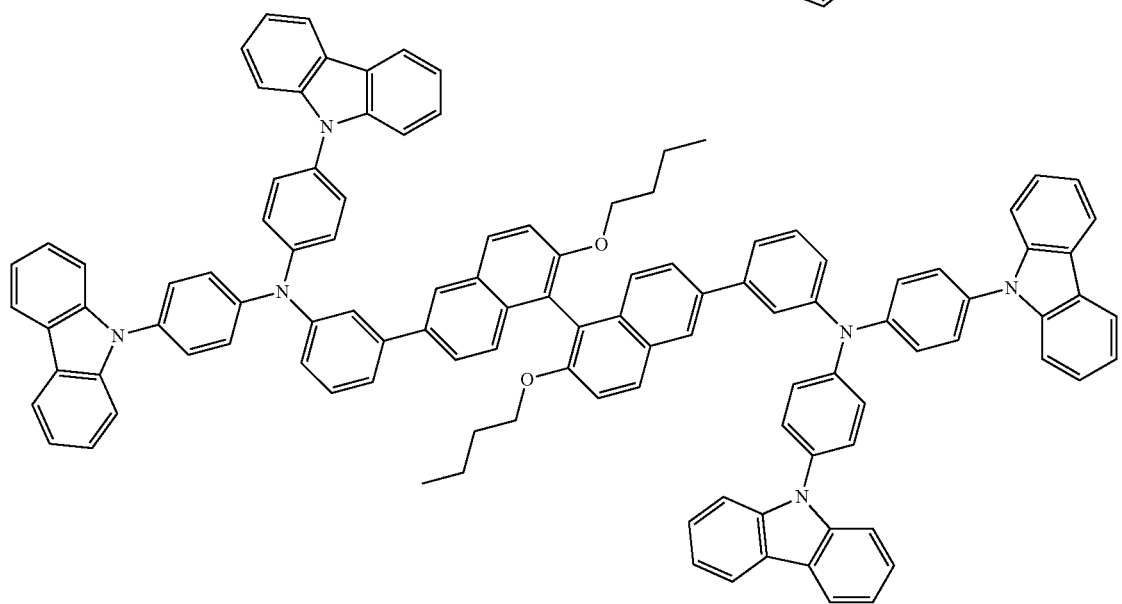

-continued
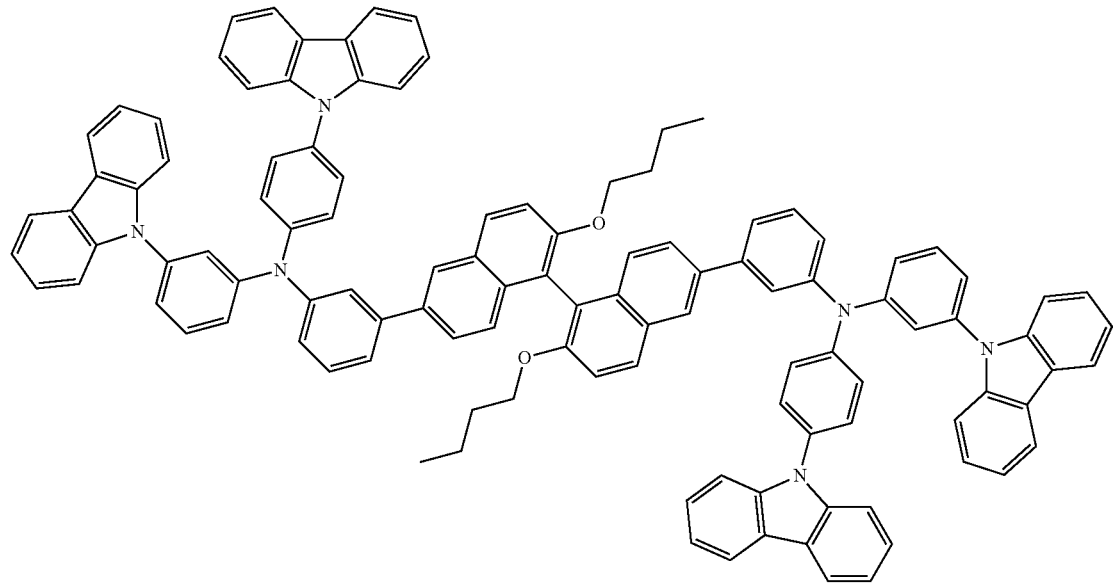
[H18]
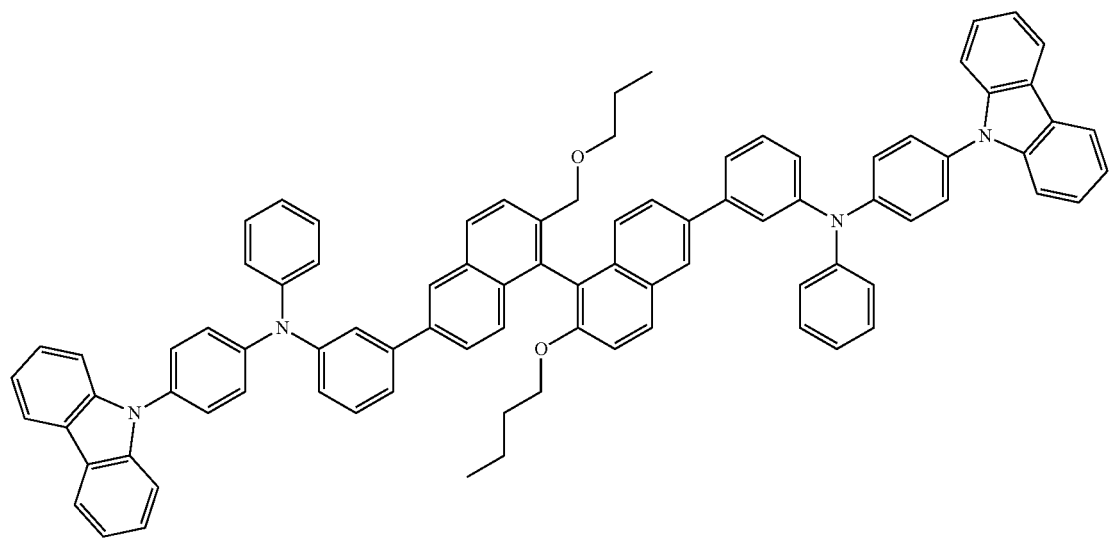
[H19]
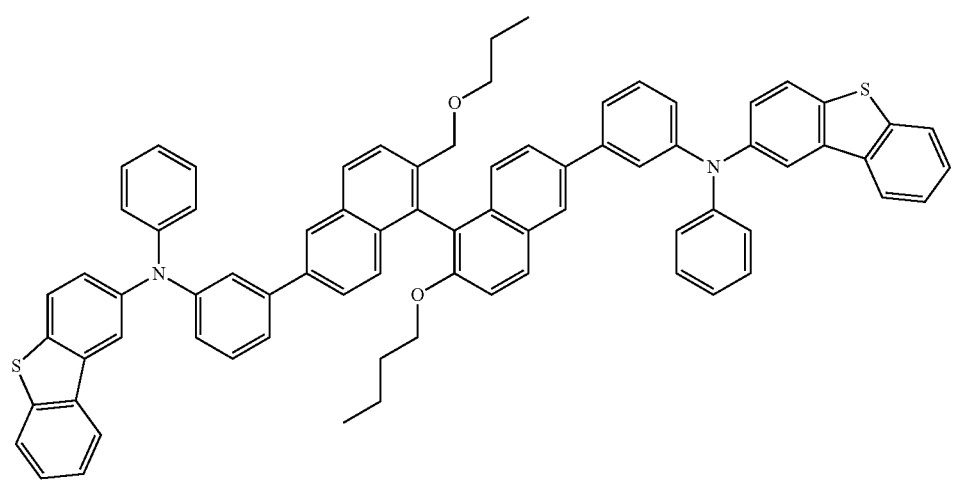
[H20]

[H21]

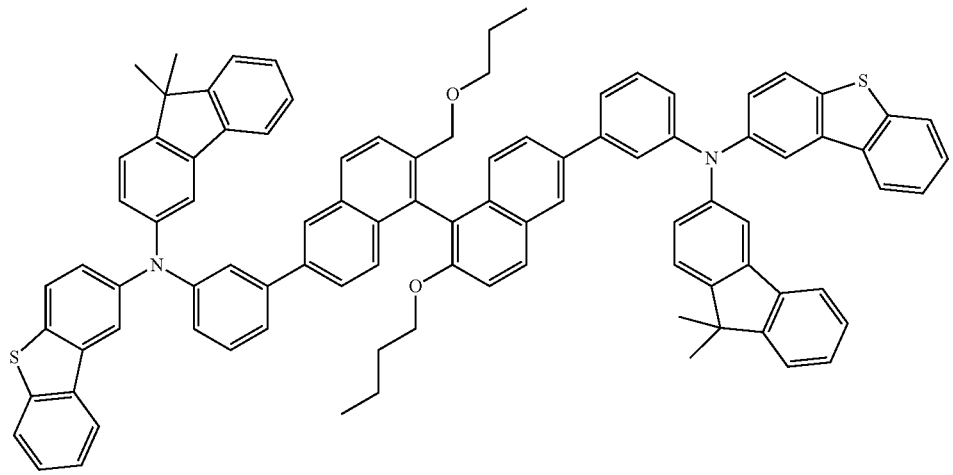

[H22]

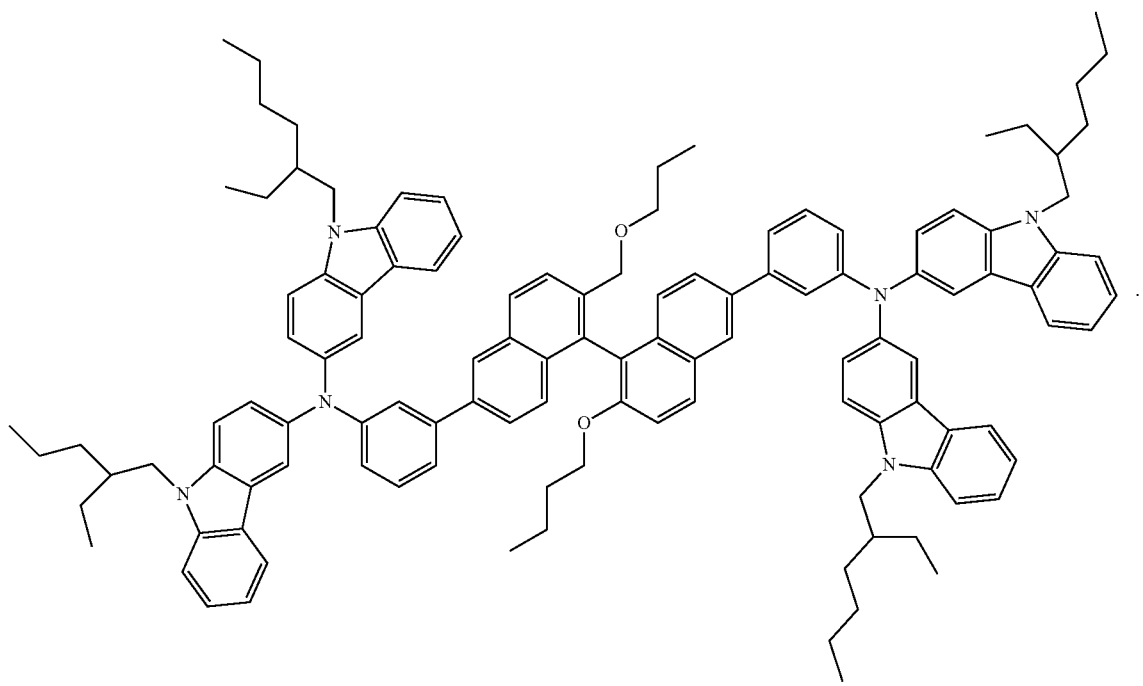

3. The light emitting diode of claim 2, wherein the emissive layer further comprises an emitting material layer.

4. The light emitting diode of claim 3, wherein the hole transfer layer is disposed between the emitting material layer and one of the first and second electrodes acting as an anode.

5. The light emitting diode of claim 4, wherein the hole transfer layer includes a hole injection layer between the anode and the emitting material layer and a hole transport layer disposed between the hole injection layer and the emitting material layer.

6. The light emitting diode of claim 5, wherein the hole transport layer includes the organic compound.

7. The light emitting diode of claim 6, wherein the hole transport layer includes the organic compound as a dopant.

8. The light emitting diode of claim 7, wherein the hole transport layer include anyone host having the following structure of Chemical Formulae 5 to 8:

Chemical Formula 5

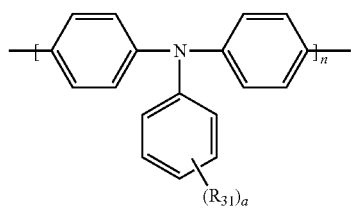

-continued

Chemical Formula 6

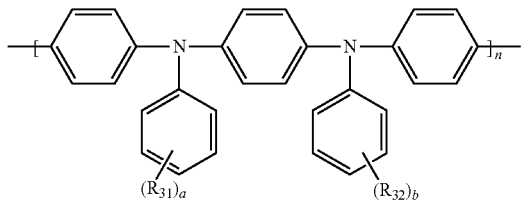

Chemical Formula 7

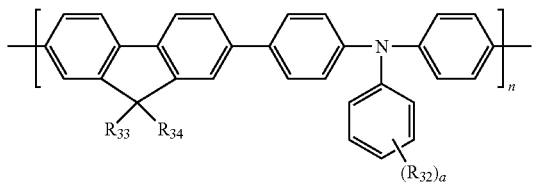

Chemical Formula 8

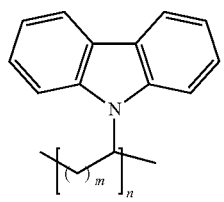

wherein each of $R_{31}$ to $R_{34}$ is independently unsubstituted or substituted linear or branched $C_1$~$C_{20}$ alkyl group, unsubstituted or substituted $C_1$~$C_{20}$ alkoxy group, unsubstituted or substituted $C_5$~$C_{30}$ aryl group or unsubstituted or substituted $C_4$~$C_{30}$ hetero aryl group; each of a and b is independently an integer of 1 to 4; n is an integer of equal to or more than 1; and m is an integer of 1 to 10.

9. The light emitting diode of claim 5, wherein the hole transport layer includes a first hole transport layer disposed between the hole injection layer and the emitting material layer and a second hole transport layer disposed between the first hole transport layer and the emitting material layer.

10. The light emitting diode of claim 9, wherein the second hole transport layer includes the organic compound.

11. The light emitting diode of claim 9, wherein the first hole transport layer includes an organic material having anyone of the following structure of Chemical Formulae 5 to 8:

Chemical Formula 5

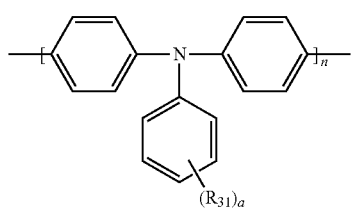

-continued

Chemical Formula 6

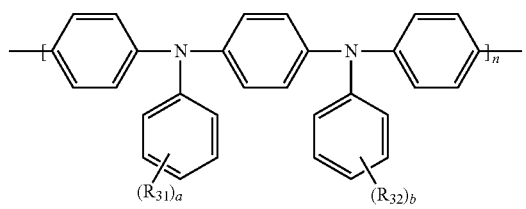

Chemical Formula 7

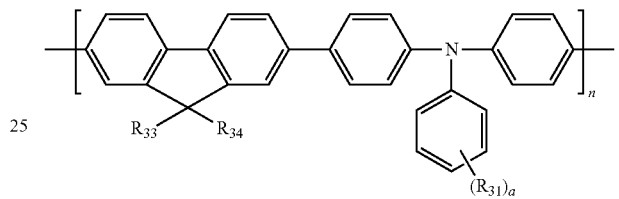

Chemical Formula 8

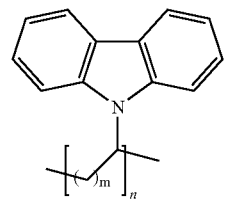

wherein each of $R_{31}$ to $R_{34}$ is independently unsubstituted or substituted linear or branched $C_1$~$C_{20}$ alkyl group, unsubstituted or substituted $C_1$~$C_{20}$ alkoxy group, unsubstituted or substituted $C_5$~$C_{30}$ aryl group or unsubstituted or substituted $C_4$~$C_{30}$ hetero aryl group; each of a and b is independently an integer of 1 to 4; n is an integer of equal to or more than 1; and m is an integer of 1 to 10.

12. The light emitting diode of claim 3, wherein the emitting material layer includes inorganic luminescent particles.

13. The light emitting diode of claim 12, wherein the inorganic luminescent particles include quantum dots (QDs) or quantum rods (QRs).

14. A light emitting device, comprising:
a substrate; and
a light emitting diode according to claim 2 over the substrate.

15. The light emitting device of claim 14, wherein the light emitting device includes a light emitting display device and a light emitting illumination device.

16. An organic compound having the following structure of Chemical Formula 2:

Chemical Formula 2

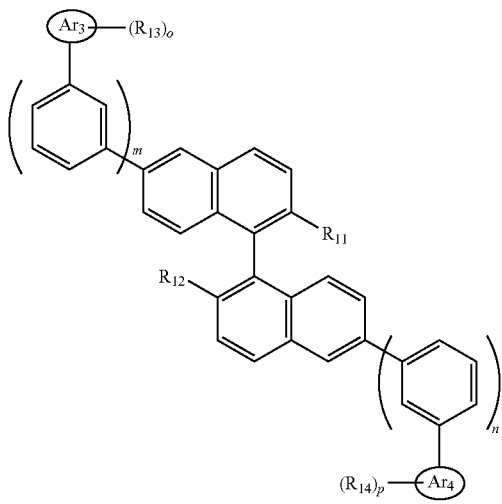

wherein each of $R_{11}$ and $R_{12}$ is independently protium, deuterium, tritium or linear or branched $C_1$~$C_{10}$ alkyl group; each of $Ar_3$ and $Ar_4$ is $C_{10}$~$C_{30}$ fused hetero aryl group; each of $R_{13}$ and $R_{14}$ is independently $C_5$~$C_{30}$ aryl amino group unsubstituted or substituted with linear or branched $C_1$~$C_{10}$ alkyl group, $C_4$~$C_{30}$ hetero aryl amino group unsubstituted or substituted with linear or branched $C_1$~$C_{10}$ alkyl group, $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof; or $C_4$~$C_{30}$ hetero aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof; each of o and p is independently a number of substituents $R_{13}$ and $R_{14}$ and an integer of 1 to 2; and each of m and n is independently an integer of 0 or 1.

17. A light emitting diode, comprising:

first and second electrodes facing each other; and an emissive layer between the first and second electrodes and including a hole transfer layer, wherein the hole transfer layer includes an organic compound having the following structure of Chemical Formula 2:

Chemical Formula 2

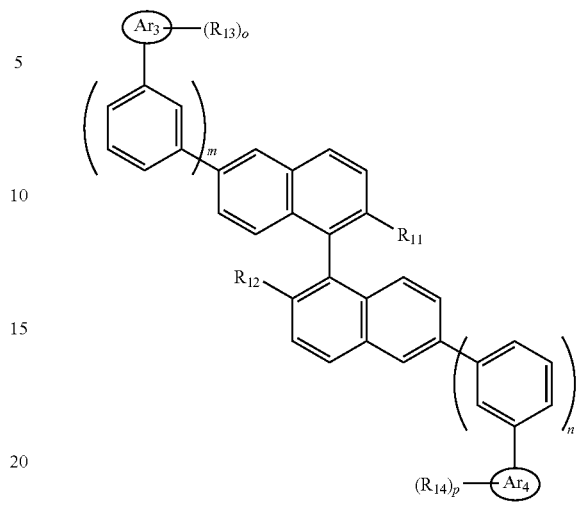

wherein each of $R_{11}$ and $R_{12}$ is independently protium, deuterium, tritium, linear or branched $C_1$~$C_{10}$ alkyl group or $C_1$~$C_{10}$ alkoxy group; each of $Ar_3$ and $Ar_4$ is $C_{10}$~$C_{30}$ fused hetero aryl group; each of $R_{13}$ and $R_{14}$ is independently $C_5$~$C_{30}$ aryl amino group unsubstituted or substituted with linear or branched $C_1$~$C_{10}$ alkyl group, $C_4$~$C_{30}$ hetero aryl amino group unsubstituted or substituted with linear or branched $C_1$~$C_{10}$ alkyl group, $C_5$~$C_{30}$ aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof; or $C_4$~$C_{30}$ hetero aryl group unsubstituted or substituted with a group selected from the group consisting of linear or branched $C_1$~$C_{10}$ alkyl group, $C_5$~$C_{30}$ aryl group, $C_4$~$C_{30}$ hetero aryl group and combination thereof; each of o and p is independently a number of substituents $R_{13}$ and $R_{14}$ and an integer of 1 to 2; and each of m and n is independently an integer of 0 or 1.

18. The light emitting diode of claim 17, wherein the emissive layer further comprises an emitting material layer.

19. The light emitting diode of claim 18, wherein the hole transfer layer is disposed between the emitting material layer and one of the first and second electrodes acting as an anode.

20. The light emitting diode of claim 19, wherein the hole transfer layer includes a hole injection layer between the anode and the emitting material layer and a hole transport layer disposed between the hole injection layer and the emitting material layer.

21. The light emitting diode of claim 20, wherein the hole transport layer includes the organic compound.

22. The light emitting diode of claim 20, wherein the hole transport layer includes a first hole transport layer disposed between the hole injection layer and the emitting material layer and a second hole transport layer disposed between the first hole transport layer and the emitting material layer.

23. The light emitting diode of claim 22, wherein the second hole transport layer includes the organic compound.

24. The light emitting diode of claim 18, wherein the emitting material layer includes inorganic luminescent particles.

25. The light emitting diode of claim 24, wherein the inorganic luminescent particles include quantum dots (QDs) or quantum rods (QRs).

* * * * *